US012721879B2

(12) United States Patent
Bleicher et al.

(10) Patent No.: US 12,721,879 B2
(45) Date of Patent: Sep. 1, 2026

(54) **PEPTIDE MACROCYCLES AGAINST *ACINETOBACTER BAUMANNII***

(71) Applicant: Hoffmann-La Roche Inc., Little Falls, NJ (US)

(72) Inventors: Konrad Bleicher, Basel (CH); Daniella Cheang, St. Albans (GB); Patrick Di Giorgio, Basel (CH); Patrizio Mattei, Basel (CH); Petra Schmitz, Basel (DE); Theodor Stoll, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 198 days.

(21) Appl. No.: 18/379,626

(22) Filed: Oct. 12, 2023

(65) Prior Publication Data

US 2024/0050516 A1 Feb. 15, 2024

Related U.S. Application Data

(62) Division of application No. 16/389,292, filed on Apr. 19, 2019, now Pat. No. 11,819,532.

(30) Foreign Application Priority Data

Apr. 23, 2018 (WO) ................ PCT/CN2018/084131

(51) Int. Cl.
*A61K 38/12* (2006.01)
*A61P 31/04* (2006.01)

(52) U.S. Cl.
CPC .............. *A61K 38/12* (2013.01); *A61P 31/04* (2018.01)

(58) Field of Classification Search
CPC ........ A61K 38/12; A61K 38/00; A61K 38/06; A61P 31/04; A61P 31/00; C07K 5/0819; C07K 5/0815; C07K 5/06086
See application file for complete search history.

(56) References Cited

U.S. PATENT DOCUMENTS 7,521,420 B2 4/2009 Fraser et al.
10,030,047 B2 7/2018 Alanine
11,066,443 B2 7/2021 Alanine et al.
11,098,080 B2 8/2021 Alanine et al.
11,505,573 B2 11/2022 Bleicher et al.
2005/0256037 A1 11/2005 Lampe et al.
2006/0004185 A1 1/2006 Leese et al.
2006/0025566 A1 2/2006 Hoveyda et al.
2006/0258571 A1 11/2006 Lampe et al.
2007/0021331 A1 1/2007 Fraser et al.
2008/0275018 A1 11/2008 Endermann et al.
2017/0233437 A1* 8/2017 Alanine .................. C07K 5/08 514/2.8
2019/0300569 A1 10/2019 Bleicher et al.
2019/0321440 A1 10/2019 Bleicher et al.
2020/0040031 A1 2/2020 Alanine et al.
2022/0411468 A1 12/2022 Alanine et al.

FOREIGN PATENT DOCUMENTS

CL 200402547 9/2005
CN 103387601 A 11/2013
CN 107073095 A 8/2017
EP 1498422 1/2005
EP 3388444 A1 10/2018
RU 2428429 C2 9/2011
WO 01/14346 A1 3/2001
WO 03/106480 A1 12/2003
WO 2004/012816 A1 2/2004
WO 2004/018478 A2 3/2004
(Continued)

OTHER PUBLICATIONS

Azuma, H. et al., "A Publication of Reliable Methods for the Preparation of Organic Compounds Working with Hazardous Chemicals" Org. Synth 88:152-161 (Jan. 14, 2011).
(Continued)

*Primary Examiner* — Joseph Fischer
(74) *Attorney, Agent, or Firm* — James M. Turner

(57) ABSTRACT

The present invention provides compounds of formula (I)

(I)

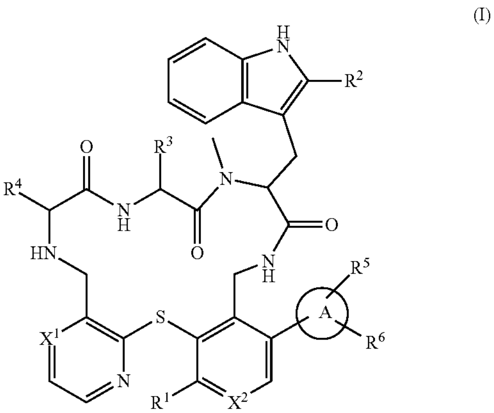

wherein $X^1$, $X^2$, $R^1$ to $R^6$ and A are as described herein, as well as pharmaceutically acceptable salts thereof. Further the present invention is concerned with the manufacture of the compounds of formula (I), pharmaceutical compositions comprising them and their use as medicaments for the treatment of diseases and infections caused by bacteria.

10 Claims, No Drawings

(56) References Cited

FOREIGN PATENT DOCUMENTS

| | | | |
|---|---|---|---|
| WO | 2004/111077 | A1 | 12/2004 |
| WO | 2005/012331 | A1 | 2/2005 |
| WO | 2005/012332 | A1 | 2/2005 |
| WO | 2005/033129 | | 4/2005 |
| WO | 2005/090388 | A1 | 9/2005 |
| WO | 2005/118613 | A2 | 12/2005 |
| WO | 2006/009645 | A1 | 1/2006 |
| WO | 2006/009645 | A8 | 1/2006 |
| WO | 2006/009674 | A1 | 1/2006 |
| WO | 2006/009674 | A8 | 1/2006 |
| WO | 2006/074964 | A1 | 7/2006 |
| WO | 2006/083317 | A2 | 8/2006 |
| WO | 2006/103015 | A1 | 10/2006 |
| WO | 2007/131966 | A1 | 11/2007 |
| WO | 2009/099677 | A2 | 8/2009 |
| WO | 2010/022249 | A2 | 2/2010 |
| WO | 2010/022249 | A3 | 2/2010 |
| WO | 2011/050270 | A2 | 4/2011 |
| WO | 2011/050270 | A3 | 4/2011 |
| WO | 2011/050276 | A1 | 4/2011 |
| WO | 2011/053821 | A1 | 5/2011 |
| WO | 2013/033645 | A1 | 3/2013 |
| WO | 2013/123266 | A1 | 8/2013 |
| WO | 2014/048976 | | 4/2014 |
| WO | 2014/081886 | A1 | 5/2014 |
| WO | 2014/110420 | A1 | 7/2014 |
| WO | 2008/095999 | A1 | 8/2014 |
| WO | 2015/169809 | | 11/2015 |
| WO | 2012/021874 | A1 | 2/2016 |
| WO | 2016/016291 | A1 | 2/2016 |
| WO | 2017/072062 | A1 | 5/2017 |
| WO | 2018/189065 | A1 | 10/2018 |
| WO | 2019/206853 | A1 | 10/2019 |

OTHER PUBLICATIONS

Ballatore, C., et al., "Carboxylic acid (bio)isosteres in drug design" Chem Med Chem 8(3):385-395 (Mar. 1, 2013).

Balraju, V., et al., "Synthesis of Cyclic Peptides Constrained with Biarylamine Linkers Using Buchwald-Hartwig C—N Coupling" J Org Chem 71(23):8954-8956 (Nov. 10, 2006).

Belikov, V.G. "Pharmaceutical Chemistry," Tutorial, 4th, revised and expanded edition, Moscow, MEDPress-Inform, 2007, pp. 27-29 (including English Translation).

Clark, J.,, "Introducing Esters" Chemguide UK (Retrieved from Webpage Apr. 19, 2022),:1-9 (Jan. 1, 2016) https://www.chemguide.co.uk/organicprops/esters/background.html.

International Search Report and Written Opinion for PCT/EP2018/058957 mailed May 28, 2018, 10 pages.

International Search Report for PCT/EP2016/075499 mailed on Jan. 5, 2017, 6 pages.

International Search Report for PCT/EP2019/057489 mailed on May 17, 2019, 4 pages.

International Search Report for PCT/EP2019/060272 mailed on Jul. 9, 2019, 4 pages.

Luther, A., et al., "Advances in macrocyclic peptide-based antibiotics" Bioorg Med Chem (Epub: Aug. 19, 2017), 26(10):2850-2858 (Jun. 1, 2018).

Marsault, E., et al., "Efficient parallel synthesis of macrocyclic peptidomimetics" Bioorg Med Chem Lett 18(16):4731-4735 (Aug. 15, 2008).

Notice of Allowances for U.S. Appl. No. 16/006,564, mailed Jul. 17, 2019, Feb. 5, 2020, Jun. 16, 2020 and Apr. 16, 2021, 29 pages.

Office action for U.S. Appl. No. 16/006,564, mailed Apr. 11, 2019, 8 pages.

Thorpe, Jim, Introducing Esters, 2004 modified 2015, 9 pages downloaded from the internet Mar. 23, 2022, from https://www.chemguide.co.uk/organicprops/esters/background.html (Year: 2016).

Wang, W., et al., "Design and synthesis of novel x2-constrained phenylalanine, naphthylalanine, and tryptophan analogues and their use in biologically active melanotropin peptides" TETRAHEDRON 58(36):7365-7374 (Dec. 31, 2002).

Wang, W., et al., "Practical, asymmetric synthesis of aromatic-substituted bulky and hydrophobic tryptophan and phenylalanine derivatives," Tetrahedron 58(15):3101-3110 (Dec. 31, 2002).

Webster, A., et al., "Synthesis of biaryl-linked cyclic peptoids" Tetrahedron Lett 58(10):1010-1014 (Mar. 8, 2017).

Written Opinion of the International Searching Authority for PCT/EP2019/060272, mailed Jul. 9, 2019, 10 pages.

Written Opinion of the International Searching Authority for PCT/EP2016/075499, mailed Jan. 5, 2017, 6 pages.

* cited by examiner

PEPTIDE MACROCYCLES AGAINST *ACINETOBACTER BAUMANNII*

CROSS-REFERENCE TO RELATED APPLICATIONS

This application is a Division of U.S. application Ser. No. 16/389,292, filed on Apr. 19, 2019, which claims benefit of priority to International Patent Application No. PCT/CN2018/084131, filed on Apr. 23, 2018, each of which is incorporated herein by reference in its entirety.

FIELD OF THE INVENTION

The present invention provides compounds which exhibit activity against bacteria, in particular against Gram-negative bacteria like *Acinetobacter baumannii*, their manufacture, pharmaceutical compositions comprising them and their use as medicaments for the treatment of diseases and infections caused by bacteria.

BACKGROUND

*Acinetobacter baumannii* is a Gram-negative, aerobic, nonfermenting bacterium recognized over the last decades as an emerging pathogen with very limited treatment options.

*A. baumannii* is considered to be a serious threat by the US Centers for Disease Control and Prevention and belongs to the so called 'ESKAPE' pathogens (*Enterococcus faecium, Staphylococcus aureus, Klebsiella pneumoniae, Acinetobacter baumannii, Pseudomonas aeruginosa* and *Enterobacter* species & *E. coli*) that currently cause the majority of nosocomial infections and effectively "escape" the activity of antimicrobial agents.

*A. baumannii* is most often encountered in intensive care units and surgical wards, where extensive antibiotic use has enabled selection for resistance against all known antimicrobials and where it causes infections that include bacteremia, pneumonia, meningitis, urinary tract infection, and wound infection.

*A. baumannii* has an exceptional ability to upregulate and acquire resistance determinates and shows an environmental persistence that allows its survival and spread in the nosocomial setting, making this organism a frequent cause of outbreaks of infection and an endemic, health care-associated pathogen.

Due to increasing antibiotic resistance to most if not all available therapeutic options, Multi-Drug Resistant (MDR) *A. baumannii* infections, especially those caused by Carbapenem resistant *A. baumannii*, are extremely difficult or even impossible to treat with high mortality rate as well as increased morbidity and length of stay in intensive care unit.

*Acinetobacter baumannii* has been defined and still remains "a prime example of a mismatch between unmet medical needs and the current antimicrobial research and development pipeline" according to the Antimicrobial Availability Task Force (AATF) of the Infectious Diseases Society of America (IDSA). Thus, there is a high demand and need to identify compounds suitable for the treatment of diseases and infections caused by *Acinetobacter baumannii.*

WO2017/072062 discloses peptide macrocycles that are active against *Acinetobacter baumannii*. However, there is still a high unmet need for improved compounds suitable for the treatment of diseases and infections caused by *Acinetobacter baumannii.*

SUMMARY OF THE DISCLOSURE

In a first aspect, the present invention provides a compound of formula (I)

(I)

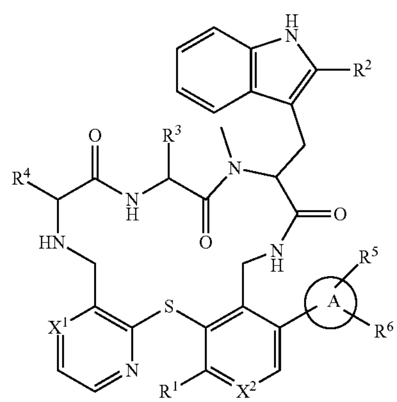

or a pharmaceutically acceptable salt thereof, wherein:

$X^1$ is CH or N;

$X^2$ is CH or N;

A is selected from:

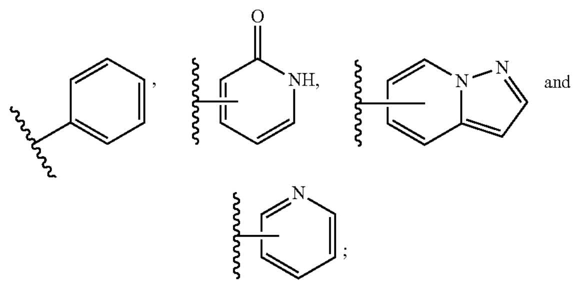

, , and ;

$R^1$ is selected from hydrogen, halogen, $C_{1-6}$-alkoxy and $C_{1-6}$-alkyl;

$R^2$ is hydrogen or $C_{1-6}$-alkyl;

$R^3$ is $C_{1-6}$-aminoalkyl;

$R^4$ is $C_{1-6}$-aminoalkyl or carbamoyl-$C_{1-6}$-alkyl;

$R^5$ is selected from carboxy, carboxy-$C_{1-6}$-alkyl and carboxy-$C_{2-6}$-alkenyl; and $R^6$ is selected from hydrogen, halogen, hydroxy, $C_{1-6}$-alkoxy and $C_{1-6}$-alkylsulfonyl; provided that said compound of formula (I) is not:

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-22-yl]-benzoic acid.

In a further aspect, the present invention provides a process for the manufacture of the compounds of formula (I) described herein, comprising:

a) cleaving all amino-, indole- and carboxy protecting groups present in a compound of formula (VI), wherein $R^1$, $R^2$, $R^{5'}$, $R^6$, $R^{30}$, $R^{40}$, $X^1$ and $X^2$ are as defined herein, (VI)

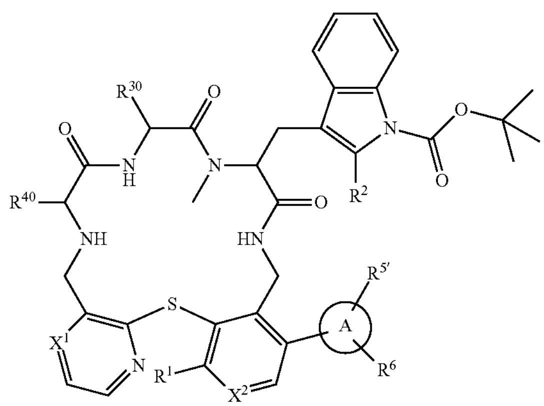

to afford said compound of formula (I).

In a further aspect, the present invention provides a process for the manufacture of compounds of formula (IXa) or (IXb), wherein $PG^1$ is a suitable protecting group for the indole nitrogen, $PG^2$ is a suitable amino protecting group and $R^8$ and $R^{20}$ are each independently $C_{1-6}$-alkyl, (IXa)

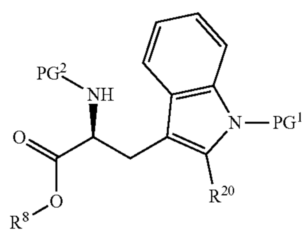

(IXb)

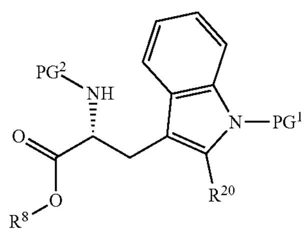

comprising:

asymmetric hydrogenation of a compound of formula (VIII), wherein $PG^1$ is a suitable protecting group for the indole nitrogen, $PG^2$ is a suitable amino protecting group and $R^8$ and $R^{20}$ are each independently $C_{1-6}$-alkyl, in the presence of a homogeneous catalyst (VIII)

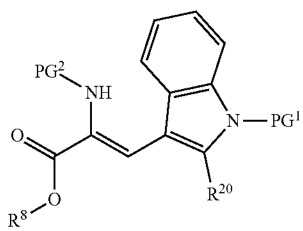

to afford said compound of formula (IXa) or (IXb).

In a further aspect, the present invention provides a compound of formula (I) described herein, obtainable by a process described herein.

In a further aspect, the present invention provides a pharmaceutical composition comprising a compound of formula (I) described herein or a pharmaceutically acceptable salt thereof and one or more pharmaceutically acceptable excipients.

In a further aspect, the present invention provides a compound of formula (I) described herein or a pharmaceutically acceptable salt thereof or a pharmaceutical composition described herein for use as therapeutically active substance.

In a further aspect, the present invention provides a compound of formula (I) described herein or a pharmaceutically acceptable salt thereof or a pharmaceutical composition described herein for use as an antibiotic.

In a further aspect, the present invention provides a compound of formula (I) described herein or a pharmaceutically acceptable salt thereof or a pharmaceutical composition described herein for use in the treatment or prevention of infections and resulting diseases caused by *Acinetobacter baumannii.*

In a further aspect, the present invention provides a method for the treatment or prevention of infections and resulting diseases caused by *Acinetobacter baumannii*, which method comprises administering a compound of formula (I) described herein or a pharmaceutically acceptable salt thereof or a pharmaceutical composition described herein to a human being or an animal.

In a further aspect, the present invention provides the use of a compound of formula (I) described herein or a pharmaceutically acceptable salt thereof or a pharmaceutical composition described herein for the treatment or prevention of infections and resulting diseases caused by *Acinetobacter baumannii.*

In a further aspect, the present invention provides the use of a compound of formula (I) described herein or a pharmaceutically acceptable salt thereof or a pharmaceutical composition described herein for the manufacture of a medicament for the treatment or prevention of infections and resulting diseases caused by *Acinetobacter baumannii.*

DETAILED DESCRIPTION OF THE DISCLOSURE

Definitions

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

Features, integers, characteristics, compounds, chemical moieties or groups described in conjunction with a particular aspect, embodiment or example of the invention are to be understood to be applicable to any other aspect, embodiment or example described herein, unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

All publications, patent applications, patents, and other references mentioned herein are incorporated by reference in their entirety.

The nomenclature used in this Application is based on IUPAC systematic nomenclature, unless indicated otherwise.

OpenEye Lexichem version 1.2.0, PerkinElmer E-Notebook for Chemistry or Insight for Excel 2017 R2 were employed to generate IUPAC chemical names.

Any open valency appearing on a carbon, oxygen, sulfur or nitrogen atom in the structures herein indicates the presence of a hydrogen atom, unless indicated otherwise.

The term "moiety" refers to an atom or group of chemically bonded atoms that is attached to another atom or molecule by one or more chemical bonds thereby forming part of a molecule.

For example, the variables $R^1$, $R^2$ and $R^3$ of formula (I) refer to moieties that are attached to the core structure of formula (I) by a covalent bond.

When indicating the number of substituents, the term "one or more" refers to the range from one substituent to the highest possible number of substitution, i.e. replacement of one hydrogen atom up to replacement of all hydrogen atoms by substituents.

The term "optional" or "optionally" denotes that a subsequently described event or circumstance can but need not occur, and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen atom up to replacement of all hydrogen atoms by substituents.

The term "compound(s) of this invention" and "compound(s) of the present invention" refers to compounds as disclosed herein and stereoisomers, tautomers, solvates, and salts (e.g., pharmaceutically acceptable salts) thereof.

When the compounds of the invention are solids, it is understood by those skilled in the art that these compounds, and their solvates and salts, may exist in different solid forms, particularly different crystal forms, all of which are intended to be within the scope of the present invention and specified formulas.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, procaine, hydrabamine, choline, betaine, ethylenediamine, glucosamine, methylglucamine, purines, piperazine, piperidine, N-ethylpiperidine, and polyamine resins.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog. (Cahn et al. Angew. Chem. Inter. Edit. 1966, 5, 385; errata 511). The prefixes D and L or (+) and (−) are employed to designate the sign of rotation of plane-polarized light by the compound, with (−) or L designating that the compound is levorotatory. A compound prefixed with (+) or D is dextrorotatory.

The term "halo", "halogen", and "halide" are used interchangeably herein and denote fluoro, chloro, bromo, or iodo. Particular examples of halo are fluoro and chloro.

The term "cyano" refers to a group —CN (nitrile).

The term "carboxy" refers to a group —C(O)OH.

The term "alkyl" denotes a monovalent linear or branched saturated hydrocarbon group of 1 to 12 carbon atoms. In particular embodiments, alkyl has 1 to 6 carbon atoms, and in more particular embodiments 1 to 4 carbon atoms. Examples of alkyl include methyl, ethyl, propyl, isopropyl, n-butyl, iso-butyl, sec-butyl, or tert-butyl. Particular examples of alkyl are methyl, ethyl, isopropyl, n-butyl, sec-butyl and tert-butyl, most particularly methyl and ethyl.

The term "alkoxy" denotes a group of the formula —O—R', wherein R' is an alkyl group. Examples of alkoxy moieties include methoxy, ethoxy, isopropoxy, and tert-butoxy. A particular example of alkoxy is methoxy ($—OCH_3$).

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point.

Exemplary protecting groups are amino-protecting groups, carboxy-protecting groups or hydroxy-protecting groups.

The term "amino-protecting group" denotes groups intended to protect an amino group and includes benzyl, benzyloxycarbonyl (carbobenzyloxy, CBZ), Fmoc (9-Fluorenylmethyloxycarbonyl), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective groups in Organic Synthesis", 2nd ed., John Wiley & Sons, Inc., New York, NY, 1991, chapter 7; E. Haslam, "Protecting groups in Organic Chemistry", J. G. W. McOmie, Ed., Plenum Press, New York, NY, 1973, Chapter 5, and T. W. Greene, "Protective groups in Organic Synthesis", John Wiley and Sons, New York, NY, 1981. The term "protected amino group" refers to an amino group substituted by an amino-protecting groups.

The term "protecting group for the indole nitrogen" denotes groups intended to protect the indole NH. Protecting groups for the indole nitrogen are commonly known in the art and largely overlap with amino-protecting groups as described herein. A particular, yet non-limiting example of a protecting group for the indole nitrogen is tert-butoxycarbonyl (BOC).

The term "carboxy-protecting group" denotes groups intended to protect a carboxy group and includes ester groups and heterocycloalkyl groups. Examples of such ester groups include substituted arylalkyl esters, including esters with substituted benzyls, such as 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydrol, esters with alkyl or substituted alkyl such as methyl, ethyl, t-butyl allyl or t-amyl, triphenylmethyl (trityl), 4-methoxytrityl, 4,4'-dimethoxytrityl, 4,4',4"-trimethoxytrityl, 2-phenylprop-2-yl, thioesters such as t-butyl thioester, silyl esters such as trimethylsilyl, t-butyldimethylsilyl esters, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, and 1-(trimethylsilylmethyl)prop-1-en-3-yl. Another example of carboxy-protecting groups are heterocycloalkyl groups such as 1,3-oxazolinyl. Further examples of these groups are found in T. W. Greene and P. G. M. Wuts, "Protective groups in Organic Synthesis", 2nd ed., John Wiley & Sons, Inc., New York, N.Y., 1991, chapter 5; E. Haslam, "Protecting groups in Organic Chemistry", J. G. W. McOmie, Ed., Plenum Press, New York, N.Y., 1973, Chapter 5, and T. W. Greene, "Protective groups in Organic Synthesis", John Wiley and Sons, New York, NY, 1981, Chapter 5. The term "protected carboxy group" denotes a carboxy group substituted by a carboxy-protecting group.

The term "hydroxy-protecting group" denotes groups intended to protect a hydroxy group and include ester- and ether-forming groups, in particular tetrahydropyranyloxy, benzoyl, acetoxy, carbamoyloxy, benzyl, and silylethers (e.g. TBS, TBDPS) groups. Further examples of these groups are found in T. W. Greene and P. G. M. Wuts, "Protective groups in Organic Synthesis", 2nd ed., John Wiley & Sons, Inc., New York, NY, 1991, chapters 2-3; E. Haslam, "Protecting groups in Organic Chemistry", J. G. W. McOmie, Ed., Plenum Press, New York, NY, 1973, Chapter 5, and T. W. Greene, "Protective groups in Organic Synthesis", John Wiley and Sons, New York, NY, 1981. The term "protected hydroxy group" refers to a hydroxy group substituted by a hydroxy-protecting group.

The term "deprotection" or "deprotecting" denotes the process by which a protecting group is removed after the selective reaction is completed. Deprotecting reagents include acids, bases or hydrogen, in particular potassium or sodium carbonates, lithium hydroxide in alcoholic solutions, zinc in methanol, acetic acid, trifluoroacetic acid, palladium catalysts, or boron tribromide.

The term "coupling reagent" refers to a reagent that is used in peptide synthesis to facilitate amide bond formations. Coupling reagents for use in peptide synthesis are well-known in the art. Some non-limiting examples of coupling reagents are 2-chloro-1-methylpyridinium iodide (Mukaiyama's reagent), carbodiimides such as dicyclohexylcarbodiimide (DCC), diisopropylcarbodiimide (DIC) and 1-Ethyl-3-(3-dimethylaminopropyl)carbodiimide (EDC) and aminium/uronium and phosphonium salts, such as O-(7-azabenzotriazol-1-yl)-N,N,N',N'-tetramethyluronium-hexafluorophosphate (HATU), 2-(1H-benzotriazol-1-yl)-1,1,3,3-tetramethyluronium hexafluorophosphate (HBTU), 2-(1H-Benzotriazole-1-yl)-1,1,3,3-tetramethylaminium tetrafluoroborate (TBTU), O-(1H-6-Chlorobenzotriazole-1-yl)-1,1,3,3-tetramethyluronium hexafluorophosphate (HCTU), benzotriazol-1-yl-oxytripyrrolidinophosphonium hexafluorophosphate (PyBOP) and (7-Azabenzotriazol-1-yloxy)tripyrrolidinophosphonium hexafluorophosphate (PyAOP). Particular examples of coupling reagents are Mukaiyama's reagent and HATU.

The term "resin" refers to a solid support for peptide synthesis that consists of a polymeric matrix functionalized with reactive "linker" groups (such as amino or hydroxyl groups), onto which peptide chains can be built. Resins for solid phase peptide synthesis are well-known in the art. A non-limiting example of a suitable polymeric matrix is poly(styrene-co-divinylbenzene), also known as polystyrene crosslinked with divinylbenzene, styrene divinylbenzene or styrene-DVB copolymer (100-200 mesh). Non-limiting examples of linker groups are 2-chloro-tritylchloride, amino and hydroxy groups.

The term "active pharmaceutical ingredient" (or "API") denotes the compound or molecule in a pharmaceutical composition that has a particular biological activity.

The terms "pharmaceutical composition" and "pharmaceutical formulation" (or "formulation") are used interchangeably and denote a mixture or solution comprising a therapeutically effective amount of an active pharmaceutical ingredient together with pharmaceutically acceptable excipients to be administered to a mammal, e.g., a human in need thereof.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "treating" or "treatment" of a disease state includes inhibiting the disease state, i.e., arresting the development of the disease state or its clinical symptoms, or relieving the disease state, i.e., causing temporary or permanent regression of the disease state or its clinical symptoms.

The term "preventing" or "prevention" of a disease state denotes causing the clinical symptoms of the disease state not to develop in a subject that can be exposed to or predisposed to the disease state, but does not yet experience or display symptoms of the disease state.

The term "amino acid" as used herein denotes an organic molecule possessing an amino moiety located at α-position to a carboxylic group. Examples of amino acids include: arginine, glycine, ornithine, 2,4-diaminobutyric acid, lysine, histidine, glutamic acid, aspartic acid, isoleucine, leucine, alanine, phenylalanine, tyrosine, tryptophan, methionine, serine and proline. The amino acid employed is optionally in each case the L-form.

The term "base" refers to any base which is appropriate for the outlined reaction step. Some particular, yet non-limiting examples of bases that may be used in the processes of the present invention are diisopropylethylamine, sodium carbonate, potassium phosphate, lithium hydroxide, sodium hydroxide and potassium hydroxide. For coupling reactions between carboxylic acids and amines bases like diisopropylethylamine are preferred. For hydrolyzing carboxylic acid esters, alkaline metal hydroxides like lithium hydroxide, sodium hydroxide and potassium hydroxide are preferred bases. For transition-metal catalyzed cross-coupling reactions like Suzuki-Miyaura couplings, bases like sodium carbonate and potassium phosphate are preferred.

The term "homogeneous catalyst" refers to a catalyst that is in the same phase as the reactants. In particular, a homogeneous catalyst is a catalyst that is soluble in the solvent where the reaction takes place. An example of a homogenous catalyst is [(1,2,5,6-η)-1,5-cyclooctadiene][(2S,2'S,5S,5'S)-1,1'-(1,2-phenylene)bis[2,5-diethylphospholane-κ-P]]-rhodium(1+) trifluoromethanesulfonate (CAS-RN 142184-30-3).

The term asymmetric hydrogenation refers to a chemical reaction that adds two atoms of hydrogen preferentially to one of two faces of an unsaturated substrate molecule, such as an alkene.

Compounds of the Invention

In a first aspect, the present invention provides a compound of formula (I)

(I)

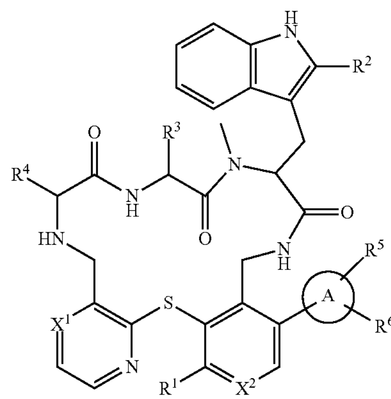

or a pharmaceutically acceptable salt thereof, wherein:

$X^1$ is CH or N;

$X^2$ is CH or N;

A is selected from:

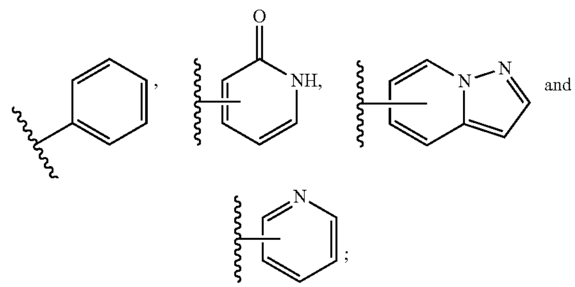

, , and ;

$R^1$ is selected from hydrogen, halogen, $C_{1-6}$-alkoxy and $C_{1-6}$-alkyl;

$R^2$ is hydrogen or $C_{1-6}$-alkyl;

$R^3$ is $C_{1-6}$-aminoalkyl;

$R^4$ is $C_{1-6}$-aminoalkyl or carbamoyl-$C_{1-6}$-alkyl;

$R^5$ is selected from carboxy, carboxy-$C_{1-6}$-alkyl and carboxy-$C_{2-6}$-alkenyl; and $R^6$ is selected from hydrogen, halogen, hydroxy, $C_{1-6}$-alkoxy and $C_{1-6}$-alkylsulfonyl; provided that said compound of formula (I) is not:

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-22-yl]-benzoic acid.

It is to be understood that every embodiment relating to a specific $X^1$, $X^2$, $R^1$ to $R^6$ and A as disclosed herein may be combined with any other embodiment relating to another $X^1$, $X^2$, $R^1$ to $R^6$ and A as disclosed herein.

In one embodiment, the present invention provides a compound of formula (I) as described herein, or a pharmaceutically acceptable salt thereof, wherein $X^1$ is CH.

In one embodiment, the present invention provides a compound of formula (I) as described herein, or a pharmaceutically acceptable salt thereof, wherein $X^1$ is N.

In one embodiment, the present invention provides a compound of formula (I) as described herein, or a pharmaceutically acceptable salt thereof, wherein A is selected from:

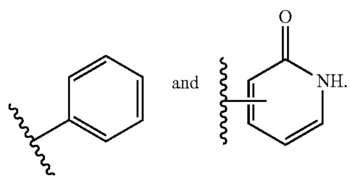

In one embodiment, the present invention provides a compound of formula (I) as described herein, or a pharmaceutically acceptable salt thereof, wherein A is selected from:

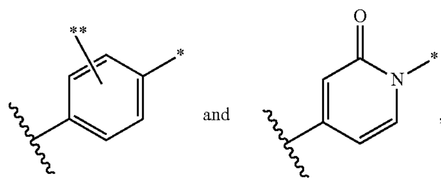

wherein:

the wavy line indicates the point of attachment to the rest of formula (I);

* indicates the point of attachment of $R^5$; and

** indicates the point of attachment of $R^6$.

In one embodiment, the present invention provides a compound of formula (I) as described herein, or a pharmaceutically acceptable salt thereof, wherein:

A is selected from: and

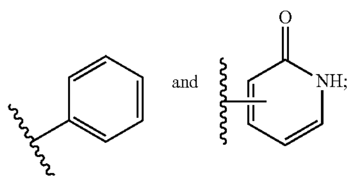

$R^5$ is selected from carboxy and carboxymethyl; and $R^6$ is hydrogen.

In a preferred embodiment, the present invention provides a compound of formula (I) as described herein, or a pharmaceutically acceptable salt thereof, wherein A is phenyl.

In one embodiment, the present invention provides a compound of formula (I) as described herein, or a pharmaceutically acceptable salt thereof, wherein $R^1$ is selected from hydrogen and halogen.

In a preferred embodiment, the present invention provides a compound of formula (I) as described herein, or a pharmaceutically acceptable salt thereof, wherein $R^1$ is selected from hydrogen and chloro.

In one embodiment, the present invention provides a compound of formula (I) as described herein, or a pharmaceutically acceptable salt thereof, wherein $R^1$ is selected from hydrogen, chloro, fluoro, methyl and methoxy.

In a particularly preferred embodiment, the present invention provides a compound of formula (I) as described herein, or a pharmaceutically acceptable salt thereof, wherein $R^1$ is hydrogen.

In one embodiment, the present invention provides a compound of formula (I) as described herein, or a pharmaceutically acceptable salt thereof, wherein $R^2$ is hydrogen or methyl.

In a preferred embodiment, the present invention provides a compound of formula (I) as described herein, or a pharmaceutically acceptable salt thereof, wherein $R^2$ is hydrogen.

In a preferred embodiment, the present invention provides a compound of formula (I) as described herein, or a pharmaceutically acceptable salt thereof, wherein $R^3$ is $C_{2-4}$-aminoalkyl.

In a preferred embodiment, the present invention provides a compound of formula (I) as described herein, or a pharmaceutically acceptable salt thereof, wherein $R^3$ is $C_4$-aminoalkyl.

In a particularly preferred embodiment, the present invention provides a compound of formula (I) as described herein, or a pharmaceutically acceptable salt thereof, wherein $R^3$ is 4-aminobutyl.

In one embodiment, the present invention provides a compound of formula (I) as described herein, or a pharmaceutically acceptable salt thereof, wherein $R^3$ is selected from 2-aminoethyl, 3-aminopropyl and 4-aminobutyl.

In one embodiment, the present invention provides a compound of formula (I) as described herein, or a pharmaceutically acceptable salt thereof, wherein $R^4$ is $C_{1-6}$-aminoalkyl.

In one embodiment, the present invention provides a compound of formula (I) as described herein, or a pharmaceutically acceptable salt thereof, wherein $R^4$ is $C_{2-3}$-aminoalkyl.

In a preferred embodiment, the present invention provides a compound of formula (I) as described herein, or a pharmaceutically acceptable salt thereof, wherein $R^4$ is $C_3$-aminoalkyl.

In a particularly preferred embodiment, the present invention provides a compound of formula (I) as described herein, or a pharmaceutically acceptable salt thereof, wherein $R^4$ is 3-aminopropyl.

In one embodiment, the present invention provides a compound of formula (I) as described herein, or a pharmaceutically acceptable salt thereof, wherein $R^4$ is selected from 2-aminoethyl, 3-aminopropyl and 3-amino-3-oxo-propyl.

In one embodiment, the present invention provides a compound of formula (I) as described herein, or a pharmaceutically acceptable salt thereof, wherein $R^5$ is selected from carboxy, carboxymethyl and (Z)-2-carboxyvinyl.

In a preferred embodiment, the present invention provides a compound of formula (I) as described herein, or a pharmaceutically acceptable salt thereof, wherein $R^5$ is carboxy or carboxymethyl.

In a preferred embodiment, the present invention provides a compound of formula (I) as described herein, or a pharmaceutically acceptable salt thereof, wherein $R^5$ is carboxy.

In a preferred embodiment, the present invention provides a compound of formula (I) as described herein, or a pharmaceutically acceptable salt thereof, wherein $R^5$ is carboxymethyl.

In a preferred embodiment, the present invention provides a compound of formula (I) as described herein, or a pharmaceutically acceptable salt thereof, wherein $R^6$ is hydrogen.

In one embodiment, the present invention provides a compound of formula (I) as described herein, or a pharmaceutically acceptable salt thereof, wherein $R^6$ is selected from hydrogen, chloro, fluoro, hydroxy, methoxy and methylsulfonyl.

In one embodiment, the present invention provides a compound of formula (I) as described herein, or a pharmaceutically acceptable salt thereof, wherein:

$X^1$ is CH;

$X^2$ is CH or N;

A is selected from:

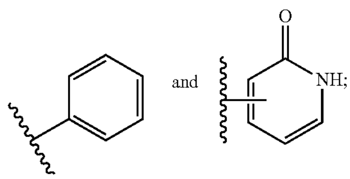

$R^1$ is hydrogen or halogen;

$R^2$ is hydrogen;

$R^3$ is $C_{2-4}$-aminoalkyl;

$R^4$ is $C_{2-3}$-aminoalkyl;

$R^5$ is carboxy or carboxy-$C_{1-6}$-alkyl; and $R^6$ is hydrogen.

In a preferred embodiment, the present invention provides a compound of formula (I) as described herein, or a pharmaceutically acceptable salt thereof, wherein:

$X^1$ is CH;

$X^2$ is CH or N;

A is selected from:

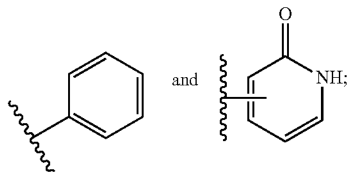

$R^1$ is hydrogen or halogen;

$R^2$ is hydrogen;

$R^3$ is $C_4$-aminoalkyl;

$R^4$ is $C_3$-aminoalkyl;

$R^5$ is carboxy or carboxy-$C_{1-6}$-alkyl; and $R^6$ is hydrogen.

In a particularly preferred embodiment, the present invention provides a compound of formula (I) as described herein, or a pharmaceutically acceptable salt thereof, wherein:

$X^1$ is CH;

$X^2$ is CH or N;

A is selected from:

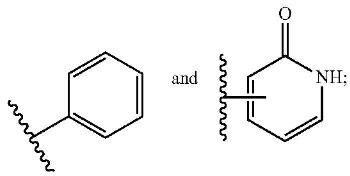

$R^1$ is hydrogen or chloro;

$R^2$ is hydrogen;

$R^3$ is 4-aminobutyl.

$R^4$ is 3-aminopropyl;

$R^5$ is carboxy or carboxymethyl; and $R^6$ is hydrogen.

In one embodiment, the present invention provides a compound of formula (I) as described herein, or a pharmaceutically acceptable salt thereof, wherein:

$X^1$ is CH or N;

$X^2$ is CH or N;

A is selected from:

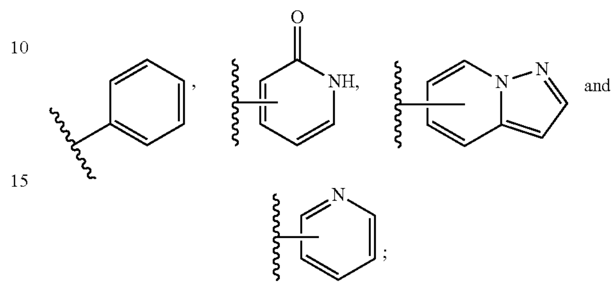

$R^1$ is selected from hydrogen, chloro, fluoro, methyl and methoxy;

$R^2$ is hydrogen or methyl;

$R^3$ is selected from 2-aminoethyl, 3-aminopropyl and 4-aminobutyl;

$R^4$ is selected from 2-aminoethyl, 3-aminopropyl and 3-amino-3-oxo-propyl;

$R^5$ is selected from carboxy, carboxymethyl and (Z)-2-carboxyvinyl; and $R^6$ is selected from hydrogen, chloro, fluoro, hydroxy, methoxy and methylsulfonyl.

In a preferred embodiment, the present invention provides a compound of formula (I) as described herein, or a pharmaceutically acceptable salt thereof, wherein the group

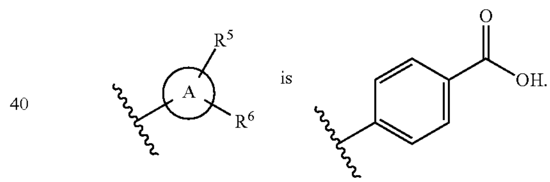

In a preferred embodiment, the present invention provides a compound of formula (I) as described herein, or a pharmaceutically acceptable salt thereof, selected from:

4-[(11S,14S,17S)-14-(4-aminobutyl)-11-(3-amino-3-oxo-propyl)-25-chloro-17-(1H-indol-3-ylmethyl)-16-methyl-12,15,18-trioxo-2-thia-4,10,13,16,19-pentazatricyclo [19.4.0.03,8]pentacosa-1(21),3,5,7,22,24-hexaen-22-yl] benzoic acid;

4-[(11S,14S,17S)-14-(4-aminobutyl)-11-(3-aminopropyl)-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid;

4-[(11S,14S,17S)-14-(4-aminobutyl)-11-(3-aminopropyl)-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid;

4-[(11S,14S,17S)-14-(4-aminobutyl)-11-(3-aminopropyl)-25-chloro-17-(1H-indol-3-ylmethyl)-16-methyl-12,15,18-trioxo-2-thia-4,7,10,13,16,19-hexazatricyclo [19.4.0.03,8]pentacosa-1(21),3,5,7,22,24-hexaen-22-yl] benzoic acid;

2-chloro-4-[rac-(11S,14S,17S)-14-(4-aminobutyl)-11-(3-aminopropyl)-25-chloro-17-(1H-indol-3-ylmethyl)-16- methyl-12,15,18-trioxo-2-thia-4,7,10,13,16,19-hexazatricyclo[19.4.0.03,8]pentacosa-1(21),3,5,7,22,24-hexaen-22-yl]benzoic acid;

4-[(11S,14S,17S)-14-(4-aminobutyl)-11-(3-aminopropyl)-25-chloro-17-(1H-indol-3-ylmethyl)-16-methyl-12,15,18-trioxo-2-thia-4,7,10,13,16,19-hexazatricyclo[19.4.0.03,8]pentacosa-1(21),3,5,7,22,24-hexaen-22-yl]-2-fluoro-benzoic acid;

4-[(11S,14S,17S)-14-(4-aminobutyl)-11-(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid;

4-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]-2-methylsulfonyl-benzoic acid;

4-[(11S,14S,17S)-14-(4-amino-3,3-difluoro-butyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(21),3,5,7,22,24-hexaen-22-yl]benzoic acid;

4-[(11S,14S,17S)-14-(4-aminobutyl)-11-(3-aminopropyl)-25-chloro-16-methyl-17-[(2-methyl-1H-indol-3-yl)methyl]-12,15,18-trioxo-2-thia-4,10,13,16,19-pentazatricyclo[19.4.0.03,8]pentacosa-1(25),3,5,7,21,23-hexaen-22-yl]benzoic acid;

4-[(11S,14S,17S)-14-(4-aminobutyl)-11-(3-aminopropyl)-25-chloro-16-methyl-17-[(2-methyl-1H-indol-3-yl)methyl]-12,15,18-trioxo-2-thia-4,10,13,16,19-pentazatricyclo[19.4.0.03,8]pentacosa-1(25),3,5,7,21,23-hexaen-22-yl]benzoic acid;

5-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(25),3,5,7,21,23-hexaen-22-yl]pyridine-2-carboxylic acid;

4-[(11S,14S,17S)-11,14-bis(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(21),3,5,7,22,24-hexaen-22-yl]benzoic acid;

4-[(11S,14S,17S)-11,14-bis(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid;

4-[(11S,14S,17S)-14-(4-aminobutyl)-11-(3-aminopropyl)-16-methyl-17-[(2-methyl-1H-indol-3-yl)methyl]-12,15,18-trioxo-2-thia-4,10,13,16,19-pentazatricyclo[19.4.0.03,8]pentacosa-1(25),3,5,7,21,23-hexaen-22-yl]benzoic acid;

4-[(11S,14S,17S)-14-(4-aminobutyl)-11-(3-aminopropyl)-17-(1H-indol-3-ylmethyl)-16,25-dimethyl-12,15,18-trioxo-2-thia-4,10,13,16,19-pentazatricyclo[19.4.0.03,8]pentacosa-1(25),3(8),4,6,21,23-hexaen-22-yl]benzoic acid;

4-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(21),3(8),4,6,22,24-hexaen-22-yl]-2-hydroxy-benzoic acid;

4-[(11S,14S,17S)-14-(2-aminoethyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid;

2-methoxy-4-[rac-(11S,14S,17S)-14-(4-aminobutyl)-11-(3-aminopropyl)-25-chloro-17-(1H-indol-3-ylmethyl)-16-methyl-12,15,18-trioxo-2-thia-4,7,10,13,16,19-hexazatricyclo[19.4.0.03,8]pentacosa-1(25),3(8),4,6,21,23-hexaen-22-yl]benzoic acid;

2-[4-[(11S,14S,17S)-14-(4-aminobutyl)-11-(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]-2-oxo-1-pyridyl]acetic acid;

4-[(11S,14S,17S)-11,14-bis(3-aminopropyl)-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid;

4-[(11S,14S,17S)-14-(4-aminobutyl)-11-(3-aminopropyl)-17-(1H-indol-3-ylmethyl)-25-methoxy-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid;

5-[(11S,14S,17S)-11,14-bis(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]pyridine-2-carboxylic acid;

2-[4-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(21),3,5,7,22,24-hexaen-22-yl]-2-oxo-1-pyridyl]acetic acid;

4-[(11S,14S,17S)-14-(4-aminobutyl)-11-(2-aminoethyl)-25-chloro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid;

4-[(11S,14S,17S)-11-(2-aminoethyl)-14-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid;

2-[4-[(11S,14S,17S)-14-(4-aminobutyl)-11-(3-aminopropyl)-17-(1H-indol-3-ylmethyl)-16,25-dimethyl-12,15,18-trioxo-2-thia-4,10,13,16,19-pentazatricyclo[19.4.0.03,8]pentacosa-1(25),3(8),4,6,21,23-hexaen-22-yl]-2-oxo-1-pyridyl]acetic acid;

4-[(11S,14S,17S)-14-(4-aminobutyl)-11-(3-aminopropyl)-17-(1H-indol-3-ylmethyl)-16-methyl-12,15,18-trioxo-2-thia-4,10,13,16,19,24-hexazatricyclo[19.4.0.03,8]pentacosa-1(25),3(8),4,6,21,23-hexaen-22-yl]benzoic acid;

2-[4-[(11S,14S,17S)-14-(4-aminobutyl)-11-(3-aminopropyl)-25-chloro-16-methyl-17-[(2-methyl-1H-indol-3-yl)methyl]-12,15,18-trioxo-2-thia-4,10,13,16,19-pentazatricyclo[19.4.0.03,8]pentacosa-1(25),3(8),4,6,21,23-hexaen-22-yl]-2-oxo-1-pyridyl]acetic acid;

(E)-3-[4-[(11S,14S,17S)-14-(4-aminobutyl)-11-(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]-2-oxo-1-pyridyl]prop-2-enoic acid; and 5-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]pyrazolo[1,5-a]pyridine-2-carboxylic acid;

or a pharmaceutically acceptable salt thereof.

In a particularly preferred embodiment, the present invention provides a compound of formula (I) as described herein, or a pharmaceutically acceptable salt thereof, selected from:

4-[(11S,14S,17S)-14-(4-aminobutyl)-11-(3-aminopropyl)-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid;

2-[4-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(21),3,5,7,22,24-hexaen-22-yl]-2-oxo-1-pyridyl]acetic acid; and 4-[(11S,14S,17S)-14-(4-aminobutyl)-11-(3-aminopropyl)-17-(1H-indol-3-ylmethyl)-16-methyl-12,15,18-trioxo-2-thia-4,10,13,16,19,24-hexazatricyclo[19.4.0.03,8]pentacosa-1(25),3(8),4,6,21,23-hexaen-22-yl]benzoic acid;

or a pharmaceutically acceptable salt thereof.

In one embodiment, the present invention provides pharmaceutically acceptable salts of the compounds according to formula (I) as described herein, especially hydrochloride salts. In a further particular embodiment, the present invention provides compounds according to formula (I) as described herein.

Manufacturing Processes

The compounds of the present invention can be prepared by any conventional means. Suitable processes for synthesizing these compounds as well as their starting materials are provided in the schemes below and in the examples. All substituents, in particular, $X^1$, $X^2$, $R^1$ to $R^4$ and A are as defined above unless otherwise indicated. Furthermore, and unless explicitly otherwise stated, all reactions, reaction conditions, abbreviations and symbols have the meanings well known to a person of ordinary skill in organic chemistry.

1. General Synthesis of the Tether

The tether intermediate of formula (III) can be prepared following standard methods known in the art, particularly according to methods as described in the examples.

(III)

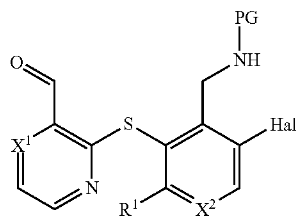

In compound (III), PG is a suitable amino protecting group, such as 9-fluorenylmethoxycarbonyl, Hal is a halogen, preferably Br or I, and $X^1$, $X^2$ and $R^1$ are as defined herein.

2. General Synthesis of the Tripeptide

The tripeptide of formula (IV), wherein $R^{30}$ is —$C_{1-6}$-alkyl-NH—COO$^t$Bu; $R^{40}$ is —$C_{1-6}$-alkyl-NH—COO$^t$Bu or —$C_{1-6}$-alkyl-C(O)—NH—$CPh_3$ and $R^2$ is as defined herein, can be prepared following standard methods known in the art.

(IV)

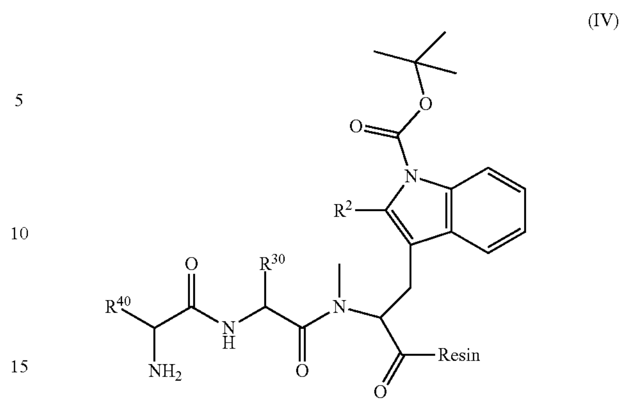

The tripeptide sequence (IV) can for example be synthesized via state-of-the-art solid-phase peptide synthesis protocols as follows:

a) A resin (e.g. 2-chloro-trityl resin) as solid support is loaded with the first N-protected amino acid and diisopropylethylamine (N,N-diisopropylethylamine or N,N-diisopropylethylamine) followed by cleavage of the protecting group.
b) A second N-protected amino acid is coupled with a coupling reagent and diisopropylethylamine followed by cleavage of the protecting group (e.g. 9-fluorenylmethoxycarbonyl).
c) A third N-protected amino acid is coupled with a coupling reagent and diisopropylethylamine followed by cleavage of the protecting group.

In a particular embodiment, the N-protected amino acids are protected with 9-fluorenylmethyloxycarbonyl.

In a particular embodiment, the resin is loaded in step a) with 0.1-1.0 equivalents of the first amino acid and excess diisopropylethylamine in dichloromethane.

In a particular embodiment, the resin is thoroughly washed after the coupling reaction in step a) with dimethylformamide (N,N-dimethylformamide) and dichloromethane (dichloromethane).

In a particular embodiment, the 9-fluorenylmethoxycarbonyl protecting group is cleaved off in step a) with a mixture of 50% piperidine in dichloromethane/N,N-dimethylformamide (1:1).

In a particular embodiment, the resin is thoroughly washed after the deprotection in step a) with N,N-dimethylformamide, dichloromethane and methanol followed by drying under vacuum and weighing.

In a particular embodiment, the coupling reagent in step b) is 2-chloro-1-methylpyridinium iodide.

In a particular embodiment, the second amino acid in step b) is coupled with 4 equivalents of 2-chloro-1-methylpyridinium iodide as coupling reagent and 6 equivalents of of diisopropylethylamine in N,N-dimethylformamide/dichloromethane (1:1).

In a particular embodiment, the resin is thoroughly washed after the coupling reaction in step b) with N,N-dimethylformamide and dichloromethane.

In a particular embodiment, the 9-fluorenylmethoxycarbonyl protecting group is cleaved off in step b) with a mixture of 50% piperidine in dichloromethane/N,N-dimethylformamide (1:1).

In a particular embodiment, the resin is thoroughly washed after the deprotection in step b) with N,N-dimethylformamide and dichloromethane followed by drying under vacuum and weighing.

In a particular embodiment, the coupling reagent in step c) is O-(7-azabenzotriazol-1-yl)-N,N,N',N'-tetramethyluronium-hexafluorophosphate.

In a particular embodiment, the third amino acid in step c) is coupled with 4 equivalents of O-(7-azabenzotriazol-1-yl)-N,N,N',N'-tetramethyluronium-hexafluorophosphate as coupling reagent and 6 equivalents of diisopropylethylamine in N,N-dimethylformamide/dichloromethane (1:1).

In a particular embodiment, the resin is thoroughly washed after the coupling reaction in step c) with N,N-dimethylformamide and dichloromethane.

In a particular embodiment, the 9-fluorenylmethoxycarbonyl protecting group is cleaved off in step c) with a mixture of 20% piperidine in N,N-dimethylformamide.

In a particular embodiment, the resin is thoroughly washed after the deprotection in step c) with N,N-dimethylformamide and dichloromethane followed by drying under vacuum and weighing.

3. General Procedure for the Coupling of the Tripeptide to the Tether

The intermediates of formula (V) can be obtained, for example starting from the compounds of formula (III) and of formula (IV) according to Scheme 1. Hal is a halogen, preferably Br or I, $R^{30}$ is —$C_{1-6}$-alkyl-NH—COO$^t$Bu; $R^{40}$ is —$C_{1-6}$-alkyl-NH—COO$^t$Bu or —$C_{1-6}$-alkyl-C(O)—NH—$CPh_3$, and $X^1$, $X^2$, $R^1$ and $R^2$ are as defined herein.

Scheme 1

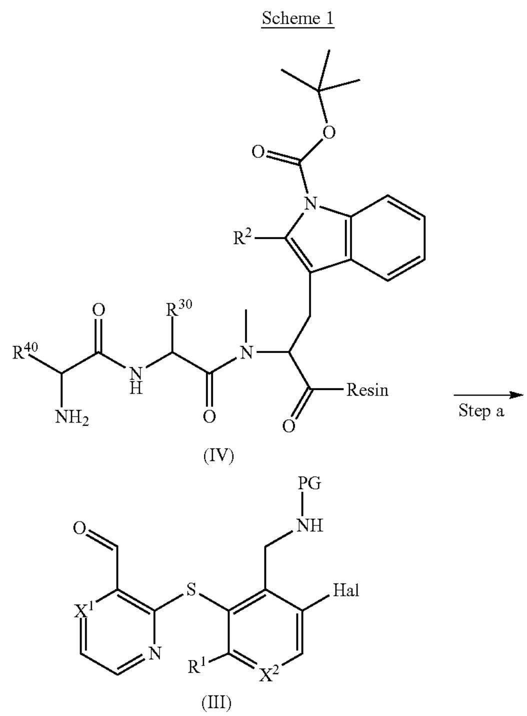

(IV)

(III)

-continued

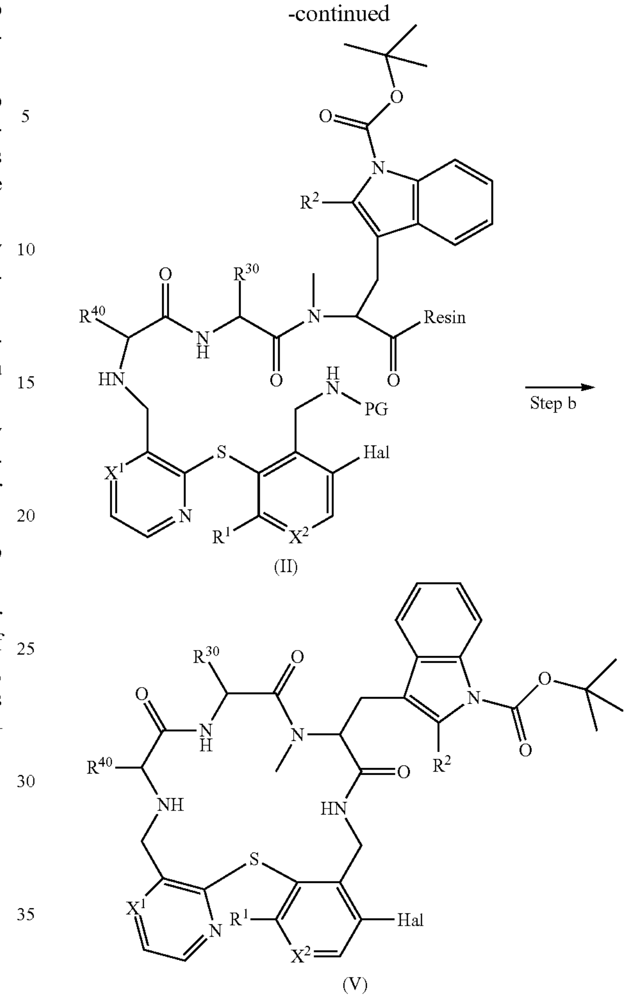

(II)

(V)

Coupling of the tether aldehyde of formula (III) with the tripeptide of formula (IV) (Scheme 1, step a) may be achieved, for example, by dissolving said tether aldehyde of formula (III) in a mixture of 1-methyl-2-pyrrolidone, trimethyl orthoformate and acetic acid and adding the resin comprising the tripeptide of formula (IV) to the solution. After agitation of the mixture, a reducing agent such as sodium cyanoborohydride is added to provide a compound of formula (II).

In Scheme 1, step b, the protecting group (PG) of the tether is cleaved off, e.g. with a mixture of 20% piperidine in N,N-dimethylformamide. The resin on the tripeptide can be cleaved e.g. by addition of 20% hexafluoroisopropanol in dichloromethane and filtered off. The intermediate of formula (V) is finally obtained through cyclisation of the cleaved compound of formula (II) using e.g. O-(7-azabenzotriazol-1-yl)-N,N,N',N'-tetramethyluronium-hexafluorophosphate and diisopropylethylamine.

4. General Procedure for the Installation of the Carboxylic Acid Subunit

The compounds of formula (I) can be obtained, for example starting from the compounds of formula (V) according to Scheme 2. Hal is a halogen, preferably Br or I; $R^{30}$ is —$C_{1-6}$-alkyl-NH—COO$^t$Bu; $R^{40}$ is —$C_{1-6}$-alkyl-NH—COO$^t$Bu or —$C_{1-6}$-alkyl-C(O)—NH—$CPh_3$, and A, $X^1$, $X^2$, $R^1$, and $R^2$ are as defined herein.

Scheme 2

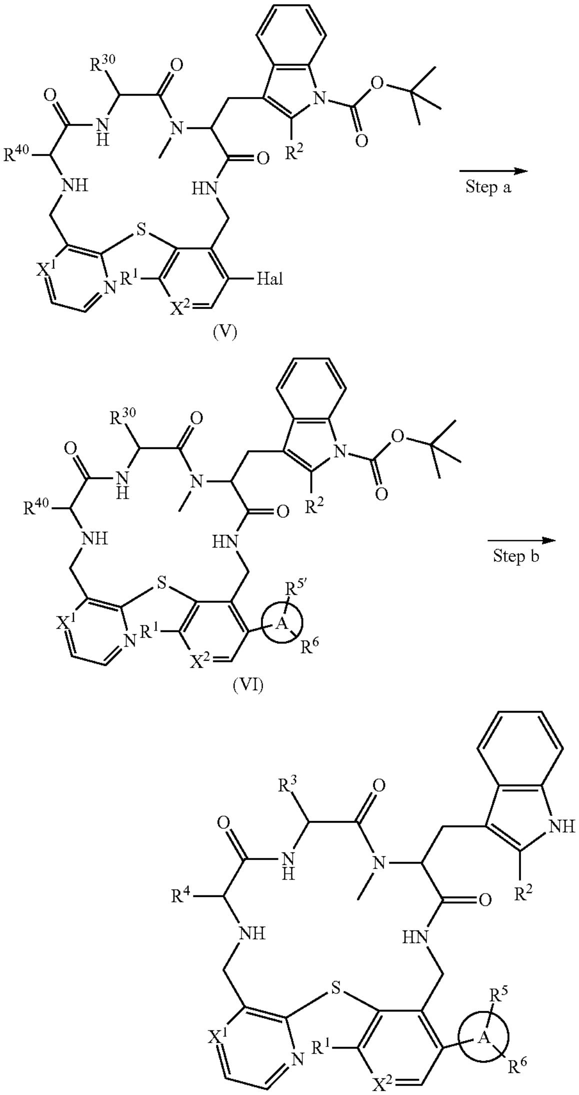

(V)

(VI)

(I)

In step a, scheme 2, halo-macrocycle (V) is reacted with boronic acid (VIIA) or dioxoborolane (VIIB) to produce compounds of formula (VI), wherein $R^{30}$ is —$C_{1-6}$-alkyl-NH—COO$^t$Bu; $R^{40}$ is —$C_{1-6}$-alkyl-NH—COO$^t$Bu or —$C_{1-6}$-alkyl-C(O)—NH—$CPh_3$; A, $X^1$, $X^2$, $R^1$, $R^2$ and $R^6$ are as defined herein and $R^{5'}$ is selected from $R^7$, —$C_{1-6}$-alkyl-$R^7$ and $C_{2-6}$-alkenyl-$R^7$, wherein $R^7$ is selected from carboxy and a protected carboxylic acid. Particular, yet non-limiting examples of protected carboxylic acids are alkyl and aryl-alkyl esters, such as methyl ester and tert-butyl ester.

(VIIA)

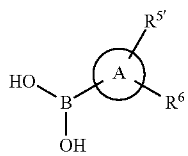

-continued (VIIB)

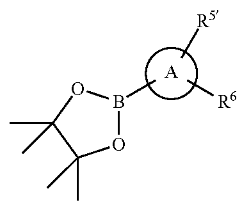

The reaction is performed in the presence of a suitable palladium catalyst, e. g., tetrakis(triphenylphosphine)palladium(0) or [1,1'-bis(diphenylphosphino)ferrocene]-dichloropalladium(II), in a solvent such as water, 1,4-dioxane, N,N-dimethylacetamide, tetrahydrofuran, 2-methyltetrahydrofuran or mixtures thereof, in the presence of a base, e. g., sodium carbonate or potassium phosphate, at temperatures between 20° C. and 150° C., optionally under microwave irradiation.

In step b, scheme 2, the protecting groups are cleaved using methods and reagents known in the art. For instance, a global deprotection can be performed using trifluoroacetic acid in dichloromethane, followed by evaporation of the solvent and hydrolysis in water or aqueous hydrochloric acid at room temperature. By this sequence, for example the following protecting groups may be removed:

a tert-butoxycarbonyl group in $R^{30}$ a tert-butoxycarbonyl group or a trityl group in $R^{40}$, a tert-butoxycarbonyl group at the indole subunit a tert-butyl ester at $R^{5'}$ In a particular embodiment, where $R^{5'}$ of the boron reagent (VIIA) or (VIIB) used in step a is a methyl ester, intermediate (VI) is first hydrolysed with a base, e. g., sodium hydroxide, in a suitable solvent mixture, e. g., water/tetrahydrofuran or water/ethanol, at temperatures between 20° C. and 100° C. This procedure also cleaves the tert-butoxycarbonyl group from the indole nitrogen. In a second step, the remaining protecting groups are cleaved using hydrochloric acid in a suitable solvent mixture, e. g., water/tetrahydrofuran, at temperatures between 0° C. and 50° C. By this sequence of deprotection reactions compounds of formula (I) are produced.

Accordingly, in one aspect, the present invention provides a process for the manufacture of the compounds of formula (I) described herein, comprising:

b) cleaving all amino-, indole- and carboxy protecting groups present in a compound of formula (VI), wherein $R^1$, $R^2$, $R^{5'}$, $R^6$, $R^{30}$, $R^{40}$, $X^1$ and $X^2$ are as defined herein, (VI)

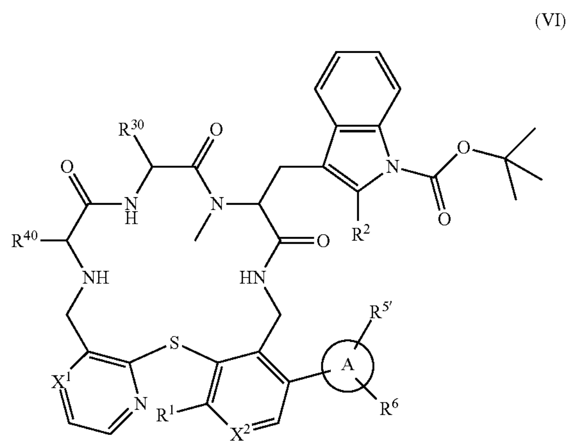

to afford said compound of formula (I).

In one embodiment of the process according to the invention, $R^{5'}$ is selected from $R^7$, $—C_{1-6}$-alkyl-$R^7$ and $—C_{2-6}$-alkenyl-$R^7$, wherein $R^7$ is selected from carboxy and a protected carboxylic acid.

In a preferred embodiment of the process according to the invention, $R^{5'}$ is selected from $R^7$, $—C_{1-6}$-alkyl-$R^7$ and $—C_{2-6}$-alkenyl-$R^7$, wherein $R^7$ is selected from carboxy and a protected carboxylic acid, wherein said protected carboxylic acid is an alkyl- or arylalkyl ester.

In a particularly preferred embodiment of the process according to the invention, $R^{5'}$ is selected from $R^7$, $—C_{1-6}$-alkyl-$R^7$ and $—C_{2-6}$-alkenyl-$R^7$, wherein $R^7$ is selected from carboxy and a protected carboxylic acid, wherein said protected carboxylic acid is a methyl ester or a tert-butyl ester.

In one embodiment of the process according to the invention, said compound of formula (VI) is obtained by:

c) reacting a halo macrocycle of formula (V), wherein $R^1$, $R^2$, $R^{30}$, $R^4$, $X^1$ and $X^2$ are as defined herein, (V)

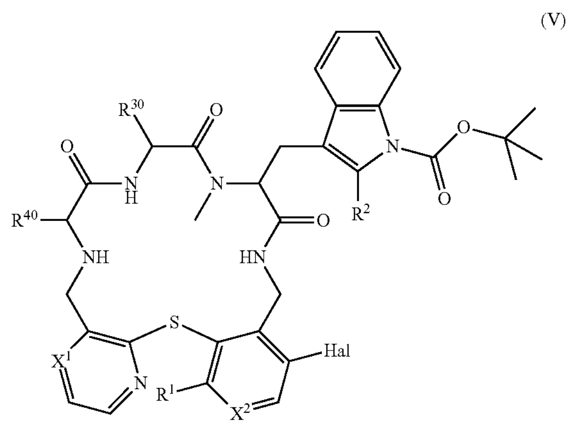

with a boronic acid (VIIA)

(VIIA)

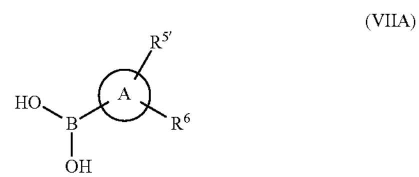

or a dioxoborolane (VIIB), wherein $R^{5'}$ and $R^6$ are as defined herein (VIIB)

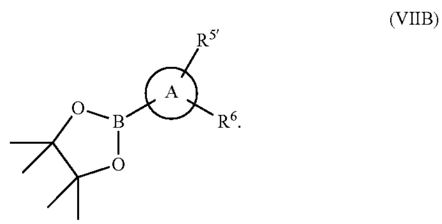

In one embodiment of the process according to the invention, said halo macrocycle of formula (V) is obtained by:

d) cyclisation of a compound of formula (IIa), wherein $R^1$, $R^2$, $R^{30}$, $R^{40}$, $X^1$ and $X^2$ are as defined herein, using a coupling reagent in the presence of a base (IIa)

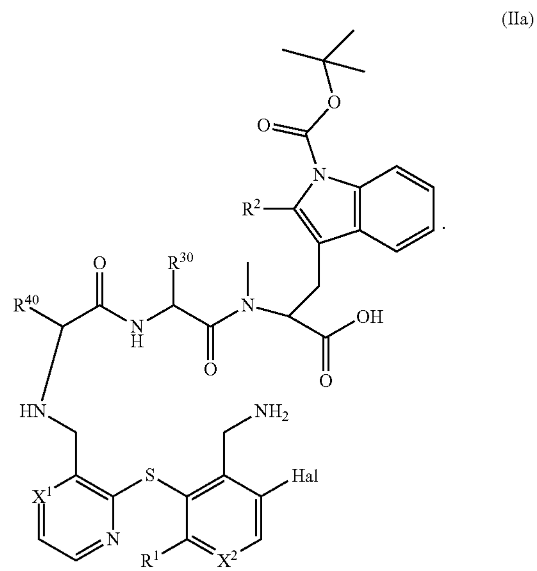

In one embodiment of the process according to the invention, said compound of formula (IIa) is obtained by:

(II)

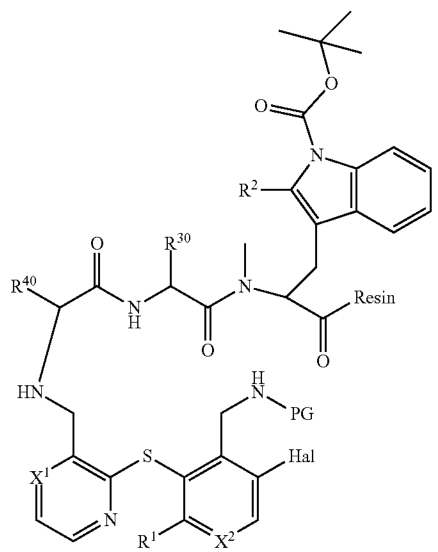

e) removal of the protecting group (PG) and the resin from a compound of formula (II), wherein $R^1$, $R^2$, $R^{30}$, $R^{40}$, $X^1$, $X^2$ and PG are as defined herein In one embodiment of the process according to the invention, said compound of formula (II) is obtained by:

f) reductive amination of an aldehyde of formula (III), wherein $X^1$, $X^2$, $R^1$ and PG are as defined herein, (III)

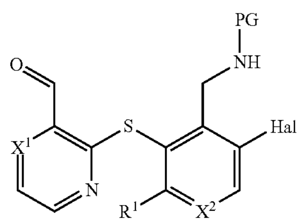

with an amine of formula (IV), wherein $R^2$, $R^{30}$ and $R^{40}$ are as defined herein (IV)

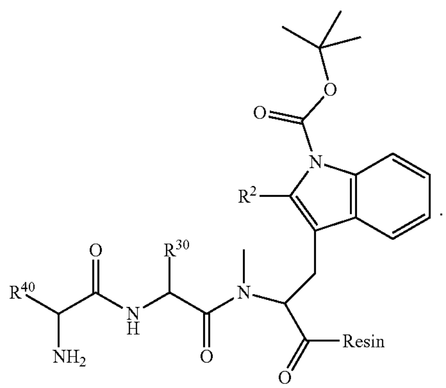

In a particularly preferred embodiment, the present invention provides a process for the manufacture of the compounds of formula (I) described herein, comprising:

a) reductive amination of a compound of formula (III), wherein $X^1$, $X^2$, $R^1$ and PG are as defined herein, with a compound of formula (IV), wherein $R^2$, $R^{30}$ and $R^{40}$ are as defined herein, to provide a compound of formula (II), wherein $R^1$, $R^2$, $R^{30}$, $R^{40}$, $X^1$, $X^2$ and PG are as defined herein;

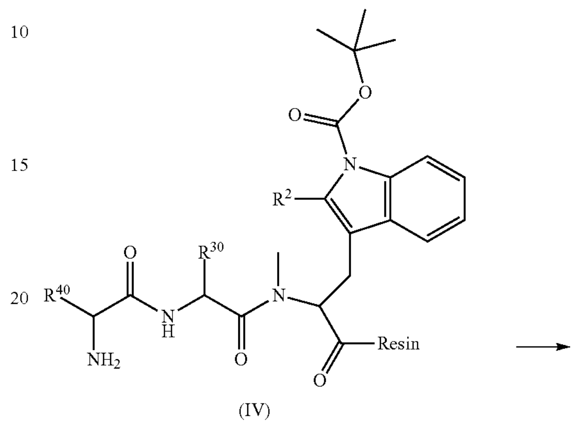

(IV)

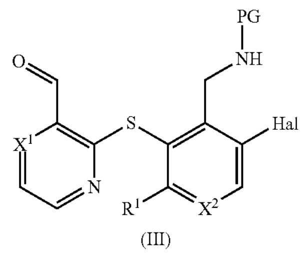

(III)

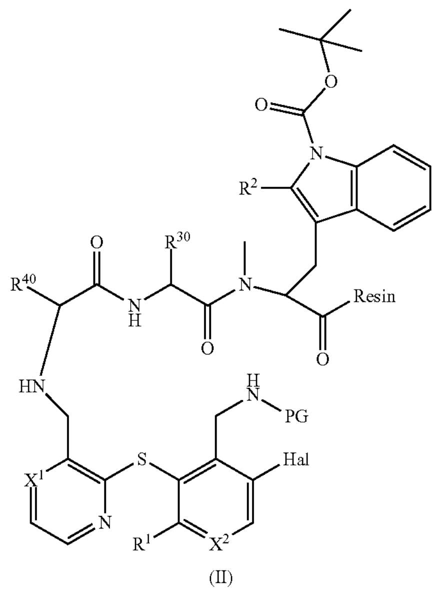

(II)

b) removal of the protecting group (PG) and the resin from the compound of formula (II) to provide a compound of formula (IIa), wherein $R^1$, $R^2$, $R^{30}$, $R^{40}$, $X^1$ and $X^2$ are as defined herein;

(IIa)

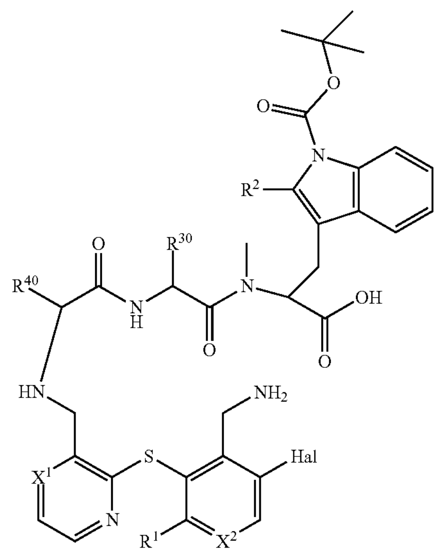

c) cyclisation of the compound of formula (IIa) using a coupling reagent in the presence of a base to afford a halo macrocycle of formula (V), wherein $R^1$, $R^2$, $R^{30}$, $R^{40}$, $X^1$ and $X^2$ are as defined herein;

(V)

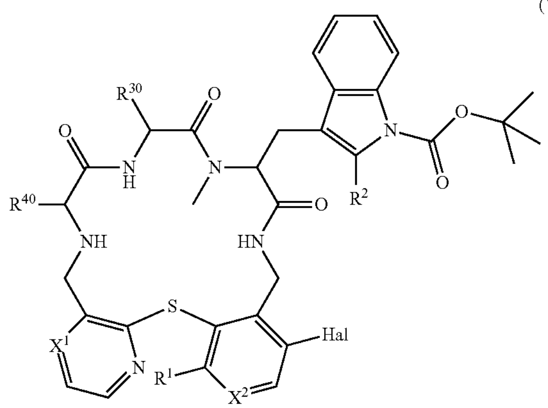

d) reacting said halo macrocycle of formula (V) with a boronic acid (VIIA)

(VIIA)

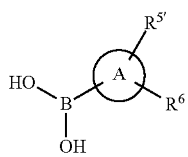

or a dioxoborolane (VIIB), wherein $R^{5'}$ and $R^6$ are as defined herein (VIIB)

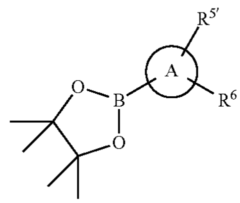

to afford a compound of formula (VI), wherein $R^1$, $R^2$, $R^{5'}$, $R^6$, $R^{30}$, $R^{40}$, $X^1$ and $X^2$ are as defined herein (VI)

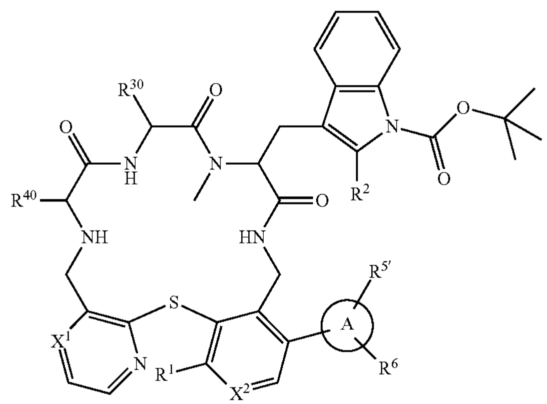

;

and e) cleaving all amino-, indole- and carboxy protecting groups present in compound of formula (VI) to afford said compound of formula (I).

Cleavage of protecting groups is generally accomplished using methods and reagents known in the art (exemplary protecting groups and their application in organic synthesis are described, for example, in "Protective groups in Organic Chemistry" by T. W. Greene and P. G. M. Wuts, 5th Ed., 2014, John Wiley & Sons, N.Y.).

In a particular embodiment, primary or secondary amines are produced from the tert-butylcarbamate derivates by reaction with a suitable acid, e. g., trifluoroacetic acid or hydrogen chloride, in solvents such as dichloromethane, water, 1,4-dioxane, 2-propanol, acetonitrile or mixtures thereof, optionally in the presence of a carbocation scavenger, e. g., triisopropylsilane or triethylsilane. Under these conditions, N-(tert-butoxycarbonyl)indoles, N-(trimethylphenyl)-amides, and O-tert-butyl-dimethylsilylethers are concomitantly converted to free indoles, amides, and alcohols, respectively.

In a particular embodiment, carboxylic acids are produced from their alkyl ester derivatives by saponification using a base such as lithium hydroxide, sodium hydroxide, or potassium hydroxide, in a solvent system such as water/ethanol or water/tetrahydrofuran.

The compounds of formula (IXa) and (IXb), wherein $PG^1$ is a suitable protecting group for the indole nitrogen, $PG^2$ is a suitable amino protecting group, and $R^8$ and $R^{20}$ are each independently $C_{1-6}$-alkyl, are important intermediates for syntheses of tripeptides that are used as building blocks for the syntheses of compounds of formula (I), wherein $R^2$ is $C_{1-6}$-alkyl (see Intermediate 4, step 3).

(IXa)

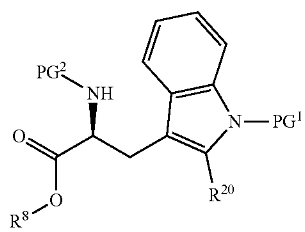

Accordingly, in one embodiment, there is provided a process for the manufacture of the compounds of formula (I) wherein $R^2$ is $C_{1-6}$-alkyl, comprising:

a) asymmetric hydrogenation of a compound of formula (VIII), wherein $PG^1$ is a suitable protecting group for the indole nitrogen, $PG^2$ is a suitable amino protecting group, and $R^8$ and $R^{20}$ are each independently $C_{1-6}$-alkyl, in the presence of a homogeneous catalyst (VIII)

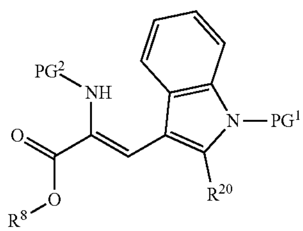

to afford a compound of formula (IXa) or (IXb), wherein $PG^1$ is a suitable protecting group for the indole nitrogen, $PG^2$ is a suitable amino protecting group, and $R^8$ and $R^{20}$ are each independently $C_{1-6}$-alkyl (IX)

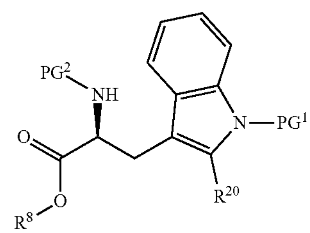

(IXb)

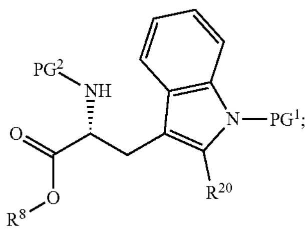

and b) further reacting said compound of formula (IXa) or (IXb) as described herein, to afford said compound of formula (I), wherein $R^2$ is $C_{1-6}$-alkyl.

In one embodiment, said homogeneous catalyst is [(1,2,5,6-η)-1,5-cyclooctadiene][(2S,2'S,5S,5'S)-1,1'-(1,2-phenylene)bis[2,5-diethylphospholane-κP]]-rhodium(1+) trifluoromethanesulfonate (CAS-RN 142184-30-3).

In a preferred embodiment, asymmetric hydrogenation of a compound of formula (VIII) yields a compound of formula (IXa).

Suitable amino protecting groups are well-known to one skilled in the art, some non-limiting examples being described herein.

In one embodiment, each occurrence of $PG^1$ is BOC (tert-butoxycarbonyl).

In one embodiment, each occurrence of $PG^2$ is Cbz (benzyloxycarbonyl).

In one embodiment, each occurrence of $R^8$ is methyl.

In one embodiment, each occurrence of $R^{20}$ is methyl.

In one aspect, the present invention provides a process for the manufacture of compounds of formula (IXa) or (IXb), wherein $PG^1$ is a suitable protecting group for the indole nitrogen, $PG^2$ is a suitable amino protecting group, and $R^8$ and $R^{20}$ are each independently $C_{1-6}$-alkyl, comprising:

(IXa)

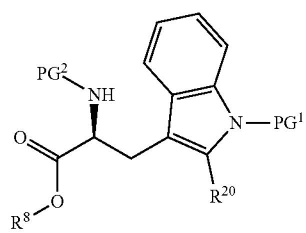

(IXb)

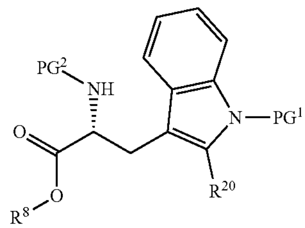

asymmetric hydrogenation of a compound of formula (VIII), wherein $PG^1$ is a suitable protecting group for the indole nitrogen, $PG^2$ is a suitable amino protecting group, and $R^8$ and $R^{20}$ are each independently $C_{1-6}$-alkyl, in the presence of a homogeneous catalyst (VIII)

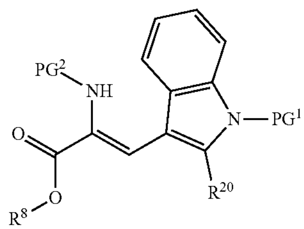

to afford said compound of formula (IXa) or (IXb).

Pharmaceutical Compositions

Another aspect of the invention provides pharmaceutical compositions or medicaments comprising the compounds of the invention and a therapeutically inert carrier, diluent or pharmaceutically acceptable excipient, as well as methods of using the compounds of the invention to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

In a preferred embodiment, there is provided a pharmaceutical composition comprising one or more compounds of the invention, wherein said pharmaceutical composition is suitable for intravenous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may comprise components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also comprise still other therapeutically valuable substances.

A typical formulation is prepared by mixing a compound of the present invention and a carrier or excipient. Suitable carriers and excipients are well known to those skilled in the art and are described in detail in, e.g., Ansel H. C. et al., *Ansel's Pharmaceutical Dosage Forms and Drug Delivery Systems* (2004) Lippincott, Williams & Wilkins, Philadelphia; Gennaro A. R. et al., *Remington: The Science and Practice of Pharmacy* (2000) Lippincott, Williams & Wilkins, Philadelphia; and Rowe R. C, *Handbook of Pharmaceutical Excipients* (2005) Pharmaceutical Press, Chicago. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at which compounds of the invention can be administered can vary within wide limits and will, of course, be fitted to the individual requirements in each particular case. In general, in the case of intravenous administration a daily dosage of about 1 to 1000 mg per person of a compound of general formula (I) should be appropriate, although the above upper limit can also be exceeded when necessary.

An example of a suitable intravenous dosage form is a sterile aqueous solution comprising about 1 mg to about 500 mg of a compound of the invention. Such a sterile aqueous solution for intravenous administration may be obtained e.g. by dissolving 1 mg to about 500 mg of a compound of the invention in water (e.g. about 50 mL) and adjusting the pH to 4-8, preferably around 7 by addition of aqueous sodium hydroxide solution. The procedure is completed by terminal sterilisation using methods known in the art.

An example of an aerosol formulation can be prepared by dissolving the compound, for example 10 to 100 mg, of the invention in a suitable buffer solution, e.g. a phosphate buffer, adding a tonicifier, e.g. a salt such as sodium chloride, if desired. The solution may be filtered, e.g., using a 0.2 μm filter, to remove impurities and contaminants.

Uses

The compounds of formula (I) and their pharmaceutically acceptable salts possess valuable pharmacological properties for the treatment or prevention of infections and resulting diseases, particularly bacteremia, pneumonia, meningitis, urinary tract infection, and wound infection, caused by pathogens, particularly by bacteria, more particularly by *Acinetobacter* species, most particularly by *Acinetobacter baumannii.*

The compounds of formula (I) and their pharmaceutically acceptable salts exhibit activity as antibiotics, particularly as antibiotics against *Acinetobacter* species, more particularly as antibiotics against *Acinetobacter baumannii*, most particularly as pathogen-specific antibiotics against *Acinetobacter baumannii.*

The compounds of formula (I) and their pharmaceutically acceptable salts can be used as antibiotics, i.e. as antibacterial pharmaceutical ingredients suitable in the treatment and prevention of bacterial infections, particularly in the treatment and prevention of bacterial infections caused by *Acinetobacter* species, more particularly in the treatment and prevention of bacterial infections caused by *Acinetobacter baumannii.*

The compounds of the present invention can be used, either alone or in combination with other drugs, for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii.*

One aspect of the present invention relates to pharmaceutical compositions comprising compounds of formula (I) as defined above or their pharmaceutically acceptable salts as defined above and one or more pharmaceutically acceptable excipients.

A further aspect of the present invention relates to pharmaceutical compositions comprising compounds of formula (I) or their pharmaceutically acceptable salts as defined above and one or more pharmaceutically acceptable excipients for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii.*

A further aspect of the present invention relates to compounds of formula (I) or their pharmaceutically acceptable salts as defined above for use as therapeutically active substances, especially for use as therapeutically active substances for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii.*

A further aspect of the present invention relates to compounds of formula (I) or their pharmaceutically acceptable salts as defined above for the use in the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii.*

A further aspect of the present invention relates to a method for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*, which method comprises administering compounds of formula (I) or their pharmaceutically acceptable salts as defined above to a subject.

A further aspect of the present invention relates to the use of compounds of formula (I) or their pharmaceutically acceptable salts as defined above for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii.*

A further aspect of the present invention relates to the use of compounds of formula (I) or their pharmaceutically acceptable salts as defined above for the preparation of medicaments for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii.* Such medicaments comprise compounds of formula (I) or their pharmaceutically acceptable salts as defined above.

In one embodiment, the present invention provides a compound of formula (I) as described herein, or a pharmaceutically acceptable salt thereof, for use in the treatment of infections and resulting diseases caused by Gram-negative bacteria.

In one embodiment, the present invention provides a compound of formula (I) as described herein, or a pharmaceutically acceptable salt thereof, for use in the treatment of infections and resulting diseases caused by an 'ESKAPE' pathogen (*Enterococcus faecium, Staphylococcus aureus, Klebsiella pneumoniae, Acinetobacter baumannii, Pseudomonas aeruginosa* and *Enterobacter* species & *E. coli*) or a combination thereof.

In one embodiment, the present invention provides a compound of formula (I) as described herein, or a pharmaceutically acceptable salt thereof, for use in the treatment of nosocomial infections.

In one embodiment, the present invention provides a compound of formula (I) as described herein, or a pharmaceutically acceptable salt thereof, for use in the treatment of infections and resulting diseases caused by Multi-Drug Resistant (MDR) bacteria, in particular by MDR *A. baumannii.*

In one embodiment, the present invention provides a compound of formula (I) as described herein, or a pharmaceutically acceptable salt thereof, for use in the treatment of infections and resulting diseases caused by Carbapenem resistant bacteria, in particular Carbapanem resistant *A. baumannii.*

EXAMPLES

The invention will be more fully understood by reference to the following examples. They should however not be construed as limiting the scope of the invention.

All examples and intermediates were prepared under nitrogen atmosphere if not specified otherwise.

Abbreviations Used aq.=aqueous; CAS-RN=Chemical Abstracts Service Registry Number; HPLC=high performance liquid chromatography; MPLC=medium pressure liquid chromatography; MS=mass spectrum; sat.=saturated.

Example 1

4-[(11S,14S,17S)-14-(4-Aminobutyl)-11-(3-aminopropyl)-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid

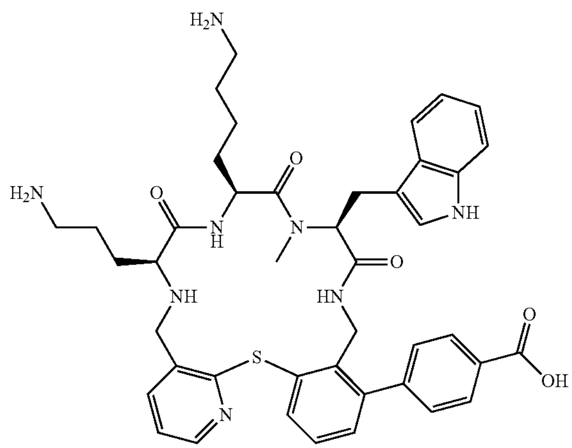 [SMILES: CN1C(=O)[C@H](CCCCN)NC(=O)[C@H](CCCN)NCc2cccnc2Sc2cccc(-c3ccc(C(=O)O)cc3)c2CNC(=O)[C@@H]1Cc1c[nH]c2ccccc12]

tert-Butyl 3-(((7S,10S,13S)-17-bromo-10-(4-((tert-butoxycarbonyl)amino)butyl)-7-(3-((tert-butoxycarbonyl)amino)propyl)-12-methyl-8,11,14-trioxo-5,6,7,8,9,10,11,12,13,14,15,16-dodecahydrobenzo[b]pyrido[3,2-p][1]thia[5,8,11,14]tetraazacycloheptadecin-13-yl)methyl)-1H-indole-1-carboxylate (intermediate 1; 2.15 g, 1.97 mmol) 4-(tert-butoxycarbonyl)phenylboronic acid (CAS-RN 850568-54-6; 675 mg, 2.95 mmol) and sodium carbonate (521 mg, 4.91 mmol) were dissolved in dioxane/water 6:1 (22 mL). The reaction mixture was sparged with argon for 2 min while sonicating the vessel in an ultrasonic bath. Then tetrakis(triphenylphosphine)-palladium(0) (459 mg, 393 μmol) was added, degassing continued for another 2 min, then the tube was sealed and heated at 120° C. under microwave irradiation for 30 min. After cooling the reaction mixture was partitioned between ethyl acetate and 1 M aq. sodium carbonate solution. The combined organic layers were washed with brine, dried over magnesium sulfate, filtered and evaporated to afford the crude product (1.95 g, light orange foam). The material was purified by MPLC using a RediSep Rf Gold® C18 Reversed Phase (100 g column, 20-40 μM particle size) as the stationary phase and a gradient from water (+0.05% trifluoroacetic acid) to acetonitrile as the eluent. After lyophilisation 2.21 g of a light yellow product were obtained. This material was dissolved in dichloromethane (22 mL) and treated at room temperature with trifluoroacetic acid (22 mL, 295 mmol), then after 90 min the reaction mixture was evaporated in vacuo. The residue was dissolved in water (22 mL), stirred at room temperature for 2 h, then lyophilised. The residue was dissolved in water/acetonitrile 10:1 and purified by preparative HPLC using a C18 Reverse Phase column (Phenomenex Gemini-NX 5u 110A, 100×30 mm), and a gradient from water (+0.05% trifluoroacetic acid) to acetonitrile as the eluent. Lyophilisation of the pure fractions produced the title compound as the tetrakis(trifluoroacetate) salt (1.65 g, 67%). White lyophilised powder, MS: 791.7 $[M+H]^+$.

Example 2

4-[(11S,14S,17S)-14-(4-Aminobutyl)-11-(3-amino-propyl)-25-chloro-17-(H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]-2-methylsulfonyl-benzoic acid

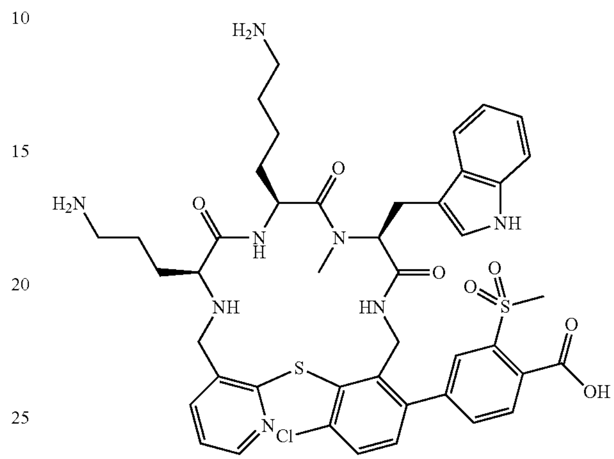

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-12-methyl-8,11,14-trioxo-5,6,7,8,9,10,11,12,13,14,15,16-dodecahydrobenzo[b]pyrido[3,2-p][1]thia[5,8,11,14]tetraazacycloheptadecin-13-yl)methyl)-1H-indole-1-carboxylate and 4-(tert-butoxycarbonyl)phenylboronic acid by tert-butyl 3-(((7S,10S,13S)-17-bromo-10-(4-((tert-butoxycarbonyl)amino)-butyl)-7-(3-((tert-butoxycarbonyl)amino)-propyl)-20-chloro-12-methyl-8,11,14-trioxo-5,6,7,8,9,10,11,12,13,14,15,16-dodecahydrobenzo[b]-pyrido[3,2-p][1,5,8,11,14]thiatetra-azacycloheptadecin-13-yl)methyl)-1H-indole-1-carboxylate [CAS-RN 2097294-18-1] and tert-butyl 2-(methylsulfonyl)-4-(4,4,5,5-tetramethyl-1,3,2-dioxaborolan-2-yl)benzoate (intermediate 6), respectively. White lyophilised powder, MS: 903.3 $[M+H]^+$.

The following examples were produced in analogy to example 2, replacing tert-butyl 2-(methylsulfonyl)-4-(4,4,5,5-tetramethyl-1,3,2-dioxaborolan-2-yl)benzoate by the appropriate boron reagent:

| No. | Chemical Name | Boron reagent | MS, m/z |
|---|---|---|---|
| 2.01 | 5-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]pyrazolo[1,5-a]pyridine-2-carboxylic acid | [2-[(2-methylpropan-2-yl)oxycarbonyl]pyrazolo[1,5-a]pyridin-5-yl]boronic acid (intermediate 8) | 865.3 $[M + H]^+$ |
| | 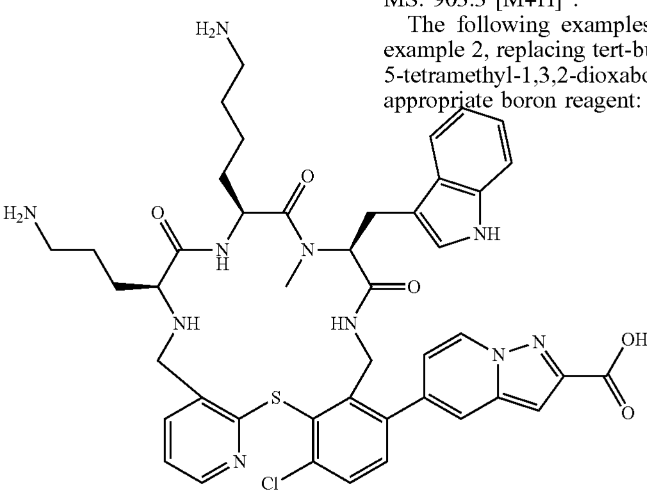 | | |
| 2.02 | 5-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19- | tert-butyl 5-(4,4,5,5-tetramethyl-1,3,2-dioxaborolan-2-yl)picolinate [CAS-RN | 826.3 $[M + H]^+$ |

-continued
| No. | Chemical Name | Boron reagent | MS, m/z |
|---|---|---|---|
| | pentazatricyclo[19.4.0.03,8]pentacosa-1(25),3,5,7,21,23-hexaen-22-yl]pyridine-2-carboxylic acid 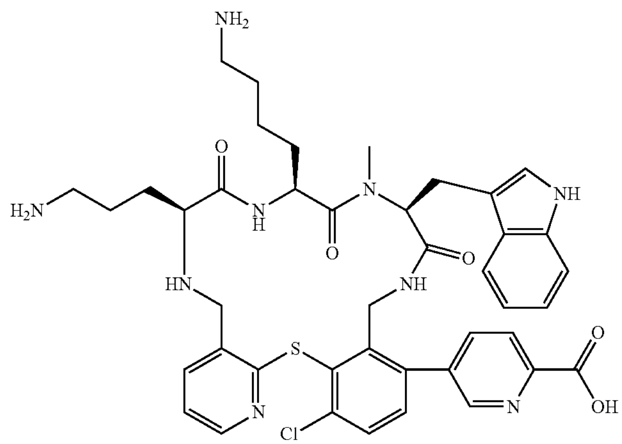 [SMILES: CN1C(=O)[C@H](CCCCN)NC(=O)[C@H](CCCN)NCc2cccnc2Sc2c(Cl)ccc(-c3ccc(C(=O)O)nc3)c2CNC(=O)[C@@H]1Cc1c[nH]c2ccccc12] | 1354356-24-3] | |
| 2.03 | 2-[4-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(21),3,5,7,22,24-hexaen-22-yl]-2-oxo-1-pyridyl]acetic acid 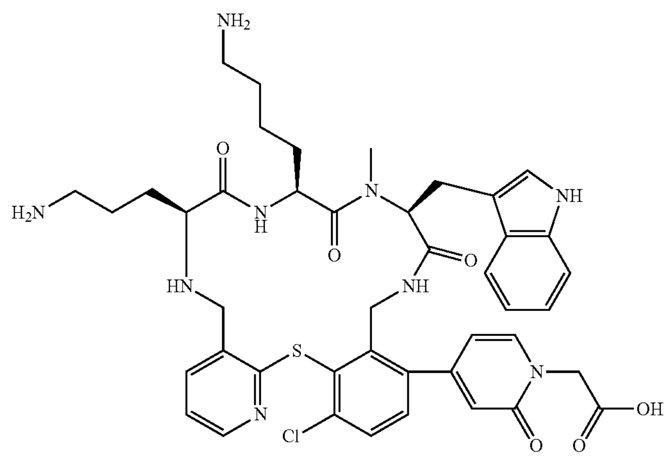 [SMILES: CN1C(=O)[C@H](CCCCN)NC(=O)[C@H](CCCN)NCc2cccnc2Sc2c(Cl)ccc(-c3ccn(CC(=O)O)c(=O)c3)c2CNC(=O)[C@@H]1Cc1c[nH]c2ccccc12] | (1-(2-(tert-butoxy)-2-oxoethyl)-2-oxo-1,2-dihydropyridin-4-yl)boronic acid (intermediate 7) | 856.3 [M + H]$^+$ |

Example 3

4-[(]S,14S,17S)-14-(4-Aminobutyl)-11-(3-aminopropyl)-25-chloro-17-(H-indol-3-ylmethyl)-16-methyl-12,15,18-trioxo-2-thia-4,10,13,16,19-pentazatricyclo [19.4.0.03,8]pentacosa-1(21),3(8),4,6,22,24-hexaen-22-yl]-2-hydroxy-benzoic acid

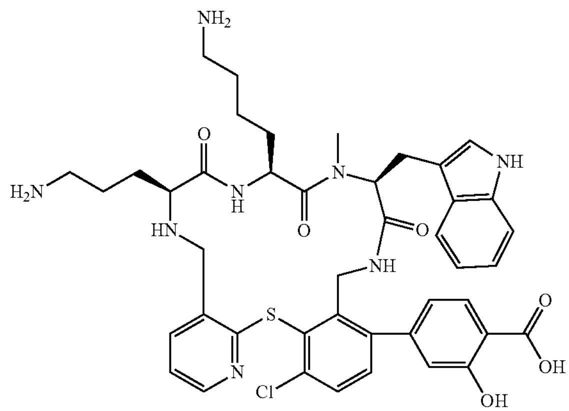 [SMILES: CN1C(=O)[C@H](CCCCN)NC(=O)[C@H](CCCN)NCc2cccnc2Sc2c(Cl)ccc(-c3ccc(C(=O)O)c(O)c3)c2CNC(=O)[C@@H]1Cc1c[nH]c2ccccc12]

Step 1: tert-Butyl 3-(((7S,10S,13S)-10-(4-((tert-butoxycarbonyl)amino)butyl)-7-(3-((tert-butoxycarbonyl)amino)propyl)-20-chloro-17-(3-hydroxy-4-(methoxycarbonyl)phenyl)-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate tert-Butyl 3-(((7S,10S,13S)-17-bromo-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate (CAS-RN 2097294-18-1; 250 mg, 0.23 mmol) was dissolved in 1,4-dioxane (6 mL) and water (1 mL), then methyl 2-hydroxy-4-(4,4,5,5-tetramethyl-1,3,2-dioxaborolan-2-yl)benzoate (CAS-RN 1073371-99-9; 256 mg, 922 μmol) and potassium carbonate (95 mg, 0.69 mmol) were added. The reaction mixture was sparged with argon for 2 min while sonicating the vessel in an ultrasonic bath. Then 1,1'-bis(diphenylphosphino)ferrocene dichloropalladium(II) (51.3 mg, 69.2 μmol) was added, and degassing continued for another 2 min. The tube was then sealed and heated at 100° C. under microwave irradiation for 90 min, then the reaction mixture was partitioned between water and ethyl acetate. The organic layer was dried over magnesium sulfate, filtered, and evaporated. The crude product was purified by chromatography (silica gel; heptane-(ethyl acetate/methanol 9:1) gradient) to produce the title compound (160 mg, 60%) as a white solid.

Step 2: 4-((7S,10S,13S)-13-((1H-Indol-3-yl)methyl)-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-17-yl)-2-hydroxybenzoic acid To a solution of tert-butyl 3-(((7S,10S,13S)-10-(4-((tert-butoxycarbonyl)amino)butyl)-7-(3-((tert-butoxycarbonyl)amino)propyl)-20-chloro-17-(3-hydroxy-4-(methoxycarbonyl)phenyl)-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate (160 mg, 138 μmol) in tetrahydrofuran (1 mL) was added a solution of sodium hydroxide (80 mg, 2.0 mmol) in water (1 mL). The reaction mixture was flushed with argon and sealed, then heated at 50° C. for 16 h, then acidified to pH 3 by addition of 1 M aq. hydrochloric acid solution. The reaction mixture was extracted with ethyl acetate, the organic layer was dried over sodium sulfate, filtered, and concentrated. Chromatography (silica gel; heptane-(ethyl acetate/methanol 9:1) gradient) produced the title compound (30 mg, 21%) as a white solid.

Step 3: 4-[(11S,14S,17S)-14-(4-Aminobutyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(21),3(8),4,6,22,24-hexaen-22-yl]-2-hydroxy-benzoic acid A mixture of 4-((7S,10S,13S)-13-((1H-indol-3-yl)methyl)-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-17-yl)-2-hydroxybenzoic acid (30 mg, 28.8 μmol), 37% aq. hydrochloric acid solution (500 μL) and tetrahydrofuran (500 μL) was stirred at room temperature for 2 h, then diluted with water (20 mL) and flushed with nitrogen to remove most of the tetrahydrofuran. Lyophilisation produced the title compound (23 mg, 96%). White lyophilised powder, MS: 841.3 $[M+H]^+$.

Example 4

4-[(11S,14S,17S)-14-(4-Amino-3,3-difluoro-butyl)-11-(3-aminopropyl)-25-chloro-17-(H-indol-3-ylmethyl)-16-methyl-12,15,18-trioxo-2-thia-4,10,13,16,19-pentazatricyclo[19.4.0.03,8]pentacosa-1(21),3,5,7,22,24-hexaen-22-yl]benzoic acid

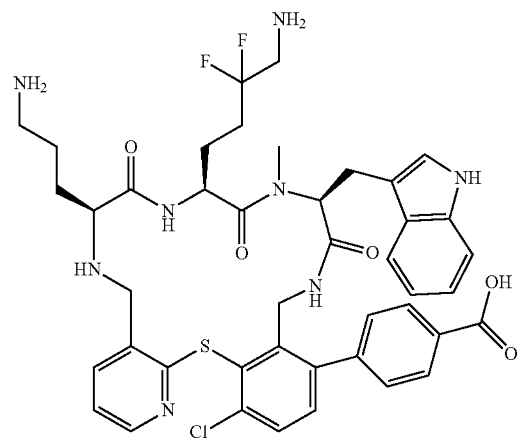 [SMILES: CN1C(=O)[C@H](CCC(F)(F)CN)NC(=O)[C@H](CCCN)NCc2cccnc2Sc2c(Cl)ccc(-c3ccc(C(=O)O)cc3)c2CNC(=O)[C@@H]1Cc1c[nH]c2ccccc12]

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-12-methyl-8,11,14-trioxo-5,6,7,8,9,10,11,12,13,14,15,16-dodecahydrobenzo[b]pyrido[3,2-p]

[1]thia[5,8,11,14]tetraazacycloheptadecin-13-yl)methyl)-1H-indole-1-carboxylate by tert-butyl 3-(((7S,10S,13S)-17-bromo-10-(4-((tert-butoxycarbonyl)amino)-3,3-difluorobutyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate (intermediate 1.09). White lyophilised powder, MS: 861.4 [M+H]$^+$.

Example 5

4-[(11S,14S,17S)-14-(4-aminobutyl)-11-(3-amino-3-oxo-propyl)-25-chloro-17-(1H-indol-3-ylmethyl)-16-methyl-12,15,18-trioxo-2-thia-4,10,13,16,19-pentazatricyclo[19.4.0.03,8]pentacosa-1(21),3,5,7,22,24-hexaen-22-yl]benzoic acid

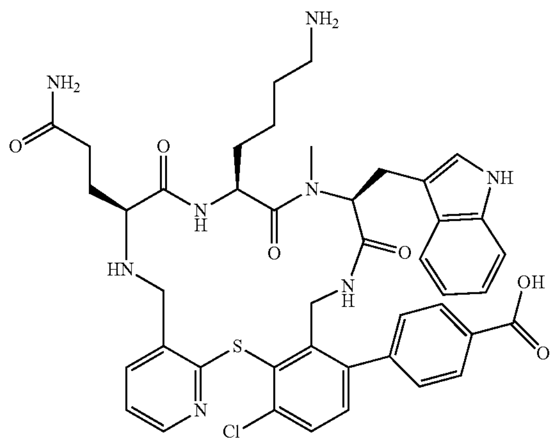 [SMILES: CN1C(=O)[C@H](CCCCN)NC(=O)[C@H](CCC(N)=O)NCc2cccnc2Sc2c(Cl)ccc(-c3ccc(C(=O)O)cc3)c2CNC(=O)[C@@H]1Cc1c[nH]c2ccccc12]

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-12-methyl-8,11,14-trioxo-5,6,7,8,9,10,11,12,13,14,15,16-dodecahydrobenzo[b]pyrido[3,2-p][1]thia[5,8,11,14]tetraazacycloheptadecin-13-yl)methyl)-1H-indole-1-carboxylate by tert-butyl 3-{[(11S,14S,17S)-22-bromo-14-(4-{[(tert-butoxy)carbonyl]amino}butyl)-25-chloro-16-methyl-12,15,18-trioxo-11-{2-[(triphenylmethyl)carbamoyl]ethyl}-2-thia-4,10,13,16,19-pentaazatricyclo[19.4.0.0^{3,8}]pentacosa-1(25),3(8),4,6,21,23-hexaen-17-yl]methyl}-1H-indole-1-carboxylate (intermediate 1.05). White lyophilised powder, MS: 839.6 [M+H]$^+$.

Example 6

4-[(11S,14S,17S)-14-(4-Aminobutyl)-11-(3-amino-propyl)-16-methyl-17-[(2-methyl-1H-indol-3-yl)methyl]-12,15,18-trioxo-2-thia-4,10,13,16,19-pentazatricyclo[19.4.0.03,8]pentacosa-1(25),3,5,7,21,23-hexaen-22-yl]benzoic acid

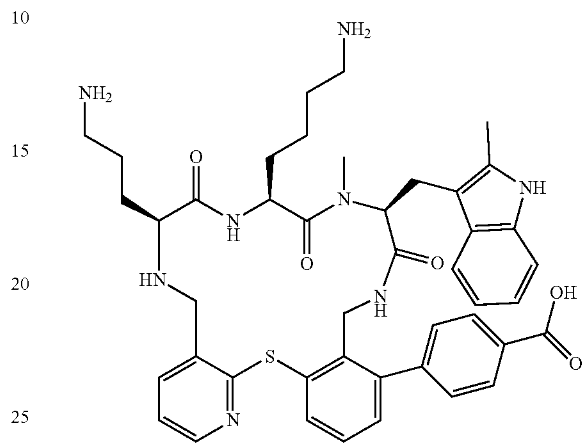

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-12-methyl-8,11,14-trioxo-5,6,7,8,9,10,11,12,13,14,15,16-dodecahydrobenzo[b]pyrido[3,2-p][1]thia[5,8,11,14]tetraazacycloheptadecin-13-yl)methyl)-1H-indole-1-carboxylate by tert-butyl 3-{[(11S,14S,17S)-22-bromo-14-(4-{[(tert-butoxy)carbonyl]amino}butyl)-11-(3-{[(tert-butoxy)carbonyl]amino}propyl)-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-2-methyl-1H-indole-1-carboxylate (intermediate 1.12). White lyophilised powder, MS: 805.5 [M+H]$^+$.

Example 7

4-[(11S,14S,17S)-14-(4-Aminobutyl)-11-(3-amino-propyl)-25-chloro-16-methyl-17-[(2-methyl-1H-indol-3-yl)methyl]-12,15,18-trioxo-2-thia-4,10,13,16,19-pentazatricyclo[19.4.0.03,8]pentacosa-1(25),3,5,7,21,23-hexaen-22-yl]benzoic acid

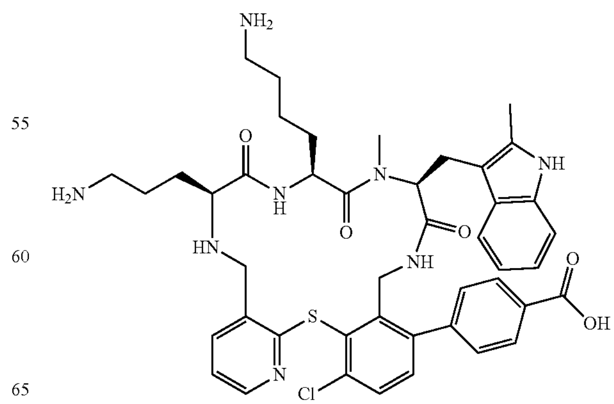

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-12-methyl-8,11,14-trioxo-5,6,7,8,9,10,11,12,13,14,15,16-dodecahydrobenzo[b]pyrido[3,2-p][1]thia[5,8,11,14]tetraazacycloheptadecin-13-yl)methyl)-1H-indole-1-carboxylate by tert-butyl 3-{[(11S,14S,17S)-22-bromo-14-(4-{[(tert-butoxy)carbonyl]amino}butyl)-11-(3-{[(tert-butoxy)carbonyl]amino}propyl)-25-chloro-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-2-methyl-1H-indole-1-carboxylate (intermediate 1.11). White lyophilised powder, MS: 839.6 [M+H]+.

Example 7.01

2-[4-[(11S,14S,17S)-14-(4-Aminobutyl)-11-(3-aminopropyl)-25-chloro-16-methyl-17-[(2-methyl-1H-indol-3-yl)methyl]-12,15,18-trioxo-2-thia-4,10,13,16,19-pentazatricyclo[19.4.0.03,8]pentacosa-1(25),3(8),4,6,21,23-hexaen-22-yl]-2-oxo-1-pyridyl]acetic acid

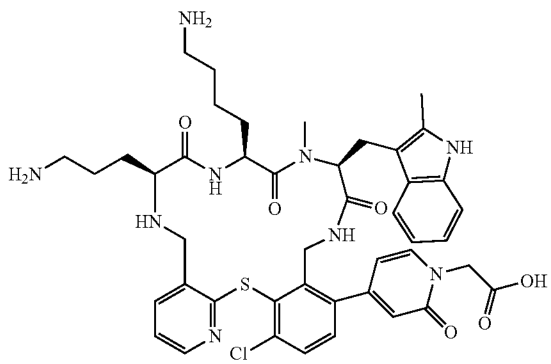 [SMILES: Cc1[nH]c2ccccc2c1C[C@H]1C(=O)NCc2c(-c3ccn(CC(=O)O)c(=O)c3)ccc(Cl)c2Sc2ncccc2CN[C@@H](CCCN)C(=O)N[C@@H](CCCCN)C(=O)N1C]

The title compound was produced in analogy to example 7, replacing 4-(tert-butoxycarbonyl)phenylboronic acid by (1-(2-(tert-butoxy)-2-oxoethyl)-2-oxo-1,2-dihydropyridin-4-yl)boronic acid (intermediate 7). White lyophilised powder, MS: 870.7 [M+H]+.

Example 8

4-[(11S,14S,17S)-14-(4-Aminobutyl)-11-(3-aminopropyl)-25-chloro-17-(H-indol-3-ylmethyl)-16-methyl-12,15,18-trioxo-2-thia-4,7,10,13,16,19-hexazatricyclo[19.4.0.03,8]pentacosa-1(21),3,5,7,22,24-hexaen-22-yl]benzoic acid

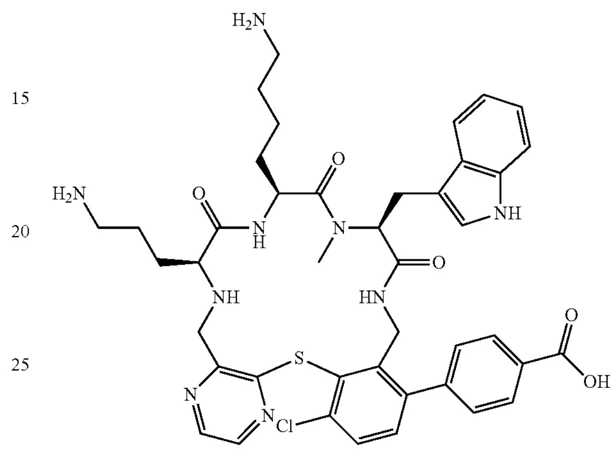

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-12-methyl-8,11,14-trioxo-5,6,7,8,9,10,11,12,13,14,15,16-dodecahydrobenzo[b]pyrido[3,2-p][1]thia[5,8,11,14]tetraazacycloheptadecin-13-yl)methyl)-1H-indole-1-carboxylate by tert-butyl 3-{[(11S,14S,17S)-22-bromo-14-(4-{[(tert-butoxy)carbonyl]amino}butyl)-11-(3-{[(tert-butoxy)carbonyl]amino}propyl)-25-chloro-16-methyl-12,15,18-trioxo-2-thia-4,7,10,13,16,19-hexaazatricyclo[19.4.0.0^{3,8}]pentacosa-1(21),3,5,7,22,24-hexaen-17-yl]methyl}-1H-indole-1-carboxylate (intermediate 1.01). White lyophilised powder, MS: 826.3 [M+H]+.

The following examples were produced in analogy to example 8, replacing 4-(tert-butoxycarbonyl)phenylboronic acid by the appropriate boron reagent:

| No. | Chemical Name | Boron reagent | MS, m/z |
|---|---|---|---|
| 8.01 | 2-chloro-4-[rac-(11S,14S,17S)-14-(4-aminobutyl)-11-(3-aminopropyl)-25-chloro-17-(1H-indol-3-ylmethyl)-16-methyl-12,15,18-trioxo-2-thia-4,7,10,13,16,19-hexazatricyclo[19.4.0.03,8]pentacosa-1(21),3,5,7,22,24-hexaen-22-yl]benzoic acid | 4-borono-2-chlorobenzoic acid [CAS-RN 136496-72-5] | 860.2 [M + H]+ |

-continued

| No. | Chemical Name | Boron reagent | MS, m/z |
| --- | --- | --- | --- |
| | 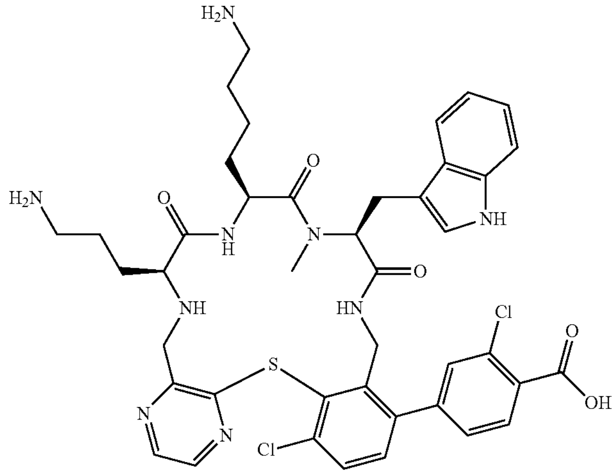 [SMILES: CN1C(=O)[C@H](CCCCN)NC(=O)[C@H](CCCN)NCc2nccnc2Sc2c(Cl)ccc(-c3ccc(C(=O)O)c(Cl)c3)c2CNC(=O)[C@@H]1Cc1c[nH]c2ccccc12] | | |
| 8.02 | 4-[(11S,14S,17S)-14-(4-aminobutyl)-11-(3-aminopropyl)-25-chloro-17-(1H-indol-3-ylmethyl)-16-methyl-12,15,18-trioxo-2-thia-4,7,10,13,16,19-hexazatricyclo[19.4.0.03,8]pentacosa-1(21),3,5,7,22,24-hexaen-22-yl]-2-fluoro-benzoic acid | tert-butyl 2-fluoro-4-(4,4,5,5-tetramethyl-1,3,2-dioxaborolan-2-yl)benzoate [CAS-RN 1351501-00-2] | 844.3 [M + H]+ |
| | 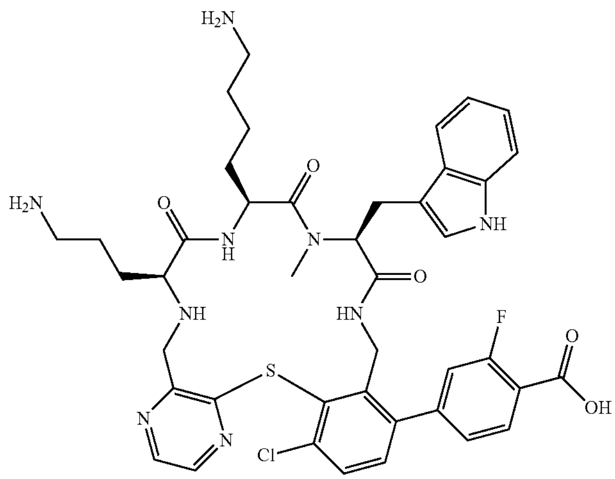 [SMILES: CN1C(=O)[C@H](CCCCN)NC(=O)[C@H](CCCN)NCc2nccnc2Sc2c(Cl)ccc(-c3ccc(C(=O)O)c(F)c3)c2CNC(=O)[C@@H]1Cc1c[nH]c2ccccc12] | | |
| 8.03 | 2-methoxy-4-[rac-(11S,14S,17S)-14-(4-aminobutyl)-11-(3-aminopropyl)-25-chloro-17-(1H-indol-3-ylmethyl)-16-methyl-12,15,18-trioxo-2-thia-4,7,10,13,16,19-hexazatricyclo [19.4.0.03,8]pentacosa-1(25),3(8),4,6,21,23-hexaen-22-yl]benzoic acid | tert-butyl 2-methoxy-4-(4,4,5,5-tetramethyl-1,3,2-dioxaborolan-2-yl)benzoate (intermediate 6.01) | 856.3 [M + H]+ |
| | 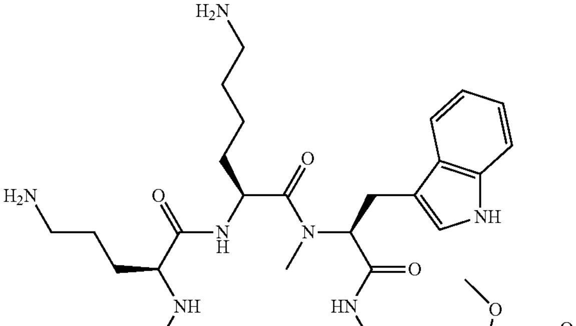 | | |

Example 9

4-[(11S,14S,17S)-14-(4-aminobutyl)-11-(3-amino-propyl)-25-fluoro-17-(H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid

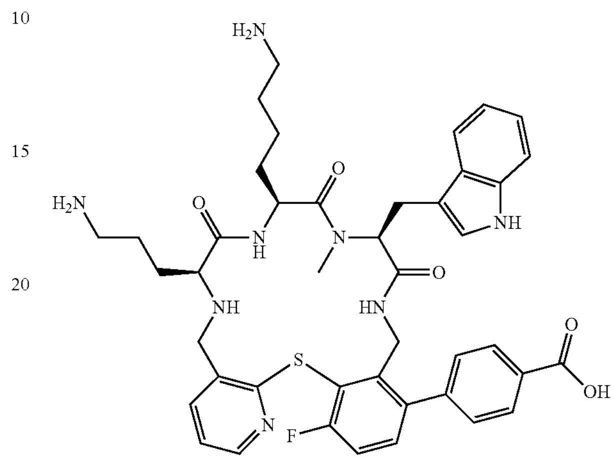

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-12-methyl-8,11,14-trioxo-5,6,7,8,9,10,11,12,13,14,15,16-dodecahydrobenzo[b]pyrido[3,2-p][1]thia[5,8,11,14]tetraazacycloheptadecin-13-yl)methyl)-1H-indole-1-carboxylate by tert-butyl 3-(((7S,10S,13S)-17-bromo-10-(4-((tert-butoxycarbonyl)amino)butyl)-7-(3-((tert-butoxycarbonyl)amino)propyl)-20-fluoro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate (intermediate 1.02). White lyophilised powder, MS: 809.4 $[M+H]^+$.

The following examples were produced in analogy to example 2, replacing 4-(tert-butoxycarbonyl)phenylboronic acid by the appropriate boron reagent:

| No. | Chemical Name | Boron reagent | MS, m/z |
|---|---|---|---|
| 9.01 | 2-[4-[(11S,14S,17S)-14-(4-Aminobutyl)-11-(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]-2-oxo-1-pyridyl]acetic acid 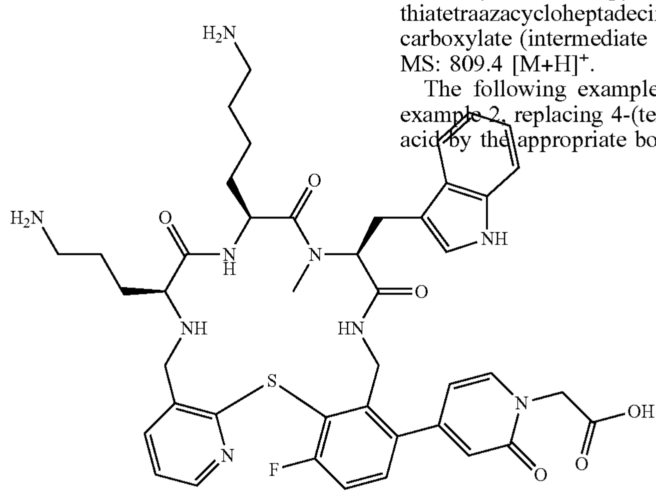 | (1-(2-(tert-butoxy)-2-oxoethyl)-2-oxo-1,2-dihydropyridin-4-yl)boronic acid (intermediate 7) | 840.6 $[M + H]^+$ |
| 9.02 | (E)-3-[4-[(11S,14S,17S)-14-(4-Aminobutyl)-11-(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]-2-oxo-1-pyridyl]prop-2-enoic acid | (E)-(1-(3-(tert-butoxy)-3-oxoprop-1-en-1-yl)-2-oxo-1,2-dihydropyridin-4-yl)boronic acid (intermediate 9) | 852.3 $[M + H]^+$ |

-continued

| No. | Chemical Name | Boron reagent | MS, m/z |
|---|---|---|---|
| | 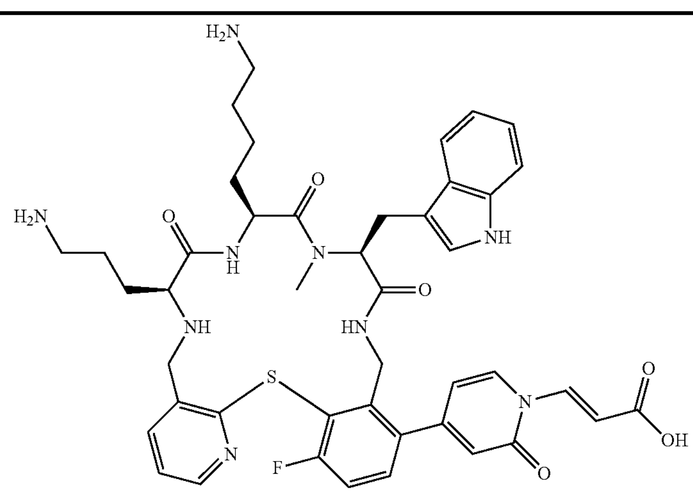 | | |

Example 10

4-[(11S,14S,17S)-14-(4-Aminobutyl)-11-(3-aminopropyl)-17-(1H-indol-3-ylmethyl)-16,25-dimethyl-12,15,18-trioxo-2-thia-4,10,13,16,19-pentazatricyclo[19.4.0.03,8]pentacosa-1(25),3(8),4,6,21,23-hexaen-22-yl]benzoic acid

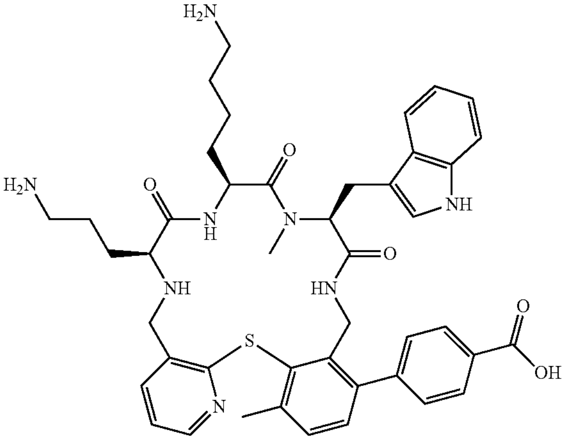 [SMILES: Cc1ccc(-c2ccc(C(=O)O)cc2)c2c1Sc1ncccc1CN[C@@H](CCCN)C(=O)N[C@@H](CCCCN)C(=O)N(C)[C@@H](Cc1c[nH]c3ccccc13)C(=O)NC2]

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-12-methyl-8,11,14-trioxo-5,6,7,8,9,10,11,12,13,14,15,16-dodecahydrobenzo[b]pyrido[3,2-p][1]thia[5,8,11,14]tetraazacycloheptadecin-13-yl)methyl)-1H-indole-1-carboxylate by tert-butyl 3-(((7S,10S,13S)-17-bromo-10-(4-((tert-butoxycarbonyl)amino)butyl)-7-(3-((tert-butoxycarbonyl)amino)propyl)-12,20-dimethyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate (intermediate 1.06). White lyophilised powder, MS: 805.4 $[M+H]^+$.

Example 10.01

2-[4-[(11S,14S,17S)-14-(4-Aminobutyl)-11-(3-aminopropyl)-17-(1H-indol-3-ylmethyl)-16,25-dimethyl-12,15,18-trioxo-2-thia-4,10,13,16,19-pentazatricyclo[19.4.0.03,8]pentacosa-1(25),3(8),4,6,21,23-hexaen-22-yl]-2-oxo-1-pyridyl]acetic acid

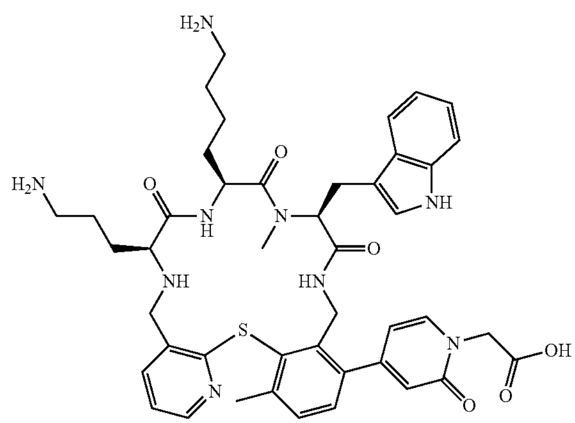 [SMILES: Cc1ccc(-c2ccn(CC(=O)O)c(=O)c2)c2c1Sc1ncccc1CN[C@@H](CCCN)C(=O)N[C@@H](CCCCN)C(=O)N(C)[C@@H](Cc1c[nH]c3ccccc13)C(=O)NC2]

The title compound was produced in analogy to example 10, replacing 4-(tert-butoxycarbonyl)phenylboronic acid by (1-(2-(tert-butoxy)-2-oxoethyl)-2-oxo-1,2-dihydropyridin-4-yl)boronic acid (intermediate 7). White lyophilised powder, MS: 836.4 $[M+H]^+$.

Example 11

4-[(11S,14S,17S)-14-(4-Aminobutyl)-11-(3-amino-propyl)-17-(1H-indol-3-ylmethyl)-25-methoxy-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid

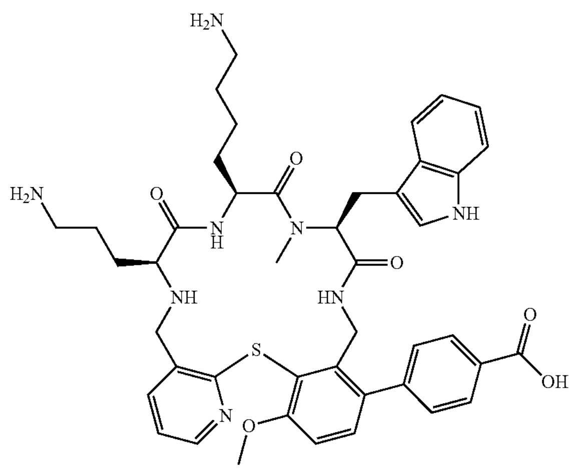 [SMILES: COc1ccc(-c2ccc(C(=O)O)cc2)c2c1Sc1ncccc1CN[C@@H](CCCN)C(=O)N[C@@H](CCCCN)C(=O)N(C)[C@@H](Cc1c[nH]c3ccccc13)C(=O)NC2]

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-12-methyl-8,11,14-trioxo-5,6,7,8,9,10,11,12,13,14,15,16-dodecahydrobenzo[b]pyrido[3,2-p][1]thia[5,8,11,14]tetraazacycloheptadecin-13-yl)methyl)-1H-indole-1-carboxylate by tert-butyl 3-{[(11S,14S,17S)-22-bromo-14-(4-{[(tert-butoxy)carbonyl]amino}butyl)-11-(3-{[(tert-butoxy)carbonyl]amino}propyl)-25-methoxy-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate (intermediate 1.10). White lyophilised powder, MS: 821.6 [M+H]$^+$.

Example 12

4-[(11S,14S,17S)-11,14-bis(3-Aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(21),3,5,7,22,24-hexaen-22-yl]benzoic acid

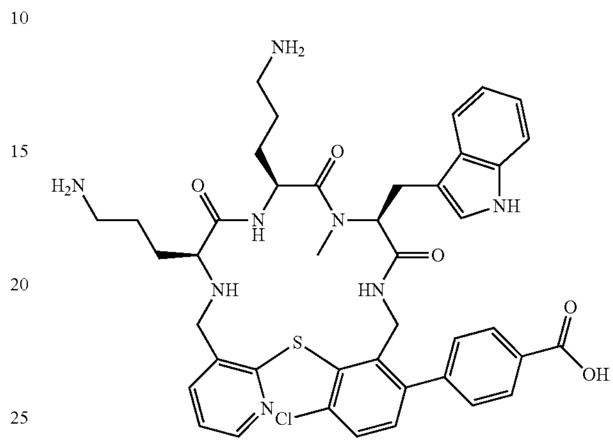

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-12-methyl-8,11,14-trioxo-5,6,7,8,9,10,11,12,13,14,15,16-dodecahydrobenzo[b]pyrido[3,2-p][1]thia[5,8,11,14]tetraazacycloheptadecin-13-yl)methyl)-1H-indole-1-carboxylate by tert-butyl 3-{[(11S,14S,17S)-22-bromo-11,14-bis(3-{[(tert-butoxy)carbonyl]amino}propyl)-25-chloro-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate (intermediate 1.03). White lyophilised powder, MS: 811.3 [M+H]$^+$.

Example 13

4-[(11S,14S,17S)-14-(2-Aminoethyl)-11-(3-amino-propyl)-25-chloro-17-(H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid

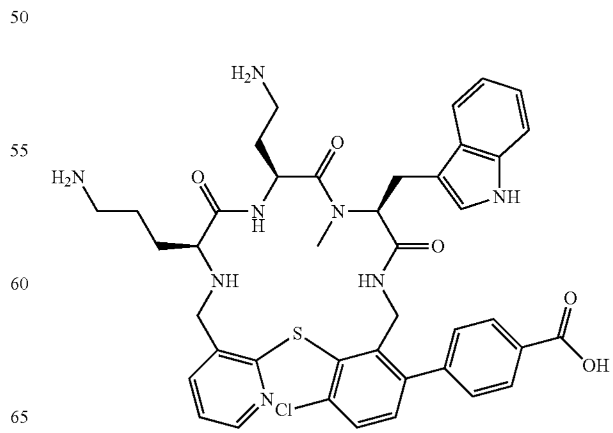

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-12-methyl-8,11,14-trioxo-5,6,7,8,9,10,11,12,13,14,15,16-dodecahydrobenzo[b]pyrido[3,2-p][1]thia[5,8,11,14]tetraazacycloheptadecin-13-yl)methyl)-1H-indole-1-carboxylate by tert-butyl 3-{[(11S,14S,17S)-22-bromo-14-(2-{[(tert-butoxy)carbonyl]amino}ethyl)-11-(3-{[(tert-butoxy)carbonyl]amino}propyl)-25-chloro-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate (intermediate 1.13). White lyophilised powder, MS: 797.5 $[M+H]^+$.

Example 14

4-[(11S,14S,17S)-11,14-bis(3-Aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid

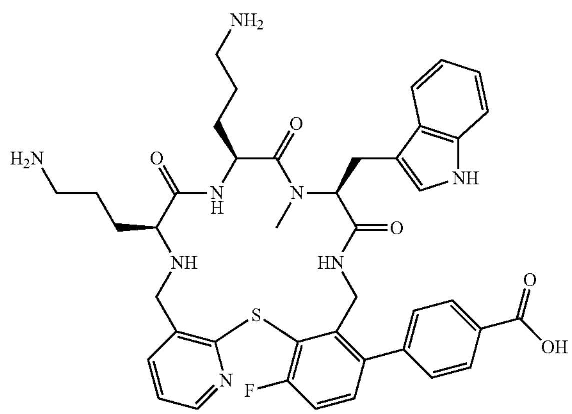 [SMILES: CN1C(=O)[C@H](CCCN)NC(=O)[C@H](CCCN)NCc2cccnc2Sc2c(F)ccc(-c3ccc(C(=O)O)cc3)c2CNC(=O)[C@@H]1Cc1c[nH]c2ccccc12]

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-12-methyl-8,11,14-trioxo-5,6,7,8,9,10,11,12,13,14,15,16-dodecahydrobenzo[b]pyrido[3,2-p][1]thia[5,8,11,14]tetraazacycloheptadecin-13-yl)methyl)-1H-indole-1-carboxylate by tert-butyl 3-{[(11S,14S,17S)-22-bromo-11,14-bis(3-{[(tert-butoxy)carbonyl]amino}propyl)-25-fluoro-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate (intermediate 1.04). White lyophilised powder, MS: 795.3 $[M+H]^+$.

Example 14.01

5-[(11S,14S,17S)-11,14-bis(3-Aminopropyl)-25-fluoro-17-(H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]pyridine-2-carboxylic acid

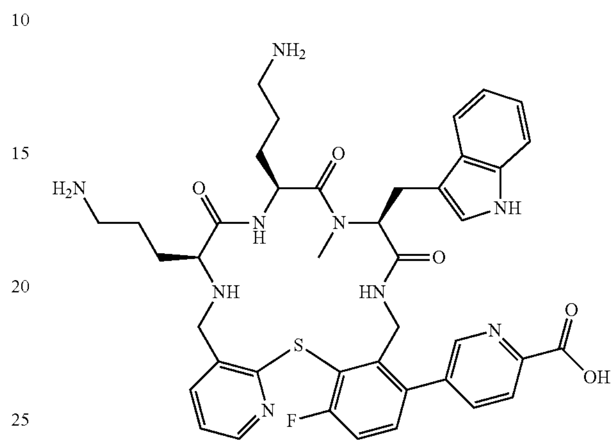

The title compound was produced in analogy to example 14, replacing 4-(tert-butoxycarbonyl)phenylboronic acid by tert-butyl 5-(4,4,5,5-tetramethyl-1,3,2-dioxaborolan-2-yl)picolinate [CAS-RN 1354356-24-3]. White lyophilised powder, MS: 796.6 $[M+H]^+$.

Example 15

4-[(11S,14S,17S)-14-(4-Aminobutyl)-11-(2-aminoethyl)-25-chloro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid

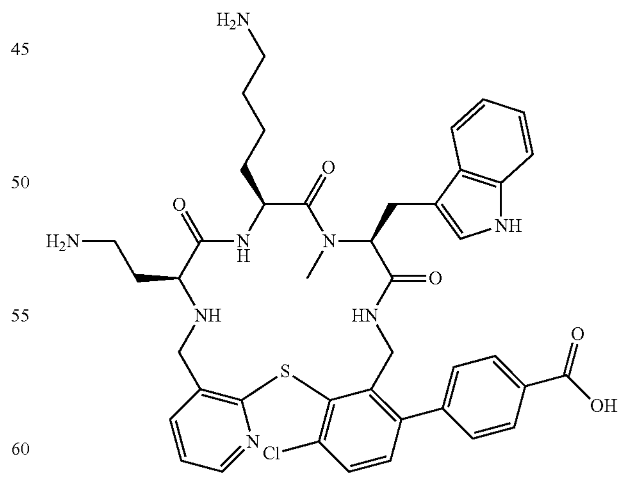

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-12-methyl-8,11,14-trioxo-5,6,7,8,9,10,11,12,13,14,15,16-dodecahydrobenzo[b]pyrido[3,2-p]

[1]thia[5,8,11,14]tetraazacycloheptadecin-13-yl)methyl)-1H-indole-1-carboxylate by tert-butyl 3-{[(11S,14S,17S)-22-bromo-14-(4-{[(tert-butoxy)carbonyl]amino}butyl)-11-(2-{[(tert-butoxy)carbonyl]amino}ethyl)-25-chloro-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate (intermediate 1.07). White lyophilised powder, MS: 811.4 $[M+H]^+$.

Example 16

4-[(11S,14S,17S)-11-(2-Aminoethyl)-14-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid

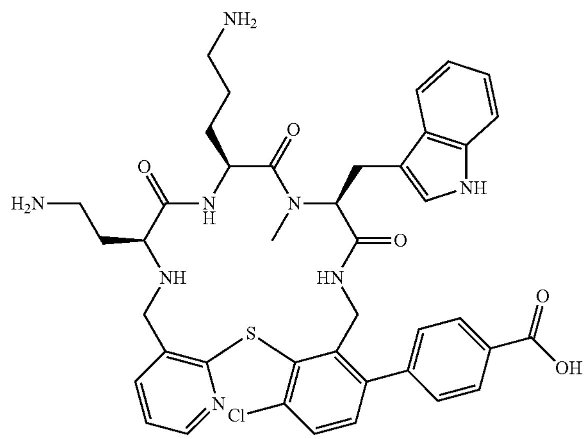 [SMILES: CN1C(=O)[C@H](CCCN)NC(=O)[C@H](CCN)NCc2cccnc2Sc2c(Cl)ccc(-c3ccc(C(=O)O)cc3)c2CNC(=O)[C@@H]1Cc1c[nH]c2ccccc12]

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-12-methyl-8,11,14-trioxo-5,6,7,8,9,10,11,12,13,14,15,16-dodecahydrobenzo[b]pyrido[3,2-p][1]thia[5,8,11,14]tetraazacycloheptadecin-13-yl)methyl)-1H-indole-1-carboxylate by tert-butyl 3-{[(11S,14S,17S)-22-bromo-11-(2-{[(tert-butoxy)carbonyl]amino}ethyl)-14-(3-{[(tert-butoxy)carbonyl]amino}propyl)-25-chloro-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate (intermediate 1.08). White lyophilised powder, MS: 797.6 $[M+H]^+$.

Example 17

4-[(11S,14S,17S)-11,14-bis(3-Aminopropyl)-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid

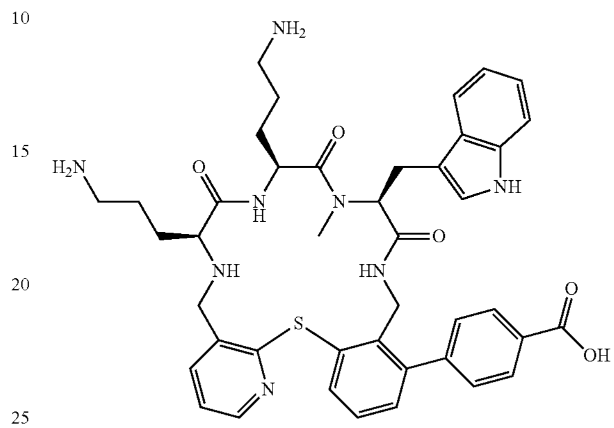

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-12-methyl-8,11,14-trioxo-5,6,7,8,9,10,11,12,13,14,15,16-dodecahydrobenzo[b]pyrido[3,2-p][1]thia[5,8,11,14]tetraazacycloheptadecin-13-yl)methyl)-1H-indole-1-carboxylate by tert-butyl 3-{[(11S,14S,17S)-22-bromo-11,14-bis(3-{[(tert-butoxy)carbonyl]amino}propyl)-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate (intermediate 1.14). White lyophilised powder, MS: 777.4 $[M+H]^+$.

Example 18

4-[(11S,14S,17S)-14-(4-Aminobutyl)-11-(3-aminopropyl)-17-(1H-indol-3-ylmethyl)-16-methyl-12,15,18-trioxo-2-thia-4,10,13,16,19,24-hexazatricyclo[19.4.0.03,8]pentacosa-1(25),3(8),4,6,21,23-hexaen-22-yl]benzoic acid

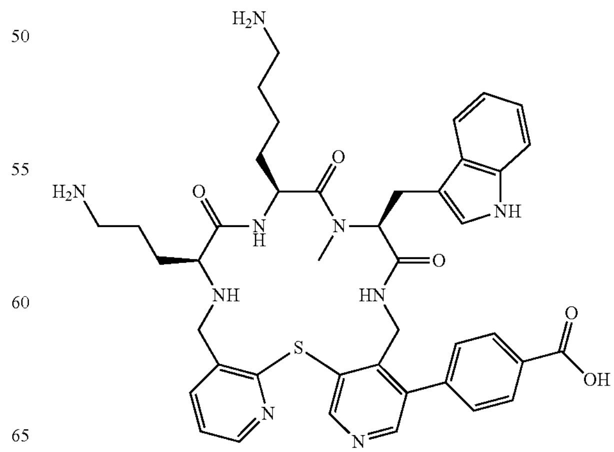

The title compound was produced in analogy to example 1, replacing tert-butyl 3-(((7S,10S,13S)-17-bromo-10-(4-((tert-butoxycarbonyl)amino)butyl)-7-(3-((tert-butoxycarbonyl)amino)propyl)-12-methyl-8,11,14-trioxo-5,6,7,8,9,10,11,12,13,14,15,16-dodecahydrobenzo[b]pyrido[3,2-p][1]thia[5,8,11,14]tetraazacycloheptadecin-13-yl)methyl)-1H-indole-1-carboxylate by tert-butyl 3-{[(11S,14S,17S)-22-bromo-14-(4-{[(tert-butoxy)carbonyl]amino}butyl)-11-(3-{[(tert-butoxy)carbonyl]amino}propyl)-16-methyl-12,15,18-trioxo-2-thia-4,10,13,16,19,24-hexaazatricyclo[19.4.0.0^{3,8}]pentacosa-1(21),3,5,7,22,24-hexaen-17-yl]methyl}-1H-indole-1-carboxylate (intermediate 1.15). White lyophilised powder, MS: 792.7 $[M+H]^+$.

Intermediates

General Procedure for Peptide Macrocycle Synthesis

1. Solid Phase Peptide Synthesis

The tripeptide sequence was synthesized manually via state-of-the-art solid phase synthesis protocols (Fmoc-chemistry) as referenced by e.g.: Kates and Albericio, Eds., "Solid Phase Synthesis: A practical guide", Marcel Dekker, New York, Basel, 2000.

As a solid support 2-chloro-tritylchloride resin (1.6 meq/g, 100-200 mesh) was used. This resin was loaded with the first amino acid (0.6 equivalents) and diisopropylethylamine (8 equivalents) in dry dichloromethane overnight at room temperature. After extensive washing with N,N-dimethylformamide and dichloromethane, the 9-fluorenylmethoxycarbonyl protecting group was cleaved off with a mixture of 50% piperidine in dichlomethane/N,N-dimethylformamide (1:1) in N,N-dimethylformamide for 30 min at room temperature. After washing with N,N-dimethylformamide, dichloromethane and methanol the resin was dried under vacuum at room temperature overnight. The resin loading was determined via weight increase.

The second amino acid was coupled with 4 equivalents of 2-chloro-1-methylpyridinium iodide as coupling reagent, 6 equivalents of N,N-diisopropylethylamine in dichlomethane/N,N-dimethylformamide (1:1) overnight at room temperature. The resin was extensively washed with N,N-dimethylformamide and dichloromethane and the coupling rate was controlled by a test-cleavage.

The 9-fluorenylmethoxycarbonyl-group from the dipeptide was cleaved with a mixture of piperidine/dichloromethane/N,N-dimethylformamide (2:1:1) for maximally 5 min followed by washings with N,N-dimethylformamide and dichloromethane. The cleavage rates were again controlled by test-cleavage.

The third amino acid was coupled using 4 equivalents of O-(7-azabenzotriazol-1-yl)-N,N,N',N'-tetramethyluronium-hexafluorophosphate as coupling reagent and 6 equivalents diisopropylethylamine. Complete couplings were accomplished at room temperature for 2-4 hours with the coupling rate again controlled by a test-cleavage.

The 9-fluorenylmethoxycarbonyl-group from the tripeptide was cleaved with a mixture of 20% piperidine in N,N-dimethylformamide for 2×15-20 min at room temperature followed by washings with N,N-dimethylformamide and dichloromethane (test-cleavage).

2. Reductive Amination:

Resin with tripeptide was washed with dichloromethane, the corresponding tether dissolved in a mixture of 1-methyl-2-pyrrolidone/trimethyl orthoformate/acetic acid (49.7/49.7/0.6) and the solution was added to the resin. The mixture was shaken at room temperature for 30 min up to 3 h, then 10 equivalents of sodium cyanoborohydride were added and the reaction mixture was shaken at room temperature overnight. Finally, the resin was washed with N,N-dimethylformamide, dichloromethane, methanol/dichloromethane (1:1) and N,N-dimethylformamide.

The 9-fluorenylmethoxycarbonyl-group on the tether was cleaved with a mixture of 20% piperidine in N,N-dimethylformamide for 2× 15-20 min at room temperature followed by washings with N,N-dimethylformamide and dichloromethane (test-cleavage).

3. Cleavage:

A cleavage-cocktail of 20% hexafluoroisopropanol in dichloromethane was added to the resin and the mixture was stirred for 2 h at room temperature. The resin was filtered off and the solution was evaporated to dryness. The residue was dissolved in water/acetonitrile and lyophilized.

4. Cyclisation:

The obtained crude linear compound was cyclized by dissolving the powder in N,N-dimethylformamide. 1.2 equivalents of O-(7-azabenzotriazol-1-yl)-N,N,N',N'-tetramethyluronium-hexafluorophosphate and 5 equivalents diisopropylethylamine were added and the reaction mixture stirred at room temperature. Progress of the reaction was monitored by HPLC. After completion, the reaction mixture was diluted with ethyl acetate, washed with water and brine, dried over magnesium sulfate, filtered, and evaporated. The residue was chromatographed with silica gel using a heptane-ethyl acetate gradient as the eluent. yielding the crude product.

5. Purification:

The crude product was purified by reversed phase high-performance liquid chromatography (RP-HPLC) using a Phenomenex Gemini-NX 5u 110A column (100×30 mm) as the stationary phase and a gradient from water (+0.05% trifluoroacetic acid) to acetonitrile as the eluent. Fractions were collected and analyzed by LC/MS. Pure product samples were combined and lyophilized. Product identification was obtained via mass spectrometry.

Intermediate 1 tert-Butyl 3-{[(11S,14S,17S)-22-bromo-14-(4-{[(tert-butoxy)carbonyl]amino}butyl)-11-(3-{[(tert-butoxy)carbonyl]amino}propyl)-16-methyl-12,15,18-trioxo-2-thia-4,10,13,16,19-pentaazatricyclo[19.4.0.0^{3,8}]pentacosa-1(25),3(8),4,6,21,23-hexaen-17-yl]methyl}-1H-indole-1-carboxylate

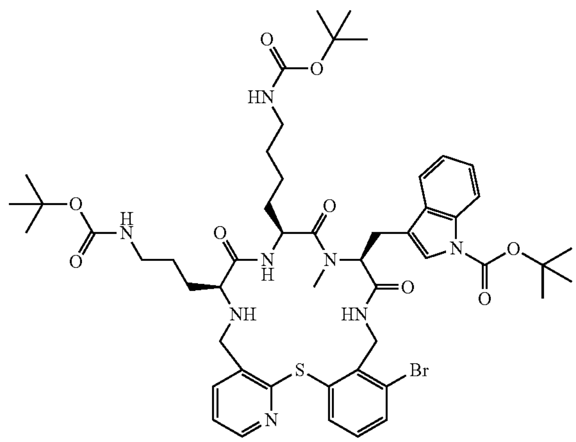 [SMILES: CN1C(=O)[C@H](CCCCNC(=O)OC(C)(C)C)NC(=O)[C@H](CCCNC(=O)OC(C)(C)C)NCc2cccnc2Sc2cccc(Br)c2CNC(=O)[C@@H]1Cc1cn(C(=O)OC(C)(C)C)c2ccccc12]

The title compound was produced according to the General procedure for Peptide Macrocycle Synthesis, using 1-[(1,1-dimethylethoxy)carbonyl]-N-[(9H-fluoren-9-ylmethoxy)carbonyl]-N-methyl-L-tryptophan [CAS-RN 197632-75-0] as the first amino acid, $N^6$-[(1,1-dimethylethoxy)carbonyl]-$N^2$-[(9H-fluoren-9-ylmethoxy)carbonyl]-L-lysine [CAS-RN 71989-26-9] as the second amino acid, $N^5$-[(1,1-dimethylethoxy)carbonyl]-$N^2$-[(9H-fluoren-9-ylmethoxy)carbonyl]-L-ornithine [CAS-RN 109425-55-0] as the third amino acid, and 9H-fluoren-9-ylmethyl N-[[2-bromo-6-[(3-formyl-2-pyridyl)sulfanyl]phenyl]methyl]carbamate (intermediate 2) as the tether. White solid, MS: 1051.7 $[M+H]^+$.

Intermediate 1.01 tert-Butyl 3-(((7S,10S,13S)-17-bromo-10-(4-((tert-butoxycarbonyl)amino)butyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrazino[2,3-p][1,5,8,11,14]thiatetraazacycloheptadecin-13-yl)methyl)-1H-indole-1-carboxylate

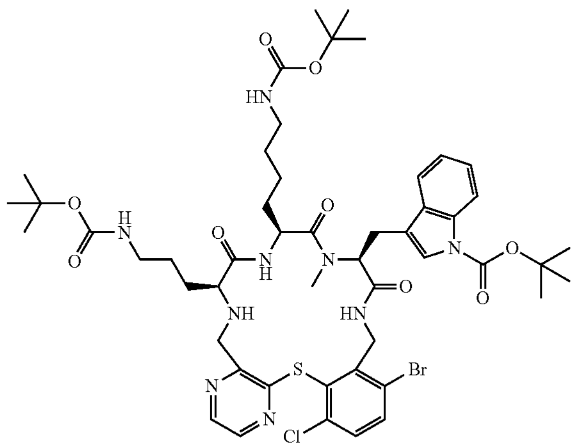 [SMILES: CN1C(=O)[C@H](CCCCNC(=O)OC(C)(C)C)NC(=O)[C@H](CCCNC(=O)OC(C)(C)C)NCc2nccnc2Sc2c(Cl)ccc(Br)c2CNC(=O)[C@@H]1Cc1cn(C(=O)OC(C)(C)C)c2ccccc12]

The title compound was produced in analogy to intermediate 1, replacing 9H-fluoren-9-ylmethyl N-[[2-bromo-6-[(3-formyl-2-pyridyl)sulfanyl]phenyl]methyl]carbamate by 9H-fluoren-9-ylmethyl N-[[6-bromo-3-chloro-2-(3-formylpyrazin-2-yl)sulfanyl-phenyl]methyl]carbamate (intermediate 3). Off-white solid, MS: 1084.9 $[M+H]^+$.

Intermediate 1.02 tert-Butyl 3-{[(11S,14S,17S)-22-bromo-11,14-bis(3-{[(tert-butoxy)carbonyl]amino}propyl)-25-fluoro-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate

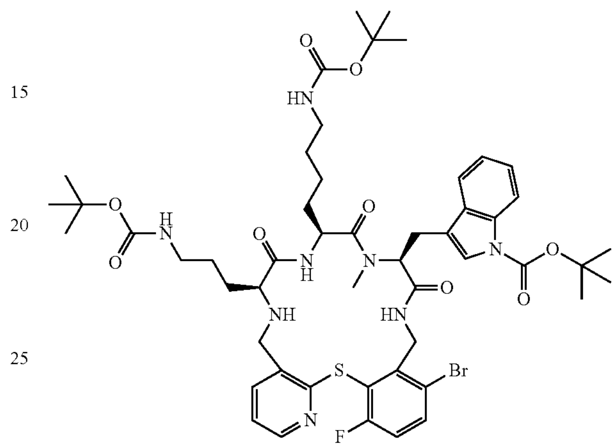

The title compound was produced in analogy to intermediate 1, replacing 9H-fluoren-9-ylmethyl N-[[2-bromo-6-[(3-formyl-2-pyridyl)sulfanyl]phenyl]methyl]carbamate by (9H-fluoren-9-yl)methyl 6-bromo-3-fluoro-2-((3-formylpyridin-2-yl)thio)benzylcarbamate (intermediate 2.01). White solid, MS: 1067.7 $[M+H]^+$.

Intermediate 1.03 tert-Butyl 3-{[(11S,14S,17S)-22-bromo-11,14-bis(3-{[(tert-butoxy)carbonyl]amino}propyl)-25-chloro-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate

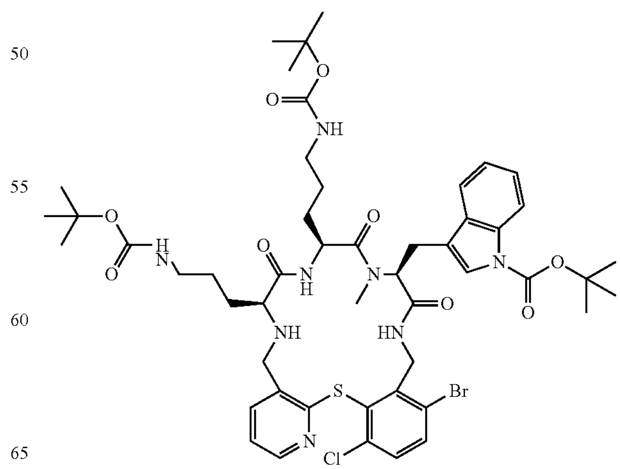

The title compound was produced according to the General procedure for Peptide Macrocycle Synthesis, using 1-[(1,1-dimethylethoxy)carbonyl]-N-[(9H-fluoren-9-ylmethoxy)carbonyl]-N-methyl-L-tryptophan [CAS-RN 197632-75-0] as the first amino acid, $N^5$-[(1,1-dimethylethoxy)carbonyl]-$N^2$-[(9H-fluoren-9-ylmethoxy)carbonyl]-L-ornithine [CAS-RN 109425-55-0] as the second amino acid, $N^5$-[(1,1-dimethylethoxy)carbonyl]-$N^2$-[(9H-fluoren-9-ylmethoxy)carbonyl]-L-ornithine (CAS-RN 109425-55-0) as the third amino acid, and 9H-fluoren-9-ylmethyl N-[[6-bromo-3-chloro-2-[(3-formyl-2-pyridyl)sulfanyl]phenyl]methyl]carbamate [CAS-RN 2097290-48-5] as the tether. White solid, MS: 1069.8 $[M+H]^+$.

Intermediate 1.04 tert-Butyl 3-{[(11S,14S,17S)-22-bromo-11,14-bis(3-{[(tert-butoxy)carbonyl]amino}propyl)-25-fluoro-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate

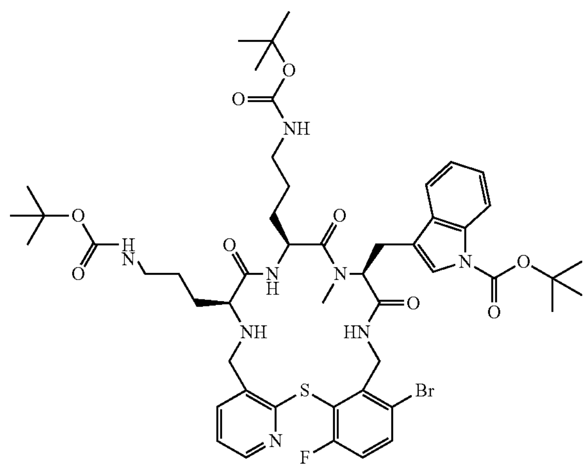 [SMILES: CN1C(=O)[C@H](CCCNC(=O)OC(C)(C)C)NC(=O)[C@H](CCCNC(=O)OC(C)(C)C)NCc2cccnc2Sc2c(F)ccc(Br)c2CNC(=O)[C@@H]1Cc1cn(C(=O)OC(C)(C)C)c2ccccc12]

The title compound was produced in analogy to intermediate 1.03, replacing 9H-fluoren-9-ylmethyl N-[[6-bromo-3-chloro-2-[(3-formyl-2-pyridyl)sulfanyl]phenyl]methyl]carbamate by (9H-fluoren-9-yl)methyl 6-bromo-3-fluoro-2-((3-formylpyridin-2-yl)thio)benzylcarbamate (intermediate 2.01). White solid, MS: 1053.7 $[M+H]^+$.

Intermediate 1.05 tert-Butyl 3-{[(11S,14S,17S)-22-bromo-14-(4-{[(tert-butoxy)carbonyl]amino}butyl)-25-chloro-16-methyl-12,15,18-trioxo-11-{2-[(triphenylmethyl)carbamoyl]ethyl}-2-thia-4,10,13,16,19-pentaazatricyclo[19.4.0.0^{3,8}]pentacosa-1(25),3(8),4,6,21,23-hexaen-17-yl]methyl}-1H-indole-1-carboxylate

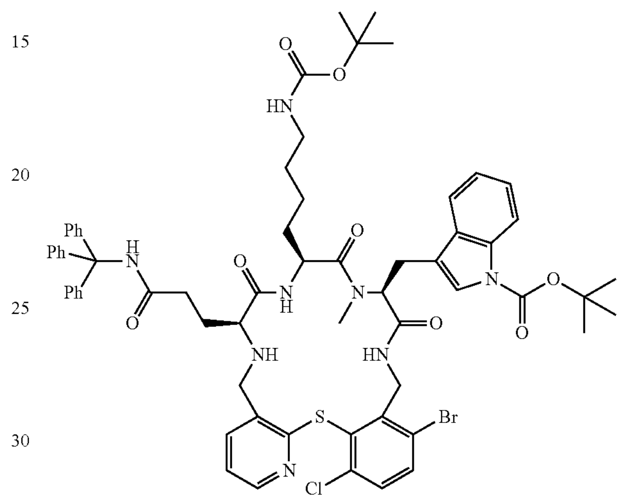

The title compound was produced according to the General procedure for Peptide Macrocycle Synthesis, using 1-[(1,1-dimethylethoxy)carbonyl]-N-[(9H-fluoren-9-ylmethoxy)carbonyl]-N-methyl-L-tryptophan [CAS-RN 197632-75-0] as the first amino acid, $N^6$-[(1,1-dimethylethoxy)carbonyl]-$N^2$-[(9H-fluoren-9-ylmethoxy)carbonyl]-L-lysine (CAS-RN 71989-26-9) as the second amino acid, $N^2$-[(9H-fluoren-9-ylmethoxy)carbonyl]-N-(triphenylmethyl)-L-glutamine [CAS-RN 132327-80-1] as the third amino acid, and 9H-fluoren-9-ylmethyl N-[[6-bromo-3-chloro-2-[(3-formyl-2-pyridyl)sulfanyl]phenyl]methyl]carbamate [CAS-RN 2097290-48-5] as the tether. White solid, MS: 1239.9 $[M+H]^+$.

Intermediate 1.06 tert-Butyl 3-(((7S,10S,13S)-17-bromo-10-(4-((tert-butoxycarbonyl)amino)butyl)-7-(3-((tert-butoxycarbonyl)amino)propyl)-12,20-dimethyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate

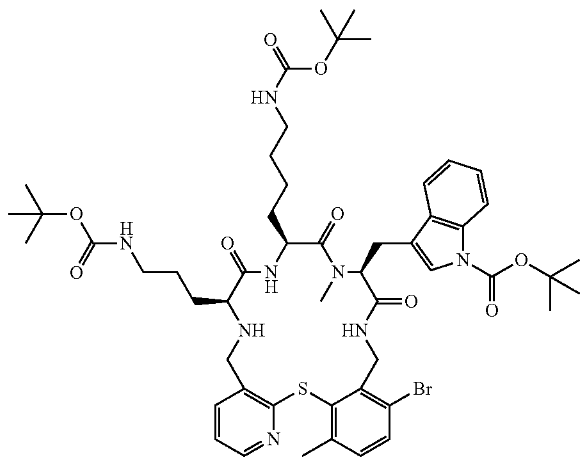 [SMILES: Cc1ccc(Br)c2c1Sc1ncccc1CN[C@@H](CCCNC(=O)OC(C)(C)C)C(=O)N[C@@H](CCCCNC(=O)OC(C)(C)C)C(=O)N(C)[C@@H](Cc1cn(C(=O)OC(C)(C)C)c3ccccc13)C(=O)NC2]

The title compound was produced in analogy to intermediate 1, replacing 9H-fluoren-9-ylmethyl N-[[2-bromo-6-[(3-formyl-2-pyridyl)sulfanyl]phenyl]methyl]carbamate by 9H-fluoren-9-ylmethyl N-[[6-bromo-2-[(3-formyl-2-pyridyl)sulfanyl]-3-methyl-phenyl]methyl]carbamate (intermediate 2.02). White solid, MS: 1063.6 $[M+H]^+$.

Intermediate 1.07 tert-Butyl 3-{[(11S,14S,17S)-22-bromo-14-(4-{[(tert-butoxy)carbonyl]amino}butyl)-11-(2-{[(tert-butoxy)carbonyl]amino}ethyl)-25-chloro-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate

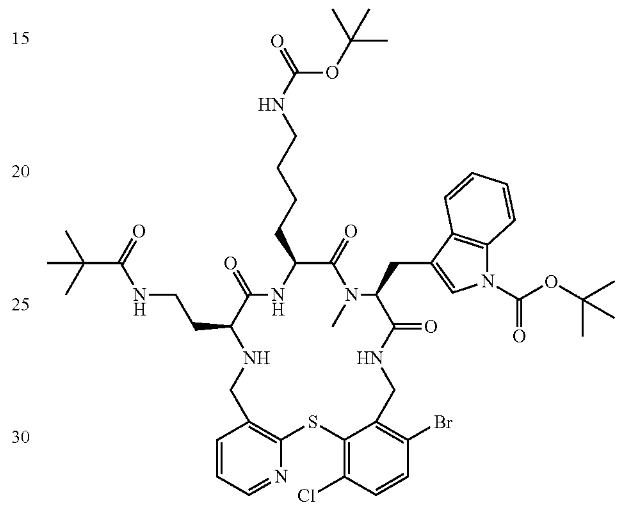

The title compound was produced according to the General procedure for Peptide Macrocycle Synthesis, using 1-[(1,1-dimethylethoxy)carbonyl]-N-[(9H-fluoren-9-ylmethoxy)carbonyl]-N-methyl-L-tryptophan [CAS-RN 197632-75-0] as the first amino acid, $N^6$-[(1,1-dimethylethoxy)carbonyl]-$N^2$-[(9H-fluoren-9-ylmethoxy)carbonyl]-L-lysine [CAS-RN 71989-26-9] as the second amino acid, (S)-4-[[(1,1-dimethylethoxy)carbonyl]amino]-2-[[(9H-fluoren-9-ylmethoxy)carbonyl]amino]-butanoic acid [CAS-RN 125238-99-5] as the third amino acid, and 9H-fluoren-9-ylmethyl N-[[6-bromo-3-chloro-2-[(3-formyl-2-pyridyl)sulfanyl]phenyl]methyl]carbamate [CAS-RN 2097290-48-5] as the tether. White solid, MS: 1069.8 $[M+H]^+$.

Intermediate 1.08 tert-Butyl 3-{[(11S,14S,17S)-22-bromo-11-(2-{[(tert-butoxy)carbonyl]amino}ethyl)-14-(3-{[(tert-butoxy)carbonyl]amino}propyl)-25-chloro-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate

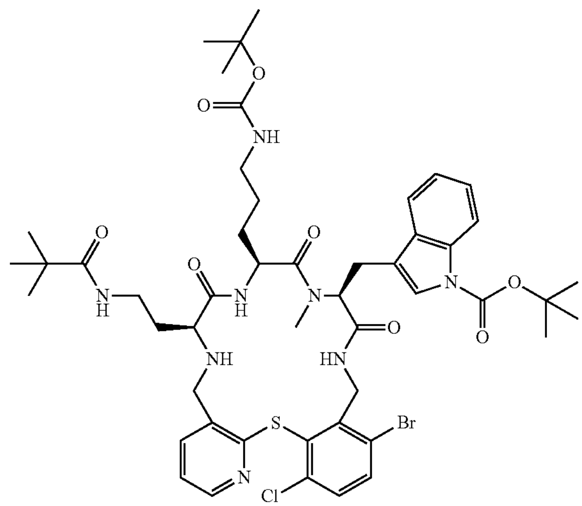 [SMILES: CN1C(=O)[C@H](CCCNC(=O)OC(C)(C)C)NC(=O)[C@H](CCNC(=O)C(C)(C)C)NCc2cccnc2Sc2c(Cl)ccc(Br)c2CNC(=O)[C@@H]1Cc1cn(C(=O)OC(C)(C)C)c2ccccc12]

The title compound was produced according to the General procedure for Peptide Macrocycle Synthesis, using 1-[(1,1-dimethylethoxy)carbonyl]-N-[(9H-fluoren-9-ylmethoxy)carbonyl]-N-methyl-L-tryptophan [CAS-RN 197632-75-0] as the first amino acid, $N^5$-[(1,1-dimethylethoxy)carbonyl]-$N^2$-[(9H-fluoren-9-ylmethoxy)carbonyl]-L-ornithine [CAS-RN 109425-55-0] as the second amino acid, (S)-4-[[(1,1-dimethylethoxy)carbonyl]amino]-2-[[(9H-fluoren-9-ylmethoxy)carbonyl]amino]-butanoic acid [CAS-RN 125238-99-5] as the third amino acid, and 9H-fluoren-9-ylmethyl N-[[6-bromo-3-chloro-2-[(3-formyl-2-pyridyl)sulfanyl]phenyl]methyl]carbamate [CAS-RN 2097290-48-5] as the tether. White solid, MS: 1055.8 $[M+H]^+$.

Intermediate 1.09 tert-Butyl 3-(((7S,10S,13S)-17-bromo-10-(4-((tert-butoxycarbonyl)amino)-3,3-difluorobutyl)-7-(3-((tert-butoxycarbonyl)amino)propyl)-20-chloro-12-methyl-8,11,14-trioxo-5,6,7,8,9,10,11,12,13,14,15,16-dodecahydrobenzo[b]pyrido[3,2-p][1,5,8,11,14]thiatetraazacycloheptadecin-13-yl)methyl)-1H-indole-1-carboxylate

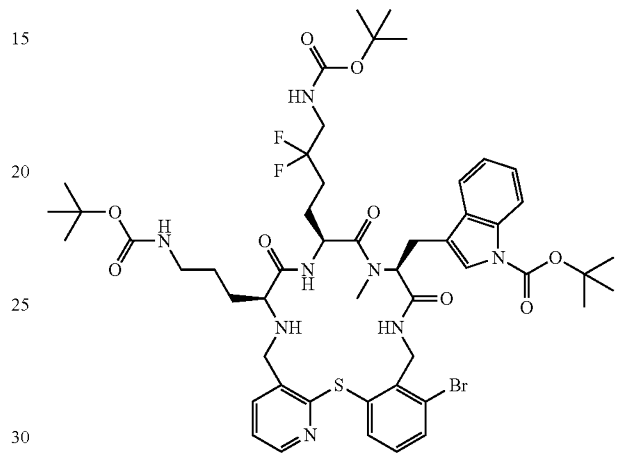

The title compound was produced according to the General procedure for Peptide Macrocycle Synthesis, using 1-[(1,1-dimethylethoxy)carbonyl]-N-[(9H-fluoren-9-ylmethoxy)carbonyl]-N-methyl-L-tryptophan [CAS-RN 197632-75-0] as the first amino acid, (2S)-6-(tert-butoxycarbonylamino)-2-(9H-fluoren-9-ylmethoxycarbonylamino)-5,5-difluoro-hexanoic acid (intermediate 5) as the second amino acid, $N^5$-[(1,1-dimethylethoxy)carbonyl]-$N^2$-[(9H-fluoren-9-ylmethoxy)carbonyl]-L-ornithine [CAS-RN 109425-55-0] as the third amino acid, and 9H-fluoren-9-ylmethyl N-[[6-bromo-3-chloro-2-[(3-formyl-2-pyridyl)sulfanyl]phenyl]methyl]carbamate [CAS-RN 2097290-48-5] as the tether. White solid, MS: 1119.1 $[M+H]^+$.

Intermediate 1.10 tert-Butyl 3-{[(11S,14S,17S)-22-bromo-14-(4-{[(tert-butoxy)carbonyl]amino}butyl)-11-(3-{[(tert-butoxy)carbonyl]amino}propyl)-25-methoxy-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate

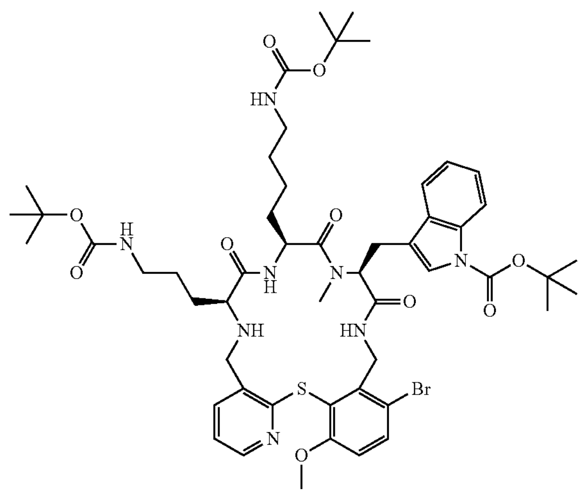 [SMILES: COc1ccc(Br)c2c1Sc1ncccc1CN[C@@H](CCCNC(=O)OC(C)(C)C)C(=O)N[C@@H](CCCCNC(=O)OC(C)(C)C)C(=O)N(C)[C@@H](Cc1cn(C(=O)OC(C)(C)C)c3ccccc13)C(=O)NC2]

The title compound was produced in analogy to intermediate 1, replacing 9H-fluoren-9-ylmethyl N-[[2-bromo-6-[(3-formyl-2-pyridyl)sulfanyl]phenyl]methyl]carbamate by 9H-fluoren-9-ylmethyl N-[[6-bromo-2-[(3-formyl-2-pyridyl)sulfanyl]-3-methoxy-phenyl]methyl]carbamate (intermediate 2.03). Off-white solid, MS: 1079.8 [M+H]$^+$.

Intermediate 1.11 tert-Butyl 3-{[(11S,14S,17S)-22-bromo-]4-(4-{[(tert-butoxy)carbonyl]amino}butyl)-11-(3-{[(tert-butoxy)carbonyl]amino}propyl)-25-chloro-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-2-methyl-1H-indole-1-carboxylate

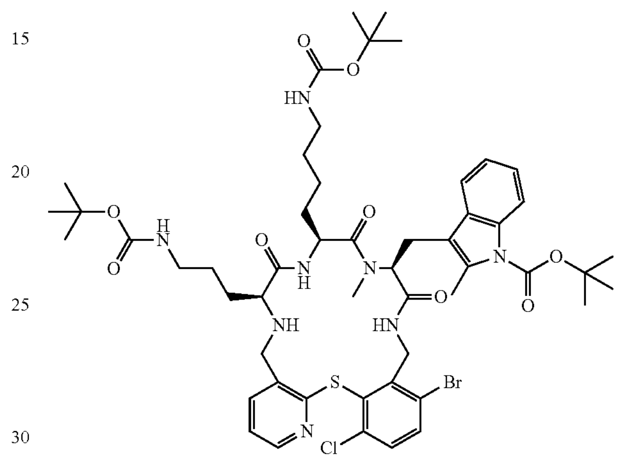

The title compound was produced according to the General procedure for Peptide Macrocycle Synthesis, using (2S)-2-[9H-fluoren-9-ylmethoxycarbonyl(methyl)amino]-3-[2-methyl-1-[(2-methylpropan-2-yl)oxycarbonyl]indol-3-yl]propanoic acid (intermediate 4) as the first amino acid, $N^6$-[(1,1-dimethylethoxy)carbonyl]-$N^2$-[(9H-fluoren-9-ylmethoxy)carbonyl]-L-lysine [CAS-RN 71989-26-9] as the second amino acid, $N^5$-[(1,1-dimethylethoxy)carbonyl]-$N^2$-[(9H-fluoren-9-ylmethoxy)carbonyl]-L-ornithine [CAS-RN 109425-55-0] as the third amino acid, and 9H-fluoren-9-ylmethyl N-[[6-bromo-3-chloro-2-[(3-formyl-2-pyridyl)sulfanyl]phenyl]methyl]carbamate [CAS-RN 2097290-48-5] as the tether. White solid, MS: 1097.5 [M+H]$^+$.

Intermediate 1.12 tert-Butyl 3-{[(11S,14S,17S)-22-bromo-14-(4-{[(tert-butoxy)carbonyl]amino}butyl)-11-(3-{[(tert-butoxy)carbonyl]amino}propyl)-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-2-methyl-1H-indole-1-carboxylate

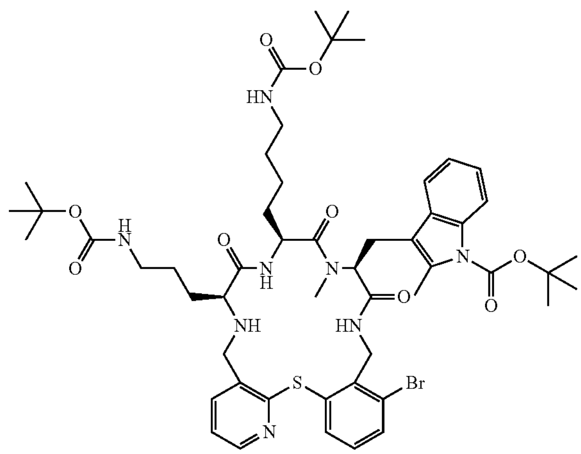 [SMILES: Cc1c(C[C@H]2C(=O)NCc3c(Br)cccc3Sc3ncccc3CN[C@@H](CCCNC(=O)OC(C)(C)C)C(=O)N[C@@H](CCCCNC(=O)OC(C)(C)C)C(=O)N2C)c2ccccc2n1C(=O)OC(C)(C)C]

The title compound was produced according to the General procedure for Peptide Macrocycle Synthesis, using (2S)-2-[9H-fluoren-9-ylmethoxycarbonyl(methyl)amino]-3-[2-methyl-1-[(2-methylpropan-2-yl)oxycarbonyl]indol-3-yl]propanoic acid (intermediate 4) as the first amino acid, $N^6$-[(1,1-dimethylethoxy)carbonyl]-$N^2$-[(9H-fluoren-9-ylmethoxy)carbonyl]-L-lysine [CAS-RN 71989-26-9] as the second amino acid, $N^5$-[(1,1-dimethylethoxy)carbonyl]-$N^2$-[(9H-fluoren-9-ylmethoxy)carbonyl]-L-ornithine [CAS-RN 109425-55-0] as the third amino acid, and 9H-fluoren-9-ylmethyl N-[[2-bromo-6-[(3-formyl-2-pyridyl)sulfanyl]phenyl]methyl]carbamate (intermediate 2) as the tether. White solid, MS: 1063.7 [M+H]$^+$.

Intermediate 1.13 tert-Butyl 3-{[(11S,14S,17S)-22-bromo-14-(2-{[(tert-butoxy)carbonyl]amino}ethyl)-11-(3-{[(tert-butoxy)carbonyl]amino}propyl)-25-chloro-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate

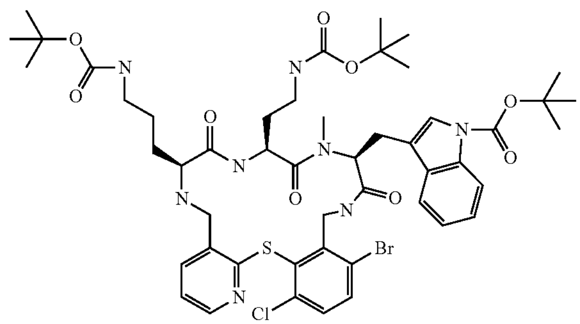 [SMILES: CN1C(=O)[C@H](CCNC(=O)OC(C)(C)C)NC(=O)[C@H](CCCNC(=O)OC(C)(C)C)NCc2cccnc2Sc2c(Cl)ccc(Br)c2CNC(=O)[C@@H]1Cc1cn(C(=O)OC(C)(C)C)c2ccccc12]

The title compound was produced according to the General procedure for Peptide Macrocycle Synthesis, using 1-[(1,1-dimethylethoxy)carbonyl]-N-[(9H-fluoren-9-ylmethoxy)carbonyl]-N-methyl-L-tryptophan [CAS-RN 197632-75-0] as the first amino acid, (S)-4-[[(1,1-dimethylethoxy)carbonyl]amino]-2-[[(9H-fluoren-9-ylmethoxy)carbonyl]amino]-butanoic acid [CAS-RN 125238-99-5] as the second amino acid, $N^5$-[(1,1-dimethylethoxy)carbonyl]-$N^2$-[(9H-fluoren-9-ylmethoxy)carbonyl]-L-ornithine [CAS-RN 109425-55-0] as the third amino acid, and 9H-fluoren-9-ylmethyl N-[[6-bromo-3-chloro-2-[(3-formyl-2-pyridyl)sulfanyl]phenyl]methyl]carbamate [CAS-RN 2097290-48-5] as the tether. White solid, MS: 1056.0 [M+H]$^+$.

Intermediate 1.14 tert-Butyl 3-{[(11S,14S,17S)-22-bromo-11,14-bis(3-{[(tert-butoxy)carbonyl]amino}propyl)-16-methyl-12,15,18-trioxo-2-thia-4,10,13,16,19-pentaazatricyclo[19.4.0.0^{3,8}]pentacosa-1(21),3,5,7,22,24-hexaen-17-yl]methyl}-1H-indole-1-carboxylate

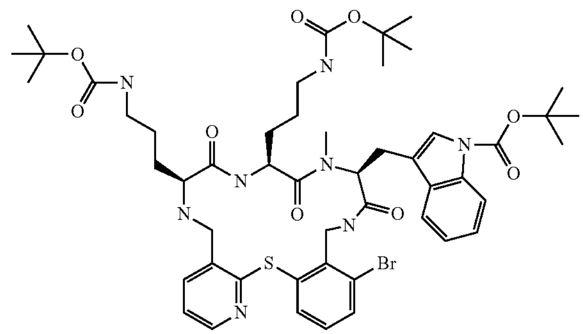 [SMILES: CN1C(=O)[C@H](CCCNC(=O)OC(C)(C)C)NC(=O)[C@H](CCCNC(=O)OC(C)(C)C)NCc2cccnc2Sc2cccc(Br)c2CNC(=O)[C@@H]1Cc1cn(C(=O)OC(C)(C)C)c2ccccc12]

The title compound was produced according to the General procedure for Peptide Macrocycle Synthesis, using 1-[(1,1-dimethylethoxy)carbonyl]-N-[(9H-fluoren-9-ylmethoxy)carbonyl]-N-methyl-L-tryptophan [CAS-RN 197632-75-0] as the first amino acid, $N^5$-[(1,1-dimethylethoxy)carbonyl]-$N^2$-[(9H-fluoren-9-ylmethoxy)carbonyl]-L-ornithine [CAS-RN 109425-55-0] as the second amino acid, $N^5$-[(1,1-dimethylethoxy)carbonyl]-$N^2$-[(9H-fluoren-9-ylmethoxy)carbonyl]-L-ornithine [CAS-RN 109425-55-0] as the third amino acid, and 9H-fluoren-9-ylmethyl N-[[6-bromo-3-chloro-2-[(3-formyl-2-pyridyl)sulfanyl]phenyl]methyl]carbamate [CAS-RN 2097290-48-5] as the tether. White solid, MS: 1035.5 [M+H]$^+$.

Intermediate 1.15 tert-butyl 3-{[(11S,14S,17S)-22-bromo-14-(4-{[(tert-butoxy)carbonyl]amino}butyl)-11-(3-{[(tert-butoxy)carbonyl]amino}propyl)-16-methyl-12,15,18-trioxo-2-thia-4,10,13,16,19,24-hexaazatricyclo[19.4.0.0^{3,8}]pentacosa-1(21),3,5,7,22,24-hexaen-17-yl]methyl}-1H-indole-1-carboxylate

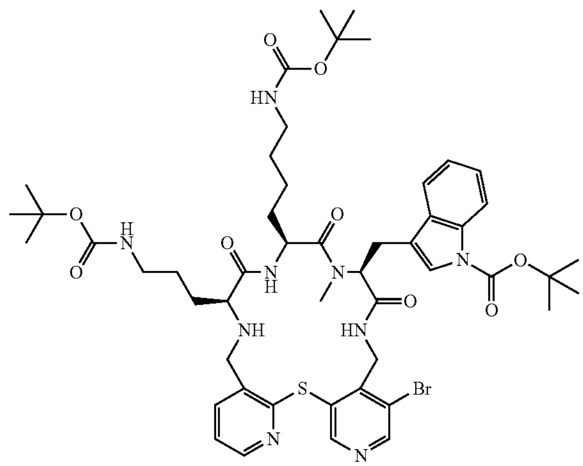 [SMILES: CN1C(=O)[C@H](CCCCNC(=O)OC(C)(C)C)NC(=O)[C@H](CCCNC(=O)OC(C)(C)C)NCc2cccnc2Sc2cncc(Br)c2CNC(=O)[C@@H]1Cc1cn(C(=O)OC(C)(C)C)c2ccccc12]

The title compound was produced according to the General procedure for Peptide Macrocycle Synthesis, using 1-[(1,1-dimethylethoxy)carbonyl]-N-[(9H-fluoren-9-ylmethoxy)carbonyl]-N-methyl-L-tryptophan [CAS-RN 197632-75-0] as the first amino acid, $N^6$-[(1,1-dimethylethoxy)carbonyl]-$N^2$-[(9H-fluoren-9-ylmethoxy)carbonyl]-L-lysine [CAS-RN 71989-26-9] as the second amino acid, $N^5$-[(1,1-dimethylethoxy)carbonyl]-$N^2$-[(9H-fluoren-9-ylmethoxy)carbonyl]-L-ornithine [CAS-RN 109425-55-0] as the third amino acid, and 9H-fluoren-9-ylmethyl N-[[3-bromo-5-[(3-formyl-2-pyridyl)sulfanyl]-4-pyridyl]methyl] carbamate (intermediate 2.04) as the tether. White solid, MS: 1050.8 [M+H]$^+$.

Intermediate 2

9H-Fluoren-9-ylmethyl N-[[2-bromo-6-[(3-formyl-2-pyridyl)sulfanyl]phenyl]methyl]carbamate

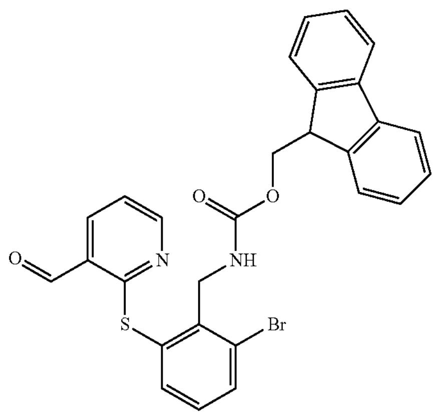 [SMILES: O=Cc1cccnc1Sc1cccc(Br)c1CNC(=O)OCC1c2ccccc2-c2ccccc21]

Step 1: Methyl 2-(3-bromo-2-formyl-phenyl)sulfanylpyridine-3-carboxylate

To a stirred solution of 2-bromo-6-fluorobenzaldehyde (37.0 g, 182 mmol) in N,N-dimethylformamide (370 mL) was added potassium tert-butylate (40.9 g, 365 mmol) and reaction mass was stirred at 25° C. for 30 min. Then, 2-mercaptonicotinic acid (CAS-RN38521-46-9; 31.1 g, 200 mmol) was added and reaction mixture was stirred at 80° C. for 4 h. After cooling to room temperature potassium carbonate (75.5 g, 547 mmol) was added followed by addition of iodomethane (77.6 g, 547 mmol), then after 16 h the reaction mixture was partitioned between ethyl acetate and water. The separated organic layer was washed with brine, dried over sodium sulfate, filtered, and evaporated under reduced pressure. Chromatrography (silica gel; hexane/dichlormethane 85:15) produced the title compound (27.5 g, 43%). Yellow solid, MS: 351.9 [M+H]$^+$.

Step 2: Ethyl 2-[3-bromo-2-[(E)-tert-butylsulfinyliminomethyl]phenyl]sulfanylpyridine-3-carboxylate To a stirred solution of methyl 2-(3-bromo-2-formyl-phenyl)sulfanylpyridine-3-carboxylate (27.0 g, 76.7 mmol) in tetrahydrofuran (270 mL) was added 2-methyl-2-propanesulfinamide (CAS-RN 146374-27-8; 9.29 g, 76.7 mmol), titanium ethoxide (73.9 g, 384 mmol), and the reaction mixture was heated at 70° C. for 4 h. After cooling the reaction mixture was treated with brine, then insoluble material was removed by filtration through diatomaceous earth. The filtrate was extracted with ethyl acetate, the separated organic layer was washed with water, dried over sodium sulfate and evaporated under reduced pressure to afford the title compound (28.5 g, 79%) as yellow gum.

Step 3: N-[[2-Bromo-6-[[3-(hydroxymethyl)-2-pyridyl]sulfanyl]phenyl]methyl]-2-methyl-propane-2-sulfinamide To a stirred solution of ethyl 2-[3-bromo-2-[(E)-tert-butylsulfinyliminomethyl]phenyl]sulfanylpyridine-3-carboxylate (28.4 g, 60.5 mmol) in tetrahydrofuran (284 mL) was added lithium aluminumhydride solution (2.5 M in tetrahydrofuran, 48.4 mL, 121 mmol) at −40° C. and reaction mixture was stirred at −40° C. for 2 h, then excess reagent was destroyed by addition of sat. aq. sodium sulfate solution. The reaction mixture was extracted with ethyl acetate, the organic layer was washed with brine, dried over sodium sulfate, filtered, and evaporated to produce the title compound (22.6 g, 87%) as a yellow semisolid.

Step 4: [2-[2-(Aminomethyl)-3-bromo-phenyl]sulfanyl-3-pyridyl]methanol hydrochloride To a stirred solution of N-[[2-bromo-6-[[3-(hydroxymethyl)-2-pyridyl]sulfanyl]phenyl]methyl]-2-methyl-propane-2-sulfinamide (58.0 g, 135 mmol) in tetrahydrofuran (550 mL) and methanol (10 mL) was added hydrogen chloride solution (4 M in 1,4-dioxane, 67.5 mL, 270 mmol) at room temperature, then after 2 h the reaction mixture was concentrated to produce the title compound (46.1 g, 94%) as an off-white solid.

Step 5: 9H-Fluoren-9-ylmethyl N-[[2-bromo-6-[[3-(hydroxymethyl)-2-pyridyl]sulfanyl]phenyl]methyl] carbamate To a stirred suspension of [2-[2-(aminomethyl)-3-bromo-phenyl]sulfanyl-3-pyridyl]methanol hydrochloride (46 g, 127 mmol) in 5% aq. sodium hydrogencarbonate solution (150 mL) was added (fluorenylmethoxycarbonyl)hydroxysuccinimide ester (CAS-RN 82911-69-1; 51.5 g, 153 mmol) in 1,4-dioxane (25 mL) at room temperature, then after 15 h the reaction mixture was partitioned between water and dichloromethane/methanol 9:1. The organic layer was washed with brine, dried over sodium sulfate, filtered, and evaporated. Chromatography (silica gel; dichloromethane/ethyl acetate 19:1) produced the title compound (34.3 g, 49% yield) as off-white solid.

Step 6: 9H-Fluoren-9-ylmethyl N-[[2-bromo-6-[(3-formyl-2-pyridyl)sulfanyl]phenyl]-methyl]carbamate To a solution of 9H-fluoren-9-ylmethyl N-[[2-bromo-6-[[3-(hydroxymethyl)-2-pyridyl]sulfanyl]phenyl]methyl]carbamate (16.0 g, 29.2 mmol) in dichloromethane (160 mL) was added 1,1,1-tris(acetyloxy)-1,1-dihydro-1,2-benziodoxol-3(1H)-one (CAS-RN 87413-09-0; 18.6 g, 43.8 mmol) at 0° C., then the reaction mixture was allowed to reach room temperature over 1 h. The reaction mixture was partitioned between sat. aq. sodium hydrogencarbonate and dichloromethane. The organic layer was washed with water and brine, dried over sodium sulfate, filtered, and concentrated. Chromatography (silica gel; dichloromethane/ethyl acetate 19:1) produced the title compound (11.9 g, 68% yield). Off-white solid, MS: 545.2 $[M+H]^+$.

The following intermediates were produced in analogy to intermediate 2, replacing 2-bromo-6-fluorobenzaldehyde by the appropriate aldehyde.

| No. | Systematic Name | Aldehyde | MS (m/z) |
|---|---|---|---|
| 2.00 | 9H-fluoren-9-ylmethyl N-[[2-bromo-6-[(3-formyl-2-pyridyl)sulfanyl]phenyl]methyl]carbamate | 2-bromo-6-fluoro-5-methylbenzaldehyde | 545.2 $[M + H]^+$ |
| 2.01 | (9H-fluoren-9-yl)methyl 6-bromo-3-fluoro-2-((3-formylpyridin-2-yl)thio)benzylcarbamate | 5-bromo-2,3-difluorobenzaldehyde | 563.1 $[M + H]^+$ |
| 2.02 | 9H-fluoren-9-ylmethyl N-[[6-bromo-2-[(3-formyl-2-pyridyl)sulfanyl]-3-methyl-phenyl]methyl]carbamate | 6-bromo-2-fluoro-3-methylbenzaldehyde | 559.2 $[M + H]^+$ |
| 2.03 | 9H-fluoren-9-ylmethyl N-[[6-bromo-2-[(3-formyl-2-pyridyl)sulfanyl]-3-methoxy-phenyl]methyl]carbamate | 6-bromo-2-fluoro-3-methoxy-benzaldehyde | 575.1 $[M + H]^+$ |
| 2.04 | 9H-fluoren-9-ylmethyl N-[[3-bromo-5-[(3-formyl-2-pyridyl)sulfanyl]-4-pyridyl]methyl]carbamate | 3,5-dibromo-4-pyridinecarboxaldehyde | 546.1 $[M + H]^+$ |

Intermediate 3

9H-Fluoren-9-ylmethyl N-[[6-bromo-3-chloro-2-(3-formylpyrazin-2-yl)sulfanyl-phenyl]methyl]carbamate

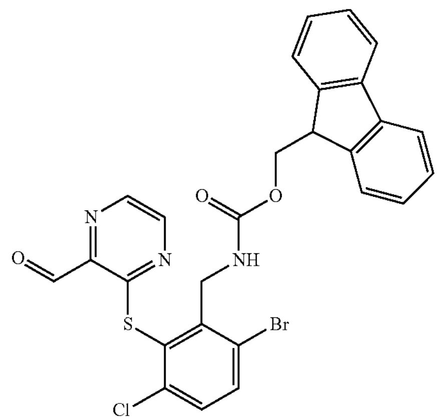 [SMILES: O=Cc1nccnc1Sc1c(Cl)ccc(Br)c1CNC(=O)OCC1c2ccccc2-c2ccccc21]

The title compound was produced in analogy to intermediate 2, replacing 2-bromo-6-fluorobenzaldehyde in step 1 by 6-bromo-3-chloro-2-fluorobenzaldehyde and 2-mercaptonicotinic acid in step 1 by 3,4-dihydro-3-thioxo-2-pyrazinecarboxylic acid [CAS-RN 36931-81-4]. White solid, MS: 580.0 $[M+H]^+$.

Intermediate 4

(2S)-2-[9H-Fluoren-9-ylmethoxycarbonyl(methyl)amino]-3-[2-methyl-]-[(2-methylpropan-2-yl)oxycarbonyl]indol-3-yl]propanoic acid

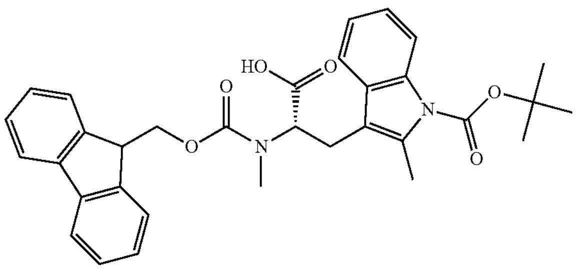 [SMILES: Cc1c(C[C@@H](C(=O)O)N(C)C(=O)OCC2c3ccccc3-c3ccccc32)c2ccccc2n1C(=O)OC(C)(C)C]

Step 1: tert-Butyl 3-[(1Z)-2-{[(benzyloxy)carbonyl]amino}-3-methoxy-3-oxoprop-1-en-1-yl]-2-methyl-1H-indole-1-carboxylate To a stirred solution of (±)-benzyloxycarbonyl-alpha-phosphonoglycine trimethyl ester (CAS-RN 88568-95-0; 28.7 g, 86.9 mmol) in dichloromethane (250 mL) was added 1,8-diazabicyclo[5.4.0]undec-7-ene (13.2 g, 86.7 mmol) at room temperature. After 10 min, a solution of tert-butyl 3-formyl-2-methyl-1H-indole-1-carboxylate (CAS-RN 885524-92-5; 15.0 g, 57.9 mmol) in dichloromethane (50 mL) was added, then after 16 h the reaction mixture was concentrated under reduced pressure. The residue was partitioned between ethyl acetate and sat. aq. sodium hydrogencarbonate solution, the organic layer was washed with water and brine, dried over sodium sulfate, filtered, and evaporated. Chromatography (silica gel; hexane-ethyl acetate gradient) produced the title compound (22 g, 81%). Off-white solid, MS: 465.2 [M+H]$^+$.

Step 2: tert-Butyl 3-[(2S)-2-(benzyloxycarbonylamino)-3-methoxy-3-oxo-propyl]-2-methyl-indole-1-carboxylate In a glove box (<2 ppm $O_2$) tert-butyl 3-[(1Z)-2-{[(benzyloxy)carbonyl]amino}-3-methoxy-3-oxoprop-1-en-1-yl]-2-methyl-1H-indole-1-carboxylate (10.5 g, 22 mmol), [(1,2,5,6-η)-1,5-cyclooctadiene][(2S,2'S,5S,5'S)-1,1'-(1,2-phenylene)bis[2,5-diethylphospholane-κP]]-rhodium(1+) trifluoromethanesulfonate (CAS-RN 142184-30-3; 107 mg, 0.148 mmol) and methanol (100 mL) were combined in a steel autoclave. The orange-yellow solution was flushed three times with hydrogen (18 bar), then stirred at 30° C. for 24 h under a hydrogen atmosphere (50 bar), then the reaction mixture was concentrated under vacuum. The residue was dissolved in ethyl acetate (100 mL) and treated with activated carbon (1.5 g), stirred for 1 h, then filtered through a silica gel pad. After evaporation of the solvent the title compound (10.5 g, 100%; enantiomeric ratio 97.1:2.9) was obtained. Light yellow viscous oil, MS: 467.2 [M+H]$^+$.

Step 3: tert-Butyl 3-[(2S)-2-amino-3-methoxy-3-oxopropyl]-2-methyl-1H-indole-1-carboxylate To a degassed solution of tert-butyl 3-[(2S)-2-{[(benzyloxy)carbonyl]amino}-3-methoxy-3-oxopropyl]-2-methyl-1H-indole-1-carboxylate (18.3 g, 39.2 mmol) in methanol (200 mL) was added palladium (10% on activated carbon, 3.5 g) at 25° C. and the reaction mixture was stirred under a hydrogen atmosphere (1 bar) for 6 h, then filtered through diatomaceous earth. The filtrate was evaporated to produce the title compound (12.5 g, 95%). Colourless sticky oil, MS: 333.2 [M+H]$^+$.

Step 4: tert-Butyl 3-[(2S)-3-methoxy-2-[(2-nitrobenzene)sulfonamido]-3-oxopropyl]-2-methyl-1H-indole-1-carboxylate To a solution of tert-butyl 3-[(2S)-2-amino-3-methoxy-3-oxopropyl]-2-methyl-1H-indole-1-carboxylate (13.0 g, 39.1 mmol) in mixture of sat. aq. sodium bicarbonate solution (300 mL) and dioxane (300 mL) was added 2-nitrobenzenesulfonylchloride (10.4 g, 46.9 mmol) and reaction mixture was stirred at 25° C. for 16 h. After completion of the reaction, pH of the aqueous solution was adjusted to 7.0 using 0.5 M aq. hydrochloric acid solution and extracted with ethyl acetate. The organic layer was washed with water and brine; dried over sodium sulfate and concentrated under reduced pressure. Chromatography (silica gel; hexane-ethyl acetate gradient) produced the title compound (17.5 g, 86%). Yellow sticky solid, MS: 518.4 [M+H]$^+$.

Step 5: tert-Butyl 3-[(2S)-3-methoxy-2-[N-methyl(2-nitrobenzene)sulfonamido]-3-oxopropyl]-2-methyl-1H-indole-1-carboxylate To a stirred mixture of tert-butyl 3-[(2S)-3-methoxy-2-[(2-nitrobenzene)sulfonamido]-3-oxopropyl]-2-methyl-1H-indole-1-carboxylate (17.5 g, 33.8 mmol) and potassium carbonate (16.4 g, 118 mmol) in N,N-dimethylformamide (150 mL) was added methyl iodide (24.0 g, 169 mmol) and stirred at 25° C. for 16 h. After completion of the reaction, it was poured into cold water and solid obtained was filtered, washed repeatedly with water followed by hexanes and finally dried under high vacuum the title compound (15 g, 83%). Pale yellow solid, MS: 532.2 [M+H]$^+$.

Step 6: tert-Butyl 3-[(2S)-3-methoxy-2-(methylamino)-3-oxopropyl]-2-methyl-1H-indole-1-carboxylate To a solution of tert-butyl 3-[(2S)-3-methoxy-2-[N-methyl(2-nitrobenzene)sulfonamido]-3-oxopropyl]-2-methyl-1H-indole-1-carboxylate (14.0 g, 26.3 mmol) in N,N-dimethylformamide (140 mL) were added thiophenol (3.48 g, 31.6 mmol) and potassium carbonate (11.0 g, 79.0 mmol). The reaction mixture was stirred at room temperature for 2 h, then partitioned between water and ethyl acetate. The organic layer was washed with brine, dried over sodium sulfate, filtered, and evaporated. Chromatography (silica gel; hexane/ethyl acetate 1:3) produced the title compound (7.3 g, 80%). Colourless liquid, MS: 346.7 [M+H]$^+$.

Step 7: (2S)-3-{1-[(tert-Butoxy)carbonyl]-2-methyl-1H-indol-3-yl}-2-(methylamino)propanoic acid To a solution of tert-butyl 3-[(2S)-3-methoxy-2-(methylamino)-3-oxopropyl]-2-methyl-1H-indole-1-carboxylate (14.2 g, 41.0 mmol) in tetrahydrofuran (270 mg) and water (90 mL) was added lithium hydroxide monohydrate (2.0 g, 48.8 mmol) and stirred at 25° C. for 16 h. After completion of the reaction, solvent was evaporated under reduced pressure and the pH of the aqueous solution was adjusted to 3.0 using 0.5 M aq. hydrochloric acid solution. The precipitate was collected by filtration, washed with water and hexane, and dried to produce the title compound (13.5 g, 99%). White solid, MS: 248.2 $[M+H]^+$.

Step 8: (2S)-3-{1-[(tert-Butoxy) carbonyl]-2-methyl-1H-indol-3-yl}-2-{[(9H-fluoren-9-yl-methoxy) carbonyl](methyl)amino}propanoic acid To a solution of (2S)-3-{1-[(tert-butoxy)carbonyl]-2-methyl-1H-indol-3-yl}-2-(methylamino)propanoic acid (13.5 g, 40.6 mmol) in 5% aq. sodium hydrocarbonate solution (200 mL) was added a solution of N-(9-fluorenyl-methyloxycarbonyl)oxysuccinimide (CAS-RN Fmoc-OSu CAS 82911-69-1; 16.5 g, 48.7 mmol) in acetonitrile (200 mL) at 0° C. The reaction mixture was stirred at 25° C. for 16 h, then the organic solvent was evaporated under reduced pressure. The aqueous part was neutralized using 0.5 M aq. hydrochloric acid solution and extracted with ethyl acetate. The organic layer was dried over sodium sulfate, filtered, and evaporated. Chromatography (silica gel; hexane-ethyl acetate gradient) produced the title compound (13.5 g, 60%). White solid, MS: 555.4 $[M+H]^+$.

Intermediate 5

(2S)-6-(tert-Butoxycarbonylamino)-2-(9H-fluoren-9-ylmethoxycarbonylamino)-5,5-difluoro-hexanoic acid

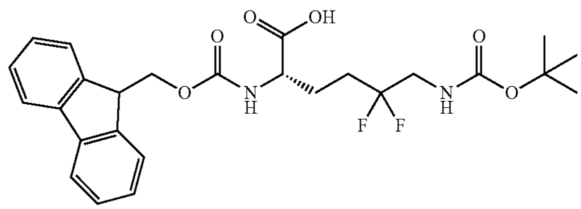 [SMILES: CC(C)(C)OC(=O)NCC(F)(F)CC[C@H](NC(=O)OCC1c2ccccc2-c2ccccc21)C(=O)O]

Step 1: (S)-Methyl 6-azido-2-(((benzyloxy)carbonyl)amino)-5,5-difluorohexanoate

To a solution of (S)-methyl 2-(((benzyloxy)carbonyl) amino)-5,5-difluoro-6-(((trifluoromethyl)sulfonyl)oxy) hexanoate (CAS-RN 667464-89-3; 1.39 g, 3.00 mmol) in N,N-dimethylformamide (15 mL) was added sodium azide (585 mg, 9.00 mmol) in one portion at room temperature. The solution was stirred at 30° C. for 20 h, then partitioned between water and ethyl acetate. The organic layer was dried over sodium sulfate, filtered, and evaporated. Chromatography (heptane-ethyl acetate gradient) produced the title compound (650 mg, 61%), MS: 329 $[M-N_2+H]+$.

Step 2: (S)-Methyl 6-amino-2-(((benzyloxy)carbonyl)amino)-5,5-difluorohexanoate

To a solution of (S)-methyl 6-azido-2-(((benzyloxy)carbonyl)amino)-5,5-difluorohexanoate (1.30 g, 3.65 mmol) in tetrahydrofuran (10.5 mL) was added water (10.5 ml) and triphenylphosphine (1.24 g, 4.74 mmol). The reaction mixture was stirred at room temperature overnight, then partitioned between water and ethyl acetate. The organic layer was dried over sodium sulfate, filtered, and evaporated to produce the title compound (1.21 g, 100%), MS: 331 $[M+H]^+$.

Step 3: (S)-Methyl 2-(((benzyloxy)carbonyl)amino)-6-((tert-butoxycarbonyl)amino)-5,5-difluorohexanoate To a solution of (S)-methyl 6-amino-2-(((benzyloxy)carbonyl)amino)-5,5-difluorohexanoate (991 mg, 3.0 mmol) in tetrahydrofuran (5 mL) and water (5 mL) was added sodium carbonate (191 mg, 1.8 mmol) and di-tert-butyl dicarbonate (720 mg, 3.3 mmol) at room temperature, then after 2 h the reaction mixture was partitioned between sat. aq. sodium hydrogencarbonate solution and ethyl acetate. The organic layer was dried over sodium sulfate, filtered, and evaporated. Chromatography (silica gel; heptane-ethyl acetate gradient) produced the title compound (1.10 g, 85%).

Step 4: (S)-Methyl 2-((((9H-fluoren-9-yl)methoxy) carbonyl)amino)-6-((tert-butoxycarbonyl)amino)-5,5-difluorohexanoate To a solution of (S)-methyl 2-(((benzyloxy)carbonyl) amino)-6-((tert-butoxycarbonyl)amino)-5,5-difluoro-hexanoate (1.20 g, 2.79 mmol) in tetrahydrofuran (20 mL) was added palladium (10% on activated carbon, 0.40 g, 2.8 mmol), and the reaction mixture was stirred under a hydrogen atmosphere (1 bar) for 4 h at room temperature, then insoluble material was removed by filtration. The filtrate was concentrated and the residue was dissolved in tetrahydrofuran (10 mL) and water (10 mL) and treated with sodium carbonate (295 mg, 2.79 mmol) and 9-fluorenylmethyl chloroformate (938 mg, 3.62 mmol). The reaction mixture was stirred at room temperature for 5 h, then extracted with petroleum ether/ethyl acetate 1:1. The organic layer was washed with brine, dried over sodium sulfate, filtered, and concentrated. C. The mixture was extracted with PE/EA=2/1 and washed with brine. Chromatography (silica gel; heptane-ethyl acetate gradient) produced the title compound (1.00 g, 69%), MS: 419 $[M\text{-isobutene-}CO_2+H]^+$.

Step 5: (2S)-6-(tert-Butoxycarbonylamino)-2-(9H-fluoren-9-ylmethoxycarbonylamino)-5,5-difluoro-hexanoic acid To a solution of (S)-methyl 2-((((9H-fluoren-9-yl) methoxy)carbonyl)amino)-6-((tert-butoxycarbonyl)amino)-5,5-difluorohexanoate (1.00 g, 1.93 mmol) in tetrahydrofuran (2 mL) was added 1 M calcium chloride solution (1 M in 2-propanol/water 6:5; 22 mL, 22 mmol) and a solution of sodium hydroxide (193 mg, 4.82 mmol) in water (2 mL). The reaction mixture was stirred at 32° C. for 3 h, then acidified to pH 5 with 1 M aq. hydrochloric acid solution, and extracted with ethyl acetate. The organic layer was dried over sodium sulfate, filtered, and evaporated to produce the title compound (800 mg, 82%), MS: 505 $[M+H]^+$.

Intermediate 6 tert-Butyl 2-(methylsulfonyl)-4-(4,4,5,5-tetramethyl-1,3,2-dioxaborolan-2-yl)benzoate

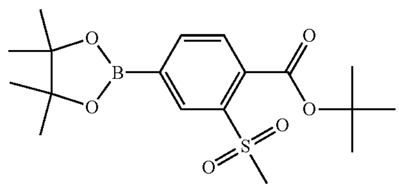 [SMILES: CC(C)(C)OC(=O)c1ccc(B2OC(C)(C)C(C)(C)O2)cc1S(C)(=O)=O]

Step 1: tert-Butyl 4-bromo-2-(methylsulfonyl)benzoate

To a suspension of 4-bromo-2-(methylsulfonyl)benzoic acid (CAS-RN 142994-02-3; 0.89 g, 3.19 mmol) in dry toluene (2 mL) was added N,N-dimethylformamide di-tert-butyl acetal (4.68 g, 20.7 mmol) and the mixture heated to 80° C. for 2 h, then the reaction mixture was partitioned between ethyl acetate and sat. aq. sodium hydrogencarbonate solution. The organic layer was washed with brine, dried over sodium sulfate, filtered and concentrated in vacuo. Chromatography (silica gel; heptane-ethyl acetate gradient) produced the title compound (698 mg, 65%). Light yellow solid, MS: 280.9 $[M+H-isobutene]^+$.

Step 2: tert-Butyl 2-(methylsulfonyl)-4-(4,4,5,5-tetramethyl-1,3,2-dioxaborolan-2-yl)benzoate A light yellow suspension of tert-butyl 4-bromo-2-(methylsulfonyl)benzoate (0.698 g, 2.08 mmol), potassium acetate (715 mg, 7.29 mmol) and bis(pinacolato)diboron (701 mg, 2.71 mmol) in dimethylsulfoxide (5.95 ml) in a pressure tube was sparged with argon for 5 minutes while sonicating the vessel in an ultrasonic bath. Then [1,1'-bis(diphenylphosphino)ferrocene]dichloropalladium(II) (76.2 mg, 104 μmol) was added, degassing continued for 3 minutes, the tube sealed and the reaction heated to 80° C. for 3 hours. After cooling insoluble material was removed by filtration and the reaction mixture was partitioned between ethyl acetate, and brine. The organic layer was dried over sodium sulfate, filtered, and evaporated. Chromatography (silica gel; heptane-ethyl acetate gradient) produced the title compound as a white solid (602 mg, 76%).

Intermediate 6.01 tert-Butyl 2-methoxy-4-(4,4,5,5-tetramethyl-1,3,2-dioxaborolan-2-yl)benzoate

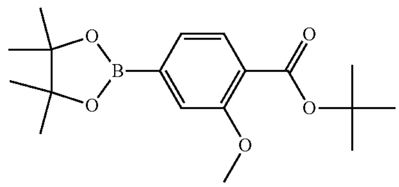 [SMILES: COc1cc(B2OC(C)(C)C(C)(C)O2)ccc1C(=O)OC(C)(C)C]

The title compound was produced in analogy to intermediate 6 from 4-bromo-2-methoxybenzoic acid [CAS-RN 72135-36-5].

Intermediate 7

[1]-(2-tert-Butoxy-2-oxo-ethyl)-2-oxo-4-pyridyl] boronic acid

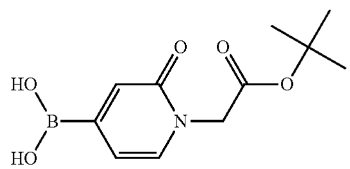 [SMILES: CC(C)(C)OC(=O)Cn1ccc(B(O)O)cc1=O]

A suspension of tert-butyl 2-(4-bromo-2-oxopyridin-1(2H)-yl)acetate (CAS-RN 1630192-25-4; 1.28 g, 4.44 mmol), bis(pinacolato)diboron (1.69 g, 6.66 mmol) and potassium acetate (1.31 g, 13.3 mmol) in 1,4-dioxane (20 mL) was evacuated and purged with argon for 5 min, followed by addition of [1,1'-bis(diphenylphosphino)ferrocene]-dichloropalladium(II) (325 mg, 444 μmol). After purging with argon for additional 2 min, the reaction vessel was sealed and heated at 100° C. for 16 h. The mixture was then cooled to room temperature, filtered through diatomaceous earth. The filtrate was partitioned between ethyl acetate and water, the organic layer was washed with brine, dried over magnesium sulfate, filtered and evaporated. The crude material was purified by reverse phase preparative HPLC using and a gradient from water (+0.05% trifluoroacetic acid) to acetonitrile as eluent to produce the title compound (937 mg, 83%). White solid, MS: 254.2 $[M+H]^+$.

Intermediate 8

[2-[(2-Methylpropan-2-yl)oxycarbonyl]pyrazolo[1,5-a]pyridin-5-yl]boronic acid

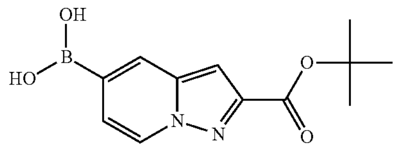 [SMILES: CC(C)(C)OC(=O)c1cc2cc(B(O)O)ccn2n1]

Step 1: tert-Butyl 5-bromopyrazolo[1,5-a]pyridine-2-carboxylate

The title compound was produced in analogy to intermediate 6, step 1 from 5-bromopyrazolo[1,5-a]pyridine-2-carboxylic acid [CAS-RN 1363381-10-5]. White solid, MS: 297.0 $[M+H]^+$.

Step 2: [2-[(2-Methylpropan-2-yl)oxycarbonyl]pyrazolo[1,5-a]pyridin-5-yl]boronic acid The title compound was produced in analogy to intermediate 7 replacing 4-bromo-2-(methylsulfonyl)benzoic acid by tert-butyl 5-bromopyrazolo[1,5-a]pyridine-2-carboxylate. White solid, MS: 207.2 $[M-isobutene+H]^+$.

Intermediate 9

(E)-(1-(3-(tert-butoxy)-3-oxoprop-1-en-1-yl)-2-oxo-1,2-dihydropyridin-4-yl)boronic acid

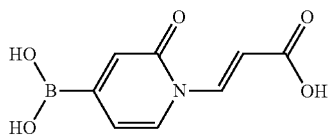 [SMILES: O=C(O)/C=C/n1ccc(B(O)O)cc1=O]

Step 1: tert-Butyl (E)-3-(4-bromo-2-oxopyridin-1(2H)-yl)acrylate

Potassium carbonate (477 mg, 3.45 mmol) was added to a suspension of 4-bromopyridin-2(1H)-one (CAS-RN 13466-38-1; 300 mg, 1.72 mmol) and tert-butyl 3-bromopropanoate (433 mg, 2.07 mmol) in N,N-dimethylformamide (10 mL) and the mixture was stirred for 30 min at 60° C. The reaction mixture was then partitioned between with water and ethyl acetate. The organic layer was washed with brine, dried over magnesium sulfate, filtered, and concentrated. The residue was purified by preparative HPLC using a RediSep Gold: C18 column as the stationary phase and gradient from water (+0.05% trifluoroacetic acid) to acetonitrile as the eluent to produce the title compound (320 mg, 62%). White solid, MS: 300.0 $[M+H]^+$.

Step 2: (E)-(1-(3-(tert-butoxy)-3-oxoprop-1-en-1-yl)-2-oxo-1,2-dihydropyridin-4-yl)boronic acid The title compound was produced in analogy to intermediate 7, replacing tert-butyl 2-(4-bromo-2-oxopyridin-1(2H)-yl)acetate by tert-butyl (E)-3-(4-bromo-2-oxopyridin-1(2H)-yl)acrylate. Off-white solid, MS: 266.3 $[M+H]^+$. The invention will be more fully understood by reference to the following examples. They should however not be construed as limiting the scope of the invention.

Example 19

Antimicrobial Susceptibility Testing

50% Growth Inhibitory Concentration (IC50) Determination

The in vitro antimicrobial activity of the compounds was alternatively determined according to the following procedure:

The assay used a 10-points Iso-Sensitest broth medium to measure quantitatively the in vitro activity of the compounds against *A. baumannii* ATCC 17978.

Stock compounds in DMSO were serially twofold diluted (e.g. range from 50 to 0.097 μM or from 10 to 0.020 μM final concentration) in 384 wells microtiter plates and inoculated with 49 μl the bacterial suspension in Iso-Sensitest medium to have a final cell concentration of ~$5\times10^{(5)}$ CFU/ml in a final volume/well of 50 μl/well. Microtiter plates were incubated at 35±2° C.

Bacterial cell growth was determined with the measurement of optical density at λ=600 nm each 20 minutes over a time course of 16 h.

Growth inhibition was calculated during the logarithmic growth of the bacterial cells with determination of the concentration inhibiting 50% (IC50) and 90% (IC90) of the growth.

Table 1 provides the 50% growth inhibitory concentrations (IC50) in micromoles per liter of the compounds of present invention obtained against the *A. baumannii* strain ATCC17978.

Particular compounds of the present invention exhibit an IC50 (ATCC17978)≤10 μmol/l.

More particular compounds of the present invention exhibit an IC50 (ATCC17978)≤1 μmol/l.

Most particular compounds of the present invention exhibit an IC50 (ATCC17978)≤0.5 μmol/l.

TABLE 1

(i) 50% growth inhibition concentrations (IC50) in micromoles per liter of the compounds of present invention obtained against *A. baumannii* strain ATCC17978; (ii) Plasma precipitation minimal effect concentration (MEC) (μmol/l); (iii) ALogP, atomic partition coefficient, calculated with BIOVIA Pipeline Pilot 2017 R2.

| Example | IC50 ATCC17978 [μmol/l] | Plasma precipitation MEC (μmol/l) | ALogP |
|---|---|---|---|
| 1.00 | 0.098 | 1110 | 1.37 |
| 2.00 | 0.073 | 950 | 1.56 |
| 2.01 | 0.020 | 820 | 1.69 |
| 2.02 | 0.029 | | 1.31 |
| 2.03 | 0.031 | >1670 | −0.10 |
| 3.00 | 0.039 | | 1.79 |
| 4.00 | 0.019 | | 1.81 |
| 5.00 | 0.067 | | 1.64 |
| 6.00 | 0.023 | 1090 | 1.29 |
| 7.00 | 0.028 | | 1.95 |
| 7.01 | 0.046 | 1650 | −0.18 |
| 8.00 | 0.020 | | 1.10 |
| 8.01 | 0.028 | 760 | 1.76 |
| 8.02 | 0.019 | 380 | 1.30 |
| 8.03 | 0.078 | 760 | 1.08 |
| 9.00 | 0.020 | 870 | 1.58 |
| 9.01 | 0.081 | >1690 | −0.56 |
| 9.02 | 0.088 | | −0.41 |
| 10.00 | 0.024 | 870 | 1.63 |
| 10.01 | 0.078 | >1700 | −0.51 |
| 11.00 | 0.071 | 1720 | 1.13 |
| 12.00 | 0.019 | | 1.58 |
| 13.00 | 0.020 | | 1.00 |
| 14.00 | 0.021 | | 1.12 |
| 14.01 | 0.090 | 880 | 0.40 |
| 15.00 | 0.020 | | 1.45 |
| 16.00 | 0.020 | | 1.00 |
| 17.00 | 0.075 | | 0.91 |
| 18.00 | 0.075 | >1760 | 0.22 |

Example 20

Plasma Precipitation Screening Assay

Principle

An aliquot (10 μL) of compound solubilized in physiological buffer or the formulation used for its parenteral administration in vivo, and of various dilutions thereof in phosphate-buffered saline (PBS), is mixed 1:1 with rat plasma. After 10 minutes incubation at room temperature the UV-absorption of the mixtures is measured and compared to absorption of blank plasma or plasma with vehicle solution. A significant (often concentration dependent) increase of absorption is indicative of precipitation.

Materials and Methods

Whole blood is obtained from WISTAR rats (Hanbrl:Wist SPF) under terminal anaesthesia after intraperitoneal injection of a pentobarbital solution (from animals euthanized for collection of tissue for other experimental purposes). Blood is collected in 1.2 mL of Heparin S-Monovette tubes (Sarstedt) for the preparation of heparin plasma.

The tubes are then centrifuged for 5 min at 5200 g at room temperature to isolate the plasma supernatant. The plasma is used in the assay within 48 h of collection (storage at 4° C.).

Test compounds are received as powder or formulated. When obtained as powder, they are solubilized in 0.9% aq. sodium chloride solution in order to get the highest indicated concentration to be tested. The solubility is visually checked and the solutions are filtered using 0.45 PVDF hydrophilic filters (Durapore®, Darmstadt, Germany), to remove possible solid impurities. pH of this initial solution might be measured in the filtered stock solutions, before proceeding to prepare a compound dilution series in PBS (1:1-dilution steps).

The assay is conducted in 384-well plates. 10 μL of rat plasma is added to 10 μL of the various compound solutions. The assay is performed in duplicate. 10 μL of vehicle (0.9% aq. sodium chloride solution, PBS) added to the plasma is used as a negative control. The absorption is measured at 362 nm.

(11S,14S,17S)-14-(4-Aminobutyl)-11-(3-aminopropyl)-22,25-dichloro-17-(1H-indol-3-ylmethyl)-16-methyl-2-thia-4,10,13,16,19-pentazatricyclo[19.4.0.03,8]pentacosa-1(25),3(8),4,6,21,23-hexaene-12,15,18-trione [CAS-RN 2097284-11-0], which is known to induce precipitation in plasma, is included in all assay runs as positive control and comparator.

Raw data obtained are absorbance data. The difference between absorbance of the sample and mean absorbance of vehicle is calculated. The minimal effect concentration (MEC) is defined as the lowest concentration giving an absorbance difference, $OD_{362}\geq 0.05$.

Results are provided in Table 1 above.

In one embodiment, the present invention provides a compound of formula (I) as described herein, or a pharmaceutically acceptable salt thereof, wherein said compound has a threshold concentration for blood plasma precipitation of >470 μM, preferably >760 μM, more preferably >870 μM, in particular >1000 μM.

In one embodiment, the present invention provides a compound of formula (I) as described herein, or a pharmaceutically acceptable salt thereof, wherein said compound has a threshold concentration for blood plasma precipitation of >470 μM, preferably >760 μM, more preferably >870 μM, in particular >1000 μM, wherein said threshold concentration for blood plasma precipitation is determined following the assay of present Example 20.

COMPARATIVE EXAMPLES

| Example/Structure | IC50 ATCC17978 [μmol/l] | Plasma precipitation MEC (μmol/l) | ALogP |
|---|---|---|---|
| Example 239 of WO2017/072062 | 0.020 | 470 | 2.03 |
| 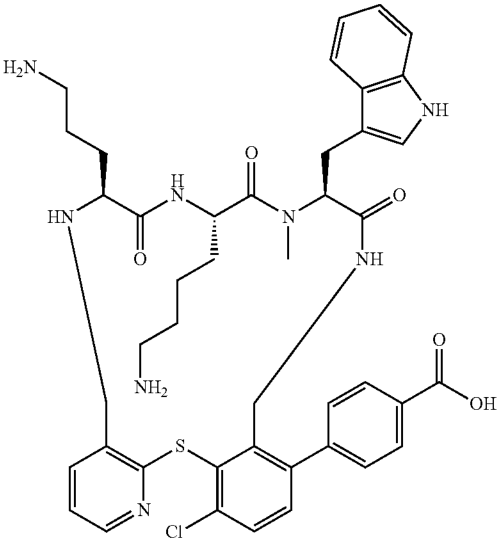 [SMILES: CN1C(=O)[C@H](CCCCN)NC(=O)[C@H](CCCN)NCc2cccnc2Sc2c(Cl)ccc(-c3ccc(C(=O)O)cc3)c2CNC(=O)[C@@H]1Cc1c[nH]c2ccccc12] | | | |
| Example 241 of WO2017/072062 | 0.050 | 95 | 1.87 |

-continued

| Example/Structure | IC50 ATCC17978 [μmol/l] | Plasma precipitation MEC (μmol/l) | ALogP |
|---|---|---|---|
| 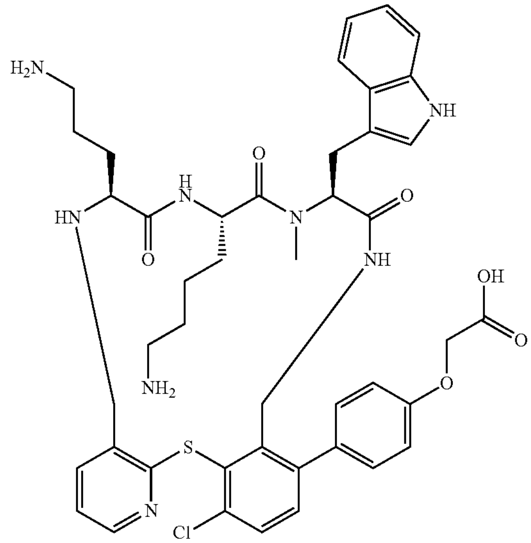 [SMILES: CN1C(=O)[C@H](CCCCN)NC(=O)[C@H](CCCN)NCc2cccnc2Sc2c(Cl)ccc(-c3ccc(OCC(=O)O)cc3)c2CNC(=O)[C@@H]1Cc1c[nH]c2ccccc12] | | | |
| Example 38 of WO2017/072062 | 0.042 | 52 | 4.02 |
| 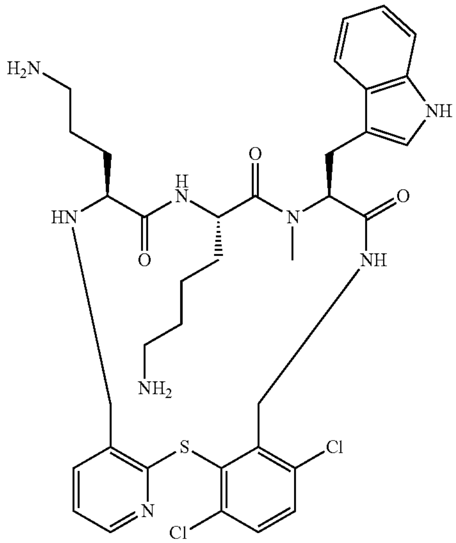 [SMILES: CN1C(=O)[C@H](CCCCN)NC(=O)[C@H](CCCN)NCc2cccnc2Sc2c(Cl)ccc(Cl)c2CNC(=O)[C@@H]1Cc1c[nH]c2ccccc12] | | | |

Example 21

Single Dose Pharmacokinetic Study in Male Rats

Three male rats were administered with compound formulation (3 mg/mL in 0.9% saline) as an intravenous bolus dose of 6 mg/kg.

Blood was sampled at 0.08, 0.25, 0.5, 1, 2, 4, 7 and 24 hours after administration and the blood collecting tubes were centrifuged for 5 min at 5200 g at room temperature to isolate the plasma supernatant.

Concentrations of compound in plasma were analyzed using a LC-MS method with a calibration range of 1-2500 ng/mL. The clearance values are calculated using methods described in the art and are summarised in Example 23.

Example 22

Single Dose Pharmacokinetic Study in Male Cynomolgus Monkeys

Three male monkeys were administered with compound formulation (2 mg/mL in 0.9% saline) as an intravenous bolus dose of 1 mg/kg.

Blood was sampled at 0.08, 0.25, 0.5, 1, 2, 4, 7 and 24 hours after administration and the blood collecting tubes were centrifuged for 5 min at 5200 g at room temperature to isolate the plasma supernatant.

Concentrations of compound in plasma were analyzed using a LC-MS method with a calibration range of 0.5-2500 ng/mL and are summarised in Example 23.

Example 23

Scaling Hepatocyte Uptake Data to Predict In Vivo Clearance

Principle

The compounds of the present invention are cleared through hepatic uptake, which can be determined experimentally in vitro using methods described in the art (e. g., K. Menochet, K. E. Kenworthy, J. B. Houston, A. Galetin, *Journal of Pharmacology and Experimental Therapeutics* 2012, 34, 2). In cases where the scaled in vitro hepatocyte uptake clearance data correspond to the clearance observed in animals, a meaningful prediction of the human clearance can be made on the basis of in vitro human hepatocyte uptake data.

Material and Methods (a) Hepatocyte Uptake Assay

The hepatocyte uptake assay was performed manually in 24-well plates in analogy to a protocol described in the literature (K. Menochet, K. E. Kenworthy, J. B. Houston, A. Galetin, *Journal of Pharmacology and Experimental Therapeutics* 2012, 34, 2). Briefly, primary hepatocytes isolated from different species (rat, human, monkey) were plated in multi-well plates, where they attached and formed a monolayer at the bottom of each well within a few hours under incubation at 370° C. For assay, cells were removed from incubation and washed in uptake buffer (HBSS calcium magnesium [Gibco Invitrogen 14065056], 20 mM HEPES, 37° C.) and allowed to acclimatize for a few minutes. Uptake was initiated by the addition of uptake buffer spiked with test compound in the presence/absence of a pan-inhibitor cocktail, which can block all major drug transport pathways, and incubated for a set time (typically 1-3 minutes). Uptake was stopped with the addition of an excess of ice-cold buffer (HBSS calcium magnesium+0.2% bovine serum albumin), which immediately stops active uptake and dilutes the dose compound. This was followed with two rapid cycles of washing with warm buffer (HBSS calcium magnesium+0.2% bovine serum albumin, 37° C., then HBSS calcium magnesium, 37° C.). The latter step was to minimize non-specific binding and unbound excess compound from the well. Next, the cell monolayer was lysed using acetonitrile/water 3:1, and the intracellular concentration was measured using LC-MS/MS.

(b) Scaling Hepatocyte Uptake Data

Total ($CL_{uptake}$) and passive ($CL_{passive}$) uptake clearance values were measured from initial uptake rates in the absence and presence of inhibitors. Uptake rates were calculated over 10 minutes at 37° C. from the slope of the linear regression of the cell concentrations versus time plot. Total and passive uptake clearance values were calculated by dividing the slope by the initial substrate concentration and were normalized for protein content.

Rat in vitro intrinsic clearance values ($CL_{int,H}$) expressed as μL/min/mg protein were scaled to the in vivo equivalent whole liver by multiplying with hepatic total protein (200 mg/g liver) and average liver weight of 40 g liver/kg body weight, assuming a total body weight of 250 g.

Cynomolgus and human $CL_{int,H}$ expressed as μL/min/mg protein were converted to μL/min/$10^6$ cells by assuming 1 mg protein is equal to 1.5 million cells and scaled to the in vivo equivalent whole liver by multiplying with hepatocellularity (120 million cells/g liver) and average liver weight of 30 and 21.4 g liver/kg body weight in cynomolgus monkey and human, respectively.

In vivo $CL_{int,}$h was estimated using the well-stirred liver model (K. S. Pang, M. Rowland, *Journal of Pharmacokinetics and Biopharmaceutics* 1977, 5, 625);

$$CL_h = \frac{Q_h \cdot fu \cdot CL_{int,h}}{Q_{h+} fu \cdot CL_{int,h}}$$

where $Q_h$ represents the blood flow in rats (55.2 mL/min/kg), monkeys (43.6 mL/min/kg) or humans (21 mL/min/kg); $f_u$ was assumed to be 1. The scaled clearance values for rat, cynomolgus monkeys, and human are reported in the table below.

RESULTS

The table below summarises the scaled in vitro and in vivo clearance values for rat and monkey. As can be seen in vivo clearance for rat and cynomolgus monkey can be predicted within 2-fold from the scaled in vitro clearance values. The scaled human clearance for Example 1 compares favourably with that of a previously disclosed structurally similar molecule, leading to a low predicted clearance (0.46 mL/min/kg) in human.

Example 1

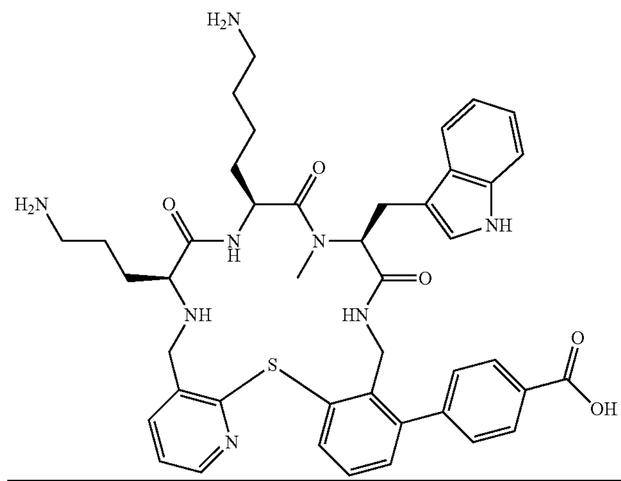

| | in vitro scaled | observed in vivo |
|---|---|---|
| rat clearance (mL/min/kg) | 14.5 | 14.3 |
| cynomolgus monkey clearance (mL/min/kg) | 3.8 | 4.8 |
| human clearance (mL/min/kg) | 0.46 | |

Example 239 of WO2017/072062

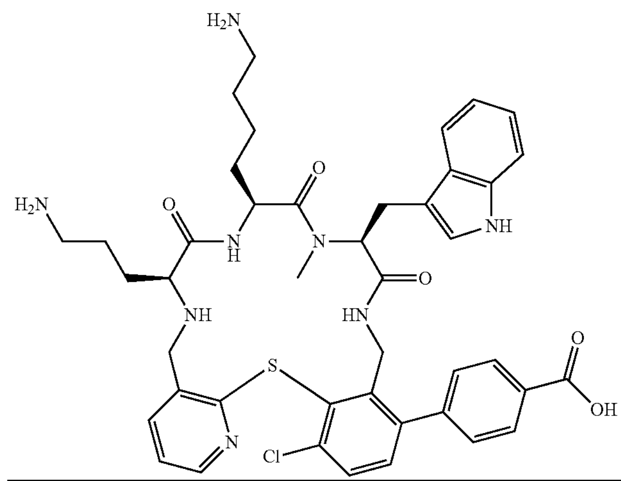

| | in vitro scaled | observed in vivo |
|---|---|---|
| rat clearance (mL/min/kg) | 28.7 | 23.5 |
| cynomolgus monkey clearance (mL/min/kg) | 28.3 | 14.5 |
| human clearance (mL/min/kg) | 3.91 | |

The invention claimed is:

1. A method for the treatment or prevention of infections and resulting diseases caused by *Acinetobacter baumannii*, the method comprising administering a compound, or a pharmaceutically acceptable salt thereof, to a human being or an animal in need thereof, wherein the compound is selected from the group consisting of:

4-[(11S,14S,17S)-14-(4-aminobutyl)-11-(3-aminopropyl)-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid;

2-chloro-4-[rac-(11S,14S,17S)-14-(4-aminobutyl)-11-(3-aminopropyl)-25-chloro-17-(1H-indol-3-ylmethyl)-16-methyl-12,15,18-trioxo-2-thia-4,7,10,13,16,19-hexazatricyclo[19.4.0.03.8]pentacosa-1(21), 3,5,7,22,24-hexaen-22-yl]benzoic acid;

4-[(11S,14S,17S)-14-(4-aminobutyl)-11-(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid;

4-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]-2-methylsulfonyl-benzoic acid;

4-[(11S,14S,17S)-14-(4-aminobutyl)-11-(3-aminopropyl)-16-methyl-17-[(2-methyl-1H-indol-3-yl)methyl]-12,15,18-trioxo-2-thia-4,10,13,16,19-pentazatricyclo[19.4.0.03,8]pentacosa-1(25),3,5,7,21,23-hexaen-22-yl]benzoic acid;

4-[(11S,14S,17S)-14-(4-aminobutyl)-11-(3-aminopropyl)-17-(1H-indol-3-ylmethyl)-16,25-dimethyl-12,15,18-trioxo-2-thia-4,10,13,16,19-pentazatricyclo[19.4.0.03,8]pentacosa-1(25), 3(8),4,6,21,23-hexaen-22-yl]benzoic acid;

2-methoxy-4-[rac-(11S,14S,17S)-14-(4-aminobutyl)-11-(3-aminopropyl)-25-chloro-17-(1H-indol-3-ylmethyl)-16-methyl-12.15,18-trioxo-2-thia-4,7,10,13,16,19-hexazatricyclo[19.4.0.03,8]pentacosa-1(25),3(8),4,6,21,23-hexaen-22-yl]benzoic acid;

2-[4-[(11S,14S,17S)-14-(4-aminobutyl)-11-(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]-2-oxo-1-pyridyl]acetic acid;

4-[(11S,14S,17S)-14-(4-aminobutyl)-11-(3-aminopropyl)-17-(1H-indol-3-ylmethyl)-25-methoxy-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid;

5-[(11S,14S,17S)-11,14-bis(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]pyridine-2-carboxylic acid;

2-[4-[(11S,14S,17S)-14-(4-aminobutyl)-11-(3-aminopropyl)-25-chloro-17-(1H-indol-3-ylmethyl)-16-methyl-12.15,18-trioxo-2-thia-4,10,13,16,19-pentazatricyclo[19.4.0.03,8]pentacosa-1(21),3,5,7,22,24-hexaen-22-yl]-2-oxo-1-pyridyl]acetic acid;

2-[4-[(11S,14S,17S)-14-(4-aminobutyl)-11-(3-aminopropyl)-17-(1H-indol-3-ylmethyl)-16,25-dimethyl-12,15,18-trioxo-2-thia-4,10,13,16,19-pentazatricyclo[19.4.0.03,8]pentacosa-1(25),3(8),4,6,21,23-hexaen-22-yl]-2-oxo-1-pyridyl]acetic acid;

4-[(11S,14S,17S)-14-(4-aminobutyl)-11-(3-aminopropyl)-17-(1H-indol-3-ylmethyl)-16-methyl-12,15,18-trioxo-2-thia-4,10,13,16,19,24-hexazatricyclo[19.4.0.03,8]pentacosa-1(25),3(8),4,6,21,23-hexaen-22-yl]benzoic acid;

2-[4-[(11S,14S,17S)-14-(4-aminobutyl)-11-(3-aminopropyl)-25-chloro-16-methyl-17-[(2-methyl-1H-indol-3-yl)methyl]-12,15,18-trioxo-2-thia-4,10,13,16,19-pentazatricyclo[19.4.0.03,8]pentacosa-1(25),3(8),4,6,21,23-hexaen-22-yl]-2-oxo-1-pyridyl]acetic acid; and 5-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]pyrazolo [1,5-a]pyridine-2-carboxylic acid.

2. A method for the treatment or prevention of infections and resulting diseases caused by *Acinetobacter baumannii*, the method comprising administering a pharmaceutical composition to a human being or an animal in need thereof, wherein the pharmaceutical composition comprises a compound, or a pharmaceutically acceptable salt thereof, and one or more pharmaceutically acceptable excipients, wherein the compound is selected from the group consisting of:

4-[(11S,14S,17S)-14-(4-aminobutyl)-11-(3-aminopropyl)-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid;

2-chloro-4-[rac-(11S,14S,17S)-14-(4-aminobutyl)-11-(3-aminopropyl)-25-chloro-17-(1H-indol-3-ylmethyl)-16-methyl-12,15,18-trioxo-2-thia-4,7,10,13,16,19-hexazatricyclo[19.4.0.03,8]pentacosa-1(21),3,5,7,22,24-hexaen-22-yl]benzoic acid;

4-[(11S,14S,17S)-14-(4-aminobutyl)-11-(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid;

4-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]-2-methylsulfonyl-benzoic acid;

4-[(11S,14S,17S)-14-(4-aminobutyl)-11-(3-aminopropyl)-16-methyl-17-[(2-methyl-1H-indol-3-yl)methyl]-12,15,18-trioxo-2-thia-4,10,13,16,19-pentazatricyclo[19.4.0.03,8]pentacosa-1(25),3,5,7,21,23-hexaen-22-yl]benzoic acid;

4-[(11S,14S,17S)-14-(4-aminobutyl)-11-(3-aminopropyl)-17-(1H-indol-3-ylmethyl)-16,25-dimethyl-12,15,18-trioxo-2-thia-4,10,13,16,19-pentazatricyclo[19.4.0.03,8]pentacosa-1(25),3(8),4,6,21,23-hexaen-22-yl]benzoic acid;

2-methoxy-4-[rac-(11S,14S,17S)-14-(4-aminobutyl)-11-(3-aminopropyl)-25-chloro-17-(1H-indol-3-ylmethyl)-16-methyl-12,15,18-trioxo-2-thia-4,7,10,13,16,19-hexazatricyclo[19.4.0.03,8]pentacosa-1(25),3(8),4,6,21,23-hexaen-22-yl]benzoic acid;

2-[4-[(11S,14S,17S)-14-(4-aminobutyl)-11-(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]-2-oxo-1-pyridyl]acetic acid;

4-[(11S,14S,17S)-14-(4-aminobutyl)-11-(3-aminopropyl)-17-(1H-indol-3-ylmethyl)-25-methoxy-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid;

5-[(11S,14S,17S)-11,14-bis(3-aminopropyl)-25-fluoro-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]pyridine-2-carboxylic acid;

2-[4-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(21),3,5,7,22,24-hexaen-22-yl]-2-oxo-1-pyridyl]acetic acid;

2-[4-[(11S,14S,17S)-14-(4-aminobutyl)-11-(3-aminopropyl)-17-(1H-indol-3-ylmethyl)-16,25-dimethyl-12,15,18-trioxo-2-thia-4,10,13,16,19-pentazatricyclo[19.4.0.03,8]pentacosa-1(25),3(8),4,6,21,23-hexaen-22-yl]-2-oxo-1-pyridyl]acetic acid;

4-[(11S,14S,17S)-14-(4-aminobutyl)-11-(3-aminopropyl)-17-(1H-indol-3-ylmethyl)-16-methyl-12,15,18-trioxo-2-thia-4,10,13,16,19,24-hexazatricyclo [19.4.0.03,8]pentacosa-1(25),3(8),4,6,21,23-hexaen-22-yl]benzoic acid;

2-[4-[(11S,14S,17S)-14-(4-aminobutyl)-11-(3-aminopropyl)-25-chloro-16-methyl-17-[(2-methyl-1H-indol-3-yl)methyl]-12,15,18-trioxo-2-thia-4,10,13,16,19-pentazatricyclo[19.4.0.03,8]pentacosa-1(25),3(8),4,6,21,23-hexaen-22-yl]-2-oxo-1-pyridyl]acetic acid; and 5-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19-pentazatricyclo [19.4.0.03,8]pentacosa-1(25),3(8),4,6,21,23-hexaen-22-yl]pyrazolo [1,5-a]pyridine-2-carboxylic acid.

3. The method of claim 1, wherein the compound is selected from the group consisting of:

4-[(11S,14S,17S)-14-(4-aminobutyl)-11-(3-aminopropyl)-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl] benzoic acid;

2-[4-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19-pentazatricyclo [19.4.0.03,8]pentacosa-1(21),3,5,7,22,24-hexaen-22-yl]-2-oxo-1-pyridyl]acetic acid; and 4-[(11S,14S,17S)-14-(4-aminobutyl)-11-(3-aminopropyl)-17-(1H-indol-3-ylmethyl)-16-methyl-12,15,18-trioxo-2-thia-4,10, 13, 16,19,24-hexazatricyclo [19.4.0.03,8]pentacosa-1(25),3(8),4,6,21,23-hexaen-22-yl]benzoic acid;

or a pharmaceutically acceptable salt thereof.

4. The method of claim 1, wherein the compound is

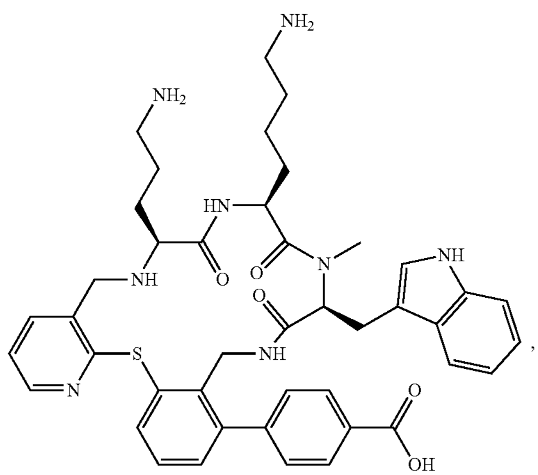 [SMILES: CN1C(=O)[C@H](CCCCN)NC(=O)[C@H](CCCN)NCc2cccnc2Sc2cccc(-c3ccc(C(=O)O)cc3)c2CNC(=O)[C@@H]1Cc1c[nH]c2ccccc12]

4-[(11S,14S,17S)-14-(4-aminobutyl)-11-(3-aminopropyl)-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl] benzoic acid, or a pharmaceutically acceptable salt thereof.

5. The method of claim 1, wherein the compound is

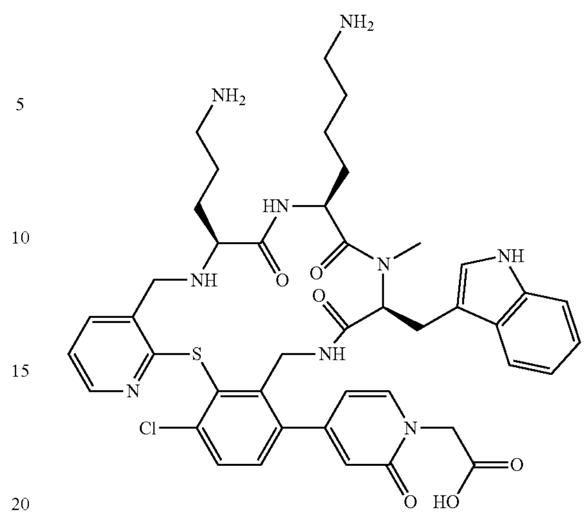

2-[4-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19-pentazatricyclo [19.4.0.03,8]pentacosa-1(21),3,5,7,22,24-hexaen-22-yl]-2-oxo-1-pyridyl]acetic acid, or a pharmaceutically acceptable salt thereof.

6. The method of claim 1, wherein the compound is

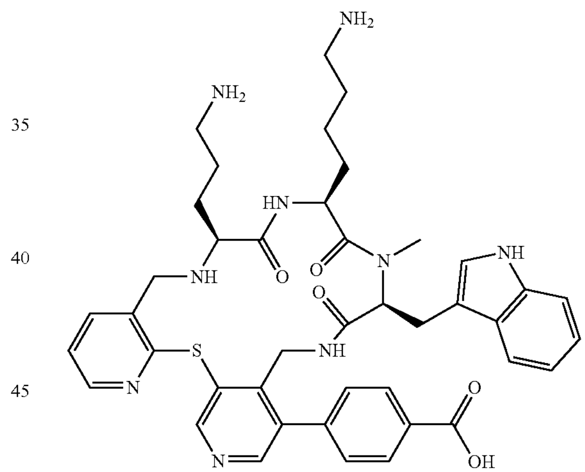

4-[(11S,14S,17S)-14-(4-aminobutyl)-11-(3-aminopropyl)-17-(1H-indol-3-ylmethyl)-16-methyl-12,15,18-trioxo-2-thia-4,10,13,16,19,24-hexazatricyclo [19.4.0.03,8]pentacosa-1(25),3(8),4,6,21,23-hexaen-22-yl]benzoic acid, or a pharmaceutically acceptable salt thereof.

7. The method of claim 2, wherein the compound is selected from the group consisting of:

4-[(11S,14S,17S)-14-(4-aminobutyl)-11-(3-aminopropyl)-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl] benzoic acid;

2-[4-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19-pentazatricyclo [19.4.0.03,8]pentacosa-1(21),3,5,7,22,24-hexaen-22-yl]-2-oxo-1-pyridyl]acetic acid; and 4-[(11S,14S,17S)-14-(4-aminobutyl)-11-(3-aminopropyl)-17-(1H-indol-3-ylmethyl)-16-methyl-12,15,18-trioxo-2-thia-4,10,13,16,19,24-hexazatricyclo[19.4.0.03,8]pentacosa-1(25),3(8),4,6,21,23-hexaen-22-yl]benzoic acid;

or a pharmaceutically acceptable salt thereof.

8. The method of claim 2, wherein the compound is

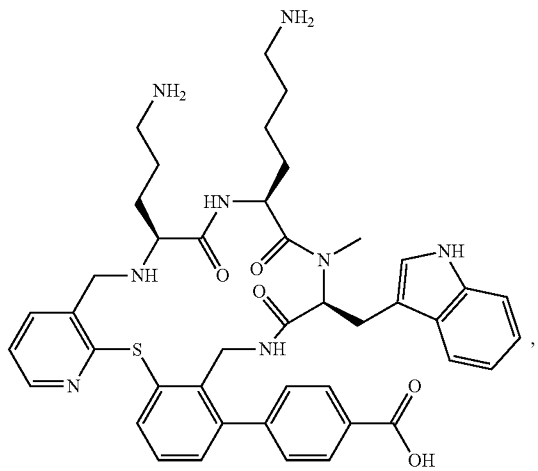

4-[(11S,14S,17S)-14-(4-aminobutyl)-11-(3-aminopropyl)-17-(1H-indol-3-ylmethyl)-16-methyl-12,15,18-trioxo-2-thia-4,10,13,16,19-pentazatricyclo[19.4.0.03,8]pentacosa-1(25),3(8),4,6,21,23-hexaen-22-yl]benzoic acid, or a pharmaceutically acceptable salt thereof.

9. The method of claim 2, wherein the compound is

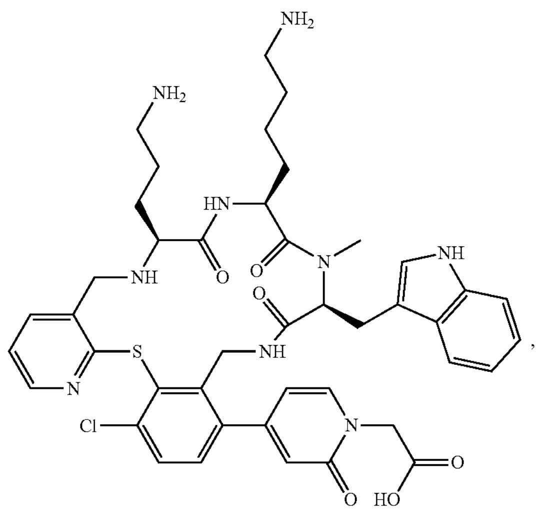 [SMILES: CN1C(=O)[C@H](CCCCN)NC(=O)[C@H](CCCN)NCc2cccnc2Sc2c(Cl)ccc(-c3ccn(CC(=O)O)c(=O)c3)c2CNC(=O)[C@@H]1Cc1c[nH]c2ccccc12]

2-[4-[(11S,14S,17S)-14-(4-aminobutyl)-11-(3-aminopropyl)-25-chloro-17-(1H-indol-3-ylmethyl)-16-methyl-12,15,18-trioxo-2-thia-4,10,13,16,19-pentazatricyclo[19.4.0.03,8]pentacosa-1(21),3,5,7,22,24-hexaen-22-yl]-2-oxo-1-pyridyl]acetic acid, or a pharmaceutically acceptable salt thereof.

10. The method of claim 2, wherein the compound is

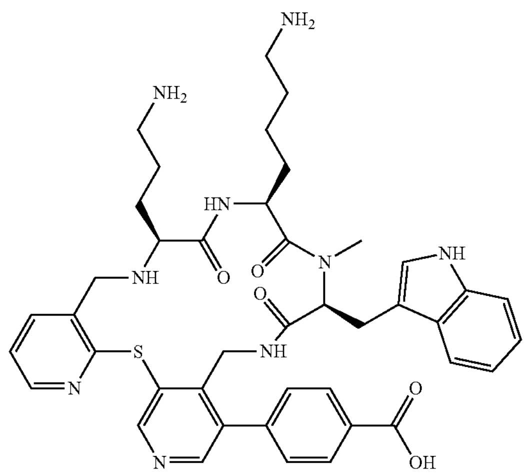

4-[(11S,14S,17S)-14-(4-aminobutyl)-11-(3-aminopropyl)-17-(1H-indol-3-ylmethyl)-16-methyl-12,15,18-trioxo-2-thia-4,10,13,16,19,24-hexazatricyclo[19.4.0.03,8]pentacosa-1(25),3(8),4,6,21,23-hexaen-22-yl]benzoic acid, or a pharmaceutically acceptable salt thereof.

* * * * *